US010329579B2

(12) United States Patent
Schultheiss et al.

(10) Patent No.: US 10,329,579 B2
(45) Date of Patent: Jun. 25, 2019

(54) GENES TO ENHANCE DISEASE RESISTANCE IN CROPS

(71) Applicant: BASF Plant Science Company GmbH, Ludwigshafen (DE)

(72) Inventors: Holger Schultheiss, Boehl-Iggelheim (DE); Nadine Tresch, Kirchheim (DE); Uwe Conrath, La Calamine (BE); Katharina Goellner, Cologne (DE); Caspar Langenbach, Aachen (DE)

(73) Assignee: BASF PLANT SCIENCE COMPANY GMBH, Ludwigshafen (DE)

( * ) Notice: Subject to any disclaimer, the term of this patent is extended or adjusted under 35 U.S.C. 154(b) by 174 days.

(21) Appl. No.: 14/367,296

(22) PCT Filed: Dec. 14, 2012

(86) PCT No.: PCT/IB2012/057313
§ 371 (c)(1),
(2) Date: Jun. 20, 2014

(87) PCT Pub. No.: WO2013/093738
PCT Pub. Date: Jun. 27, 2013

(65) Prior Publication Data

US 2015/0322454 A1 Nov. 12, 2015

Related U.S. Application Data

(60) Provisional application No. 61/579,700, filed on Dec. 23, 2011.

(30) Foreign Application Priority Data

Dec. 23, 2011 (EP) .................................... 11195696

(51) Int. Cl.
*C12N 15/82* (2006.01)

(52) U.S. Cl.
CPC ................................ *C12N 15/8282* (2013.01)

(58) Field of Classification Search
None
See application file for complete search history.

(56) References Cited

U.S. PATENT DOCUMENTS 4,101,673 A * 7/1978 Chang .................... A61K 31/23 514/547
7,947,876 B2 5/2011 Sugita et al.
7,968,765 B2 * 6/2011 Frankard ............ C12N 15/8261 435/410
2009/0126046 A1 * 5/2009 Valerie ............... C12N 15/8261 800/290
2014/0137284 A1 5/2014 Schultheiss et al.

FOREIGN PATENT DOCUMENTS

| | | | |
|---|---|---|---|
| EP | 1283214 | | 2/2003 |
| WO | WO 2004046357 | | 6/2004 |
| WO | WO 2006/005771 | * | 1/2006 |
| WO | WO 2006030492 | | 3/2006 |
| WO | WO 2012023099 | | 2/2012 |
| WO | WO 2012023111 | | 2/2012 |
| WO | WO 2012172498 | | 12/2012 |
| WO | WO 2013001435 | | 1/2013 |
| WO | WO 2013149801 | | 10/2013 |
| WO | WO 2013149804 | | 10/2013 |
| WO | WO 2013152917 | | 10/2013 |
| WO | WO 2014024079 | | 2/2014 |
| WO | WO 2014024090 | | 2/2014 |
| WO | WO 2014024102 | | 2/2014 |
| WO | WO 2014041444 | | 3/2014 |

OTHER PUBLICATIONS

Cheuk et al (2003, GenBank: BT008411.1, https://www.ncbi.nlm.nih.gov/nuccore/BT008411.1.*
Cazale et al (2009, J. Exp. Bot. 9:2653-2664).*
Antolin-Llovera et al, 2012, Ann. Rev. Phytopathol. 50:451-73.*
Guo et al, 2004, Proc. Natl. Acad. Sci. USA 101: 9205-9210.*
Gou et al (2010, BMC Genomics 11:19).*
Bernier and Berna, "Germins and Germin-Like Proteins: Plant Do-All Proteins. But What do they do Exactly?" Plant Physiol. Biochem., vol. 39, (2001), pp. 545-554.
Database Genbank [on-line], Database Accession No. AAO41889.1, Unknown Protein [*Arabidopsis thaliana*], (Feb. 14, 2003).
Database Genbank [on-line], Database Accession No. NP_564220.1, "Uncharacterized Protein [*Arabidopsis thaliana*]," (May 28, 2011).
Database Genbank [on-line], Database Accession No. XP_002890704.1, Hypothetical Protein ARALYDRAFT_472890 [*Arabidopsis lyrata subsp. lyrata*], (Jun. 11, 2010).
Heath, "Cellular Interactions Between Biotrophic Fungal Pathogens and Host or Nonhost Plants," Can. J. Plant Pathol., vol. 24, (2002), 259-264.
International Preliminary Report on Patentability, issued in PCT/IB2012/057313, dated Jul. 3, 2014.
International Search Report, issued in PCT/IB2012/057313, dated Apr. 24, 2013.

(Continued)

*Primary Examiner* — Anne Kubelik
(74) *Attorney, Agent, or Firm* — Marshall, Gerstein & Borun LLP

(57) ABSTRACT

The present invention pertains to methods, means and uses of nucleic acids and polypeptides for conferring, modifying or improving plant resistance against fungal infections. Particularly, the invention provides nucleic acids and polypeptides for conferring, modifying or improving plant resistance against fungal infections. The invention also provides vectors, cells and plants. Also, the invention provides methods for creating corresponding plant cells and plants, and for identification of agents for conferring, modifying or improving plant resistance against fungal infections.

6 Claims, 12 Drawing Sheets

Figure 1A:
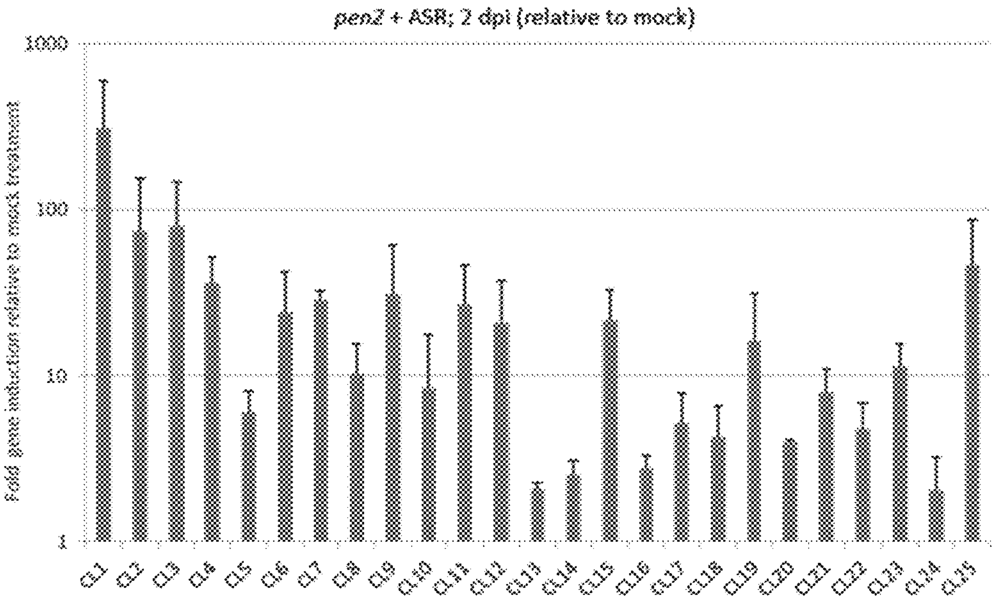
Figure 1B:
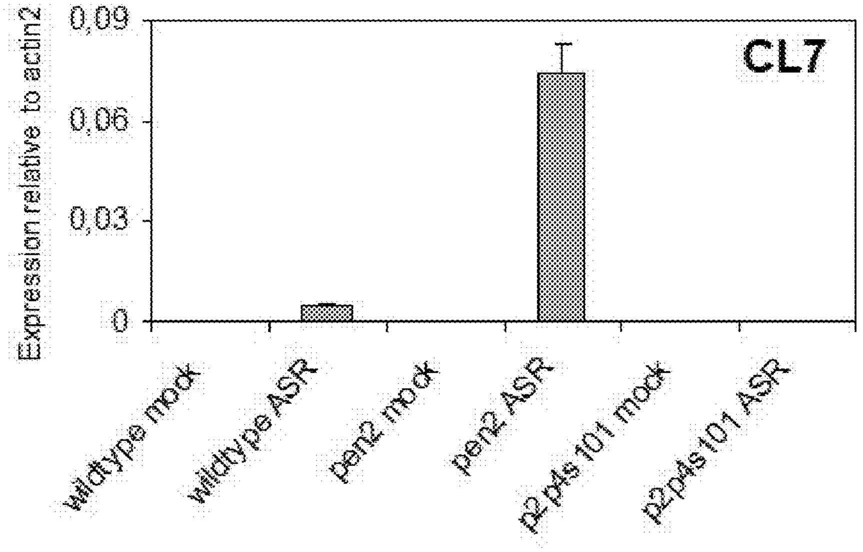
Figure 1B:
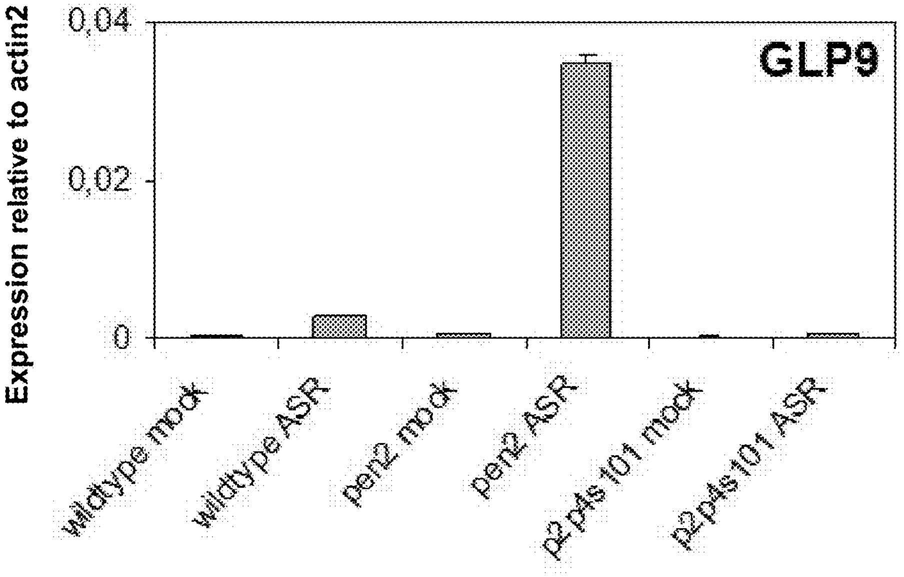

Specification includes a Sequence Listing.

(56) References Cited

OTHER PUBLICATIONS

Lipka et al., "Pre- and Postinvasion Defenses Both Contribute to Nonhost Resistance in *Arabidopsis*," Science, vol. 310, (Nov. 18, 2005), pp. 1180-1183.

Lorang et al., "Plant Disease Susceptibility Conferred by a "Resistance" Gene," PNAS, vol. 104, No. 37, (Sep. 11, 2007), pp. 14861-14866.

Morillo and Tax, "Functional Analysis of Receptor-Like Kinases in Monocots and Dicots," Current Opinion in Plant Biology, vol. 9, (2006), pp. 460-469.

Neu et al., "Cytological and Molecular Analysis of the *Horedeum vulgare-Puccinia triticina* Nonhost Interaction," MPMI, vol. 16, No. 7, (2003), pp. 626-633.

Nürnberger and Kemmerling, "Receptor Protein Kinases—Pattern Recognition Receptors in Plant Immunity," TRENDS in Plant Science, vol. 11, No. 11, (2006), pp. 519-522.

Richards et al., "Aluminum Induces Oxidative Stress Genes in *Arabidopsis thaliana*," Plant Physiol., vol. 116, (1998), pp. 409-418.

Rytter, "Additional Alternative Hosts of *Phakopsora pachyrhizi*, Causal Agent of Soybean Rust," Plant Disease, vol. 87, (1984), pp. 818-819.

Soybean Rust Workshop, Sinclair and Harman, eds., (Aug. 9-11, 1995), pp. 1-11.

* cited by examiner

| Figure 12 | |
|---|---|
| **SEQ ID NO:** | **Description of the sequence listing** |
| **SEQ ID NO:1** | full-length sequence of the CL13 gene from Arabidopsis thaliana |
| **SEQ ID NO:2** | sequence of the CL13 protein from Arabidopsis thaliana |
| **SEQ ID NO:3** | full-length sequence of the CL1 gene from Arabidopsis thaliana |
| **SEQ ID NO:4** | full-length sequence of the CL1 gene from Arabidopsis thaliana, variant |
| **SEQ ID NO:5** | sequence of the CL1 protein from Arabidopsis thaliana |
| **SEQ ID NO:6** | sequence of the CL1 protein from Arabidopsis thaliana, variant |
| **SEQ ID NO:7** | full-length sequence of the CL4 gene from Arabidopsis thaliana |
| **SEQ ID NO:8** | sequence of the CL4 protein from Arabidopsis thaliana |
| **SEQ ID NO:9** | full-length sequence of the CL17 gene from Arabidopsis thaliana |
| **SEQ ID NO:10** | sequence of the CL17 protein from Arabidopsis thaliana |
| **SEQ ID NO:11** | full-length sequence of the CL22 gene from Arabidopsis thaliana |
| **SEQ ID NO:12** | full-length sequence of the CL22 gene from Arabidopsis thaliana, variant 1 |
| **SEQ ID NO:13** | full-length sequence of the CL22 gene from Arabidopsis thaliana, variant 2 |
| **SEQ ID NO:14** | sequence of the CL22 protein from Arabidopsis thaliana |
| **SEQ ID NO:15** | sequence of the CL22 protein from Arabidopsis thaliana, variant 1 |
| **SEQ ID NO:16** | sequence of the CL22 protein from Arabidopsis thaliana, variant 2 |
| **SEQ ID NO:17** | full-length sequence of the CL19 gene from Arabidopsis thaliana |
| **SEQ ID NO:18** | sequence of the CL19 protein from Arabidopsis thaliana |
| **SEQ ID NO:19** | full-length sequence of the CL20 gene from Arabidopsis thaliana |
| **SEQ ID NO:20** | sequence of the CL20 protein from Arabidopsis thaliana |
| **SEQ ID NO:21** | full-length sequence of the CL14 gene from Arabidopsis thaliana |
| **SEQ ID NO:22** | sequence of the CL14 protein from Arabidopsis thaliana |
| **SEQ ID NO:23** | full-length sequence of the CL11 gene from Arabidopsis thaliana |
| **SEQ ID NO:24** | sequence of the CL11 protein from Arabidopsis thaliana |
| **SEQ ID NO:25** | full-length sequence of the CL8 gene from Arabidopsis thaliana |

| Figure 12 | |
|---|---|
| **SEQ ID NO:** | **Description of the sequence listing** |
| **SEQ ID NO:26** | sequence of the CL8 protein from Arabidopsis thaliana |
| **SEQ ID NO:27** | full-length sequence of the CL16 gene from Arabidopsis thaliana |
| **SEQ ID NO:28** | sequence of the CL16 protein from Arabidopsis thaliana |
| **SEQ ID NO:29** | full-length sequence of the CL10 gene from Arabidopsis thaliana |
| **SEQ ID NO:30** | sequence of the CL10 protein from Arabidopsis thaliana |
| **SEQ ID NO:31** | full-length sequence of the CL15 gene from Arabidopsis thaliana |
| **SEQ ID NO:32** | sequence of the CL15 protein from Arabidopsis thaliana |
| **SEQ ID NO:33** | full-length sequence of the CL3 gene from Arabidopsis thaliana |
| **SEQ ID NO:34** | sequence of the CL3 protein from Arabidopsis thaliana |
| **SEQ ID NO:35** | full-length sequence of the CL2 gene from Arabidopsis thaliana |
| **SEQ ID NO:36** | sequence of the CL2 protein from Arabidopsis thaliana |
| **SEQ ID NO:37** | full-length sequence of the CL21 gene from Arabidopsis thaliana |
| **SEQ ID NO:38** | sequence of the CL21 protein from Arabidopsis thaliana |
| **SEQ ID NO:39** | full-length sequence of the CL23 gene from Arabidopsis thaliana |
| **SEQ ID NO:40** | sequence of the CL23 protein from Arabidopsis thaliana |
| **SEQ ID NO:41** | full-length sequence of the CL9 gene from Arabidopsis thaliana |
| **SEQ ID NO:42** | sequence of the CL9 protein from Arabidopsis thaliana |
| **SEQ ID NO:43** | full-length sequence of the CL24 gene from Arabidopsis thaliana |
| **SEQ ID NO:44** | sequence of the CL24 protein from Arabidopsis thaliana |
| **SEQ ID NO:45** | full-length sequence of the CL25 gene from Arabidopsis thaliana |
| **SEQ ID NO:46** | sequence of the CL25 protein from Arabidopsis thaliana |
| **SEQ ID NO:47** | full-length sequence of the CL6 gene from Arabidopsis thaliana |
| **SEQ ID NO:48** | sequence of the CL6 protein from Arabidopsis thaliana |
| **SEQ ID NO:49** | full-length sequence of the CL5 gene from Arabidopsis thaliana |
| **SEQ ID NO:50** | full-length sequence of the CL5 gene from Arabidopsis thaliana, variant |
| **SEQ ID NO:51** | sequence of the CL5 protein from Arabidopsis thaliana |

| **Figure 12** | |
|---|---|
| **SEQ ID NO:** | **Description of the sequence listing** |
| **SEQ ID NO:52** | sequence of the CL5 protein from Arabidopsis thaliana, variant |
| **SEQ ID NO:53** | full-length sequence of the CL7 gene from Arabidopsis thaliana |
| **SEQ ID NO:54** | sequence of the CL7 protein from Arabidopsis thaliana |
| **SEQ ID NO:55** | full-length sequence of the CL12 gene from Arabidopsis thaliana |
| **SEQ ID NO:56** | sequence of the CL12 protein from Arabidopsis thaliana |
| **SEQ ID NO:57** | full-length sequence of the CL18 gene from Arabidopsis thaliana |
| **SEQ ID NO:58** | sequence of the CL18 protein from Arabidopsis thaliana |
| **SEQ ID NO:59** | full-length sequence of the GLP9 gene from Arabidopsis thaliana |
| **SEQ ID NO:60** | sequence of the GLP9 protein from Arabidopsis thaliana |

SEQUENCE LISTING

```
<160> NUMBER OF SEQ ID NOS: 96

<210> SEQ ID NO 1
<211> LENGTH: 267
<212> TYPE: DNA
<213> ORGANISM: Arabidopsis thaliana

<400> SEQUENCE: 1

atggtacttg gaaactcctc cagtcacaaa tctcatcacc atcaacatca taatcatcat      60

caccgggact cgatgaagga gttccgagct gtctttgcag ccgaagaacc aatccagggc     120

ttcgagtatg cagatatgag gaggtcaaag agcgagaata tgggcactag agaggttgca     180

aaagcagagg atgttgacaa agaagctgag caattcatca agtttgagca tacgaagttc     240

agtaagtgga tgactaagag cgcctag                                         267


<210> SEQ ID NO 2
<211> LENGTH: 88
<212> TYPE: PRT
<213> ORGANISM: Arabidopsis thaliana

<400> SEQUENCE: 2

Met Val Leu Gly Asn Ser Ser Ser His Lys Ser His His His Gln His
1               5                   10                  15

His Asn His His His Arg Asp Ser Met Lys Glu Phe Arg Ala Val Phe
            20                  25                  30

Ala Ala Glu Glu Pro Ile Gln Gly Phe Glu Tyr Ala Asp Met Arg Arg
        35                  40                  45

Ser Lys Ser Glu Asn Met Gly Thr Arg Glu Val Ala Lys Ala Glu Asp
    50                  55                  60

Val Asp Lys Glu Ala Glu Gln Phe Ile Lys Phe Glu His Thr Lys Phe
65                  70                  75                  80

Ser Lys Trp Met Thr Lys Ser Ala
                85


<210> SEQ ID NO 3
<211> LENGTH: 918
<212> TYPE: DNA
<213> ORGANISM: Arabidopsis thaliana

<400> SEQUENCE: 3

atgaacaagg gtggagctca acagaaaggt cattcgtcaa agcaagctga aaacatagtt      60

ttagtaggcc ggacagggaa tggaaaaagt gcgacaggta acagcctcat tggaaaaaag     120
```

```
gtgtttgctt caaaggcaca tgcttctggt gtgaccatga aatgtcagac acatggagtt    180

gtgacaaaag atggtcacaa aatcaatgtg attgatactc cagtgtcggc tgagtatata    240

agtaaagaga ttgttagatg tctaactcta gcagaaggag ggatacatgc tgtgctctta    300

gttttatctg caaggactcg aattactcaa gaggaagaga acacacttag aaccttacag    360

gctctatttg ggagtcaaat tcttgattat gtcgtcgttg ttttcaccgg tggtgacgtg    420

ctagaagagt gcaaggagac actagaagat tatttgggta gagattgccc tactttcata    480

aaggaagtga tgaggatgtc tagtaaccga aaggttgtga tcgataacaa gactcatgat    540

gaaggcaaaa aagcagagca agtccataag cttctctccc tagtagatga tatcagaagg    600

agcaagtgtg gagaagcata taccgatgat acatatcata tgataaagga agagtcagag    660

aaactaagga agcatcatga ggagctggaa tcaaagaact attcagaaga atgtgcagct    720

gaaatgaaga atcagtcact tatattgtat aaggagaatt tgaaacaaat gtcagagcag    780

ttggagaaga agctcaaaga tgctgcggag gcgcaagaaa aagcgctaag caagatgaca    840

caagaaaaca acgagctgaa cctggcgctt aagattcaca tcccgttgcc gccaattact    900

ccatgcaaca ttctttga                                                  918
```

<210> SEQ ID NO 4
<211> LENGTH: 936
<212> TYPE: DNA
<213> ORGANISM: Arabidopsis thaliana

<400> SEQUENCE: 4

```
atgaacaagg gtggagctca acagaaaggt cattcgtcaa agcaagctga aaacatagtt     60

ttagtaggcc ggacagggaa tggaaaaagt gcgacaggta acagcctcat tggaaaaaag    120

gtgtttgctt caaaggcaca tgcttctggt gtgaccatga aatgtcagac acatggagtt    180

gtgacaaaag atggtcacaa aatcaatgtg attgatactc caggtctgtt tgacttgtca    240

gtgtcggctg agtatataag taaagagatt gttagatgtc taactctagc agaaggaggg    300

atacatgctg tgctcttagt tttatctgca aggactcgaa ttactcaaga ggaagagaac    360

acacttagaa ccttacaggc tctatttggg agtcaaattc ttgattatgt cgtcgttgtt    420

ttcaccggtg gtgacgtgct agaagagtgc aaggagacac tagaagatta tttgggtaga    480

gattgcccta ctttcataaa ggaagtgatg aggatgtcta gtaaccgaaa ggttgtgatc    540

gataacaaga ctcatgatga aggcaaaaaa gcagagcaag tccataagct tctctcccta    600

gtagatgata tcagaaggag caagtgtgga gaagcatata ccgatgatac atatcatatg    660

ataaaggaag agtcagagaa actaaggaag catcatgagg agctggaatc aaagaactat    720

tcagaagaat gtgcagctga aatgaagaat cagtcactta tattgtataa ggagaatttg    780

aaacaaatgt cagagcagtt ggagaagaag ctcaaagatg ctgcggaggc gcaagaaaaa    840

gcgctaagca agatgacaca agaaaacaac gagctgaacc tggcgcttaa gattcacatc    900

ccgttgccgc caattactcc atgcaacatt ctttga                              936
```

<210> SEQ ID NO 5
<211> LENGTH: 305
<212> TYPE: PRT
<213> ORGANISM: Arabidopsis thaliana

<400> SEQUENCE: 5

```
Met Asn Lys Gly Gly Ala Gln Gln Lys Gly His Ser Ser Lys Gln Ala
1               5                   10                  15
```

```
Glu Asn Ile Val Leu Val Gly Arg Thr Gly Asn Gly Lys Ser Ala Thr
            20                  25                  30

Gly Asn Ser Leu Ile Gly Lys Lys Val Phe Ala Ser Lys Ala His Ala
        35                  40                  45

Ser Gly Val Thr Met Lys Cys Gln Thr His Gly Val Val Thr Lys Asp
    50                  55                  60

Gly His Lys Ile Asn Val Ile Asp Thr Pro Val Ser Ala Glu Tyr Ile
65                  70                  75                  80

Ser Lys Glu Ile Val Arg Cys Leu Thr Leu Ala Glu Gly Gly Ile His
                85                  90                  95

Ala Val Leu Leu Val Leu Ser Ala Arg Thr Arg Ile Thr Gln Glu Glu
            100                 105                 110

Glu Asn Thr Leu Arg Thr Leu Gln Ala Leu Phe Gly Ser Gln Ile Leu
        115                 120                 125

Asp Tyr Val Val Val Val Phe Thr Gly Gly Asp Val Leu Glu Glu Cys
    130                 135                 140

Lys Glu Thr Leu Glu Asp Tyr Leu Gly Arg Asp Cys Pro Thr Phe Ile
145                 150                 155                 160

Lys Glu Val Met Arg Met Ser Ser Asn Arg Lys Val Val Ile Asp Asn
                165                 170                 175

Lys Thr His Asp Glu Gly Lys Lys Ala Glu Gln Val His Lys Leu Leu
            180                 185                 190

Ser Leu Val Asp Asp Ile Arg Arg Ser Lys Cys Gly Glu Ala Tyr Thr
        195                 200                 205

Asp Asp Thr Tyr His Met Ile Lys Glu Glu Ser Glu Lys Leu Arg Lys
    210                 215                 220

His His Glu Glu Leu Glu Ser Lys Asn Tyr Ser Glu Glu Cys Ala Ala
225                 230                 235                 240

Glu Met Lys Asn Gln Ser Leu Ile Leu Tyr Lys Glu Asn Leu Lys Gln
                245                 250                 255

Met Ser Glu Gln Leu Glu Lys Lys Leu Lys Asp Ala Ala Glu Ala Gln
            260                 265                 270

Glu Lys Ala Leu Ser Lys Met Thr Gln Glu Asn Asn Glu Leu Asn Leu
        275                 280                 285

Ala Leu Lys Ile His Ile Pro Leu Pro Pro Ile Thr Pro Cys Asn Ile
    290                 295                 300

Leu
305
```

<210> SEQ ID NO 6
<211> LENGTH: 311
<212> TYPE: PRT
<213> ORGANISM: Arabidopsis thaliana

<400> SEQUENCE: 6

```
Met Asn Lys Gly Gly Ala Gln Gln Lys Gly His Ser Ser Lys Gln Ala
1               5                   10                  15

Glu Asn Ile Val Leu Val Gly Arg Thr Gly Asn Gly Lys Ser Ala Thr
            20                  25                  30

Gly Asn Ser Leu Ile Gly Lys Lys Val Phe Ala Ser Lys Ala His Ala
        35                  40                  45

Ser Gly Val Thr Met Lys Cys Gln Thr His Gly Val Val Thr Lys Asp
    50                  55                  60

Gly His Lys Ile Asn Val Ile Asp Thr Pro Gly Leu Phe Asp Leu Ser
```

-continued 65 70 75 80

Val Ser Ala Glu Tyr Ile Ser Lys Glu Ile Val Arg Cys Leu Thr Leu
85 90 95

Ala Glu Gly Gly Ile His Ala Val Leu Leu Val Leu Ser Ala Arg Thr
100 105 110

Arg Ile Thr Gln Glu Glu Glu Asn Thr Leu Arg Thr Leu Gln Ala Leu
115 120 125

Phe Gly Ser Gln Ile Leu Asp Tyr Val Val Val Val Phe Thr Gly Gly
130 135 140

Asp Val Leu Glu Glu Cys Lys Glu Thr Leu Glu Asp Tyr Leu Gly Arg
145 150 155 160

Asp Cys Pro Thr Phe Ile Lys Glu Val Met Arg Met Ser Ser Asn Arg
165 170 175

Lys Val Val Ile Asp Asn Lys Thr His Asp Glu Gly Lys Lys Ala Glu
180 185 190

Gln Val His Lys Leu Leu Ser Leu Val Asp Asp Ile Arg Arg Ser Lys
195 200 205

Cys Gly Glu Ala Tyr Thr Asp Asp Thr Tyr His Met Ile Lys Glu Glu
210 215 220

Ser Glu Lys Leu Arg Lys His His Glu Glu Leu Glu Ser Lys Asn Tyr
225 230 235 240

Ser Glu Glu Cys Ala Ala Glu Met Lys Asn Gln Ser Leu Ile Leu Tyr
245 250 255

Lys Glu Asn Leu Lys Gln Met Ser Glu Gln Leu Glu Lys Lys Leu Lys
260 265 270

Asp Ala Ala Glu Ala Gln Glu Lys Ala Leu Ser Lys Met Thr Gln Glu
275 280 285

Asn Asn Glu Leu Asn Leu Ala Leu Lys Ile His Ile Pro Leu Pro Pro
290 295 300

Ile Thr Pro Cys Asn Ile Leu
305 310

<210> SEQ ID NO 7
<211> LENGTH: 2673
<212> TYPE: DNA
<213> ORGANISM: Arabidopsis thaliana

<400> SEQUENCE: 7
atgaaatctc ttcactggtt tttgcatctt ttgatcatag cttttaccgt tttgagatca 60
gtggaagctc aaaatcaagc aggatttatt agtttggatt gtgggttggt gcctaaggaa 120
actacttata cagagaagtc gacgaatata acatacaaat cagacgtgga ttacatcgac 180
agtggattgg tcggaaagat caatgatgca tacaaaactc agtttcagca acaggtttgg 240
gccgtgagaa gcttccctgt aggtcaaaga aactgttaca atgtcaacct cacggcaaac 300
aacaaatatt tgatcagagg aacctttgtg tatgggaatt atgatggcct gaatcagttc 360
ccaagttttg atcttcatat cggtcctaac aaatggtcgt ctgttaaaat actaggagta 420
acaaatactt ctatgcatga gataatccat gtcgtaccac aagatagtct tgaagtttgt 480
cttgttaaga ctggaccgac gacaccattc atttcgtcgc tggaggttcg tccattgaac 540
aatgaaagtt atctcacgca aagtggatca ttgatgttgt tcgccagagt atactttcca 600
tccagttcat catctttcat taggtatgat gaggacatac atgaccgtgt ttggaattca 660
ttcacagatg atgaaaccgt ctggataagt acagacctcc cgatcgatac aagtaactcc 720

```
tatgacatgc ctcaatccgt gatgaagaca gctgctgtcc ctaaaaatgc tagtgagcca    780
tggctcttat ggtggactct tgatgagaac accgcacaat catatgtata tatgcatttc    840
gccgaagtcc agaatcttac agcaaatgaa accagagaat tcaacattac ttacaatggt    900
ggtctacgtt ggttcagcta tttgaggcct cctaatctca gcatttcaac gatctttaat    960
ccaagggcag tgagttcttc aaatgggata tttaatttca cattcgcaat gacgggtaac   1020
tcaactctgc ctccccttct caacgccctc gagatttata cagtcgtaga cattctacag   1080
ctagagacaa acaaagatga agtttctgct atgatgaaca tcaaagaaac atatggttta   1140
agcaaaaaga taagctggca aggagatccg tgtgctcctc agctttatcg gtgggaaggt   1200
ttaaattgta gttatccgga ctccgaggga tcaagaatca tatccttgaa cttgaatggg   1260
agcgagttga caggttctat aacatctgac atatccaagc taacactgtt gacagtatta   1320
gatttatcaa ataatgattt atcaggagat attccaacat tttttgctga gatgaagtcg   1380
ttgaaactca taaacttaag tggaaacccg aaccttaatc tcacagcaat tccagactct   1440
cttcagcaaa gggtaaacag caaatcttta acactaattt tgggtgaaaa cctgactctg   1500
actcccaaaa aagagagtaa aaaggttccc atggttgcta tcgcagcgtc agtggctggc   1560
gtgttcgctc tgctcgttat cttagccata ttttttgtca ttaaaaggaa aaatgtgaaa   1620
gctcataagt ctccaggacc acccccatta gtcactcccg gtatagttaa aagtgagaca   1680
agatcatcca atccatcaat cataacaagg gaacgcaaga tcacgtatcc agaggtactg   1740
aagatgacta ataacttcga gagagttctt ggcaaaggag gctttggaac agtgtatcat   1800
ggaaacttgg atggtgctga agtggcagtg aaaatgcttt ctcattcatc agctcaaggt   1860
tataaagagt tcaaagcaga ggttgaactt cttttaagag ttcaccatag acatttggtg   1920
ggacttgtgg gttactgtga tgatggagac aacttggctc tgatttatga atatatggca   1980
aatggagacc tgagggagaa tatgtcagga aaacgtggag gcaatgtcct tacctgggaa   2040
aacaggatgc aaatagctgt agaggctgca caagggctgg agtatctgca caatggatgt   2100
aggcctccta tggtacatag agatgttaaa actactaaca ttttattgaa tgagcggtgt   2160
ggagcaaaac tagccgactt tgggctctcg agatctttcc caatcgatgg cgaatgtcat   2220
gtttcgacag tggttgcggg tacacctggt tacctagacc cggagtacta cagaacaaac   2280
tggctaagcg agaagagtga cgtgtacagc ttcggtgtag tgctattaga gatagtcaca   2340
aaccagcctg tgatagataa aacccgggag agacctcaca tcaatgactg ggttgggttc   2400
atgctcacta aaggagacat caagagcatc gttgacccga aactgatggg ggactatgat   2460
acaaacggtg catggaagat tgtggagcta gctctggcct gtgtgaaccc atcttcgaac   2520
cggagaccaa caatggcaca cgttgtgatg gagctaaacg actgtgtggc cttagaaaat   2580
gcaaggcggc aaggtagtga agagatgtac tcaatgggtt ctgttgacta tagtctctct   2640
tctacttctg actttgctcc tggagccaga taa                                2673
```

<210> SEQ ID NO 8
<211> LENGTH: 890
<212> TYPE: PRT
<213> ORGANISM: Arabidopsis thaliana

<400> SEQUENCE: 8

```
Met Lys Ser Leu His Trp Phe Leu His Leu Leu Ile Ile Ala Phe Thr
1               5                   10                  15

Val Leu Arg Ser Val Glu Ala Gln Asn Gln Ala Gly Phe Ile Ser Leu
            20                  25                  30
```

-continued

```
Asp Cys Gly Leu Val Pro Lys Glu Thr Thr Tyr Thr Glu Lys Ser Thr
        35                  40                  45

Asn Ile Thr Tyr Lys Ser Asp Val Asp Tyr Ile Asp Ser Gly Leu Val
    50                  55                  60

Gly Lys Ile Asn Asp Ala Tyr Lys Thr Gln Phe Gln Gln Gln Val Trp
65                  70                  75                  80

Ala Val Arg Ser Phe Pro Val Gly Gln Arg Asn Cys Tyr Asn Val Asn
                85                  90                  95

Leu Thr Ala Asn Asn Lys Tyr Leu Ile Arg Gly Thr Phe Val Tyr Gly
            100                 105                 110

Asn Tyr Asp Gly Leu Asn Gln Phe Pro Ser Phe Asp Leu His Ile Gly
        115                 120                 125

Pro Asn Lys Trp Ser Ser Val Lys Ile Leu Gly Val Thr Asn Thr Ser
    130                 135                 140

Met His Glu Ile Ile His Val Val Pro Gln Asp Ser Leu Glu Val Cys
145                 150                 155                 160

Leu Val Lys Thr Gly Pro Thr Thr Pro Phe Ile Ser Ser Leu Glu Val
                165                 170                 175

Arg Pro Leu Asn Asn Glu Ser Tyr Leu Thr Gln Ser Gly Ser Leu Met
            180                 185                 190

Leu Phe Ala Arg Val Tyr Phe Pro Ser Ser Ser Ser Ser Phe Ile Arg
        195                 200                 205

Tyr Asp Glu Asp Ile His Asp Arg Val Trp Asn Ser Phe Thr Asp Asp
    210                 215                 220

Glu Thr Val Trp Ile Ser Thr Asp Leu Pro Ile Asp Thr Ser Asn Ser
225                 230                 235                 240

Tyr Asp Met Pro Gln Ser Val Met Lys Thr Ala Ala Val Pro Lys Asn
                245                 250                 255

Ala Ser Glu Pro Trp Leu Leu Trp Trp Thr Leu Asp Glu Asn Thr Ala
            260                 265                 270

Gln Ser Tyr Val Tyr Met His Phe Ala Glu Val Gln Asn Leu Thr Ala
        275                 280                 285

Asn Glu Thr Arg Glu Phe Asn Ile Thr Tyr Asn Gly Gly Leu Arg Trp
    290                 295                 300

Phe Ser Tyr Leu Arg Pro Pro Asn Leu Ser Ile Ser Thr Ile Phe Asn
305                 310                 315                 320

Pro Arg Ala Val Ser Ser Ser Asn Gly Ile Phe Asn Phe Thr Phe Ala
                325                 330                 335

Met Thr Gly Asn Ser Thr Leu Pro Pro Leu Leu Asn Ala Leu Glu Ile
            340                 345                 350

Tyr Thr Val Val Asp Ile Leu Gln Leu Glu Thr Asn Lys Asp Glu Val
        355                 360                 365

Ser Ala Met Met Asn Ile Lys Glu Thr Tyr Gly Leu Ser Lys Lys Ile
    370                 375                 380

Ser Trp Gln Gly Asp Pro Cys Ala Pro Gln Leu Tyr Arg Trp Glu Gly
385                 390                 395                 400

Leu Asn Cys Ser Tyr Pro Asp Ser Glu Gly Ser Arg Ile Ile Ser Leu
                405                 410                 415

Asn Leu Asn Gly Ser Glu Leu Thr Gly Ser Ile Thr Ser Asp Ile Ser
            420                 425                 430

Lys Leu Thr Leu Leu Thr Val Leu Asp Leu Ser Asn Asn Asp Leu Ser
        435                 440                 445
```

-continued

```
Gly Asp Ile Pro Thr Phe Phe Ala Glu Met Lys Ser Leu Lys Leu Ile
    450                 455                 460

Asn Leu Ser Gly Asn Pro Asn Leu Asn Leu Thr Ala Ile Pro Asp Ser
465                 470                 475                 480

Leu Gln Gln Arg Val Asn Ser Lys Ser Leu Thr Leu Ile Leu Gly Glu
                485                 490                 495

Asn Leu Thr Leu Thr Pro Lys Lys Glu Ser Lys Lys Val Pro Met Val
            500                 505                 510

Ala Ile Ala Ala Ser Val Ala Gly Val Phe Ala Leu Leu Val Ile Leu
        515                 520                 525

Ala Ile Phe Phe Val Ile Lys Arg Lys Asn Val Lys Ala His Lys Ser
    530                 535                 540

Pro Gly Pro Pro Pro Leu Val Thr Pro Gly Ile Val Lys Ser Glu Thr
545                 550                 555                 560

Arg Ser Ser Asn Pro Ser Ile Ile Thr Arg Glu Arg Lys Ile Thr Tyr
                565                 570                 575

Pro Glu Val Leu Lys Met Thr Asn Asn Phe Glu Arg Val Leu Gly Lys
            580                 585                 590

Gly Gly Phe Gly Thr Val Tyr His Gly Asn Leu Asp Gly Ala Glu Val
        595                 600                 605

Ala Val Lys Met Leu Ser His Ser Ser Ala Gln Gly Tyr Lys Glu Phe
    610                 615                 620

Lys Ala Glu Val Glu Leu Leu Leu Arg Val His His Arg His Leu Val
625                 630                 635                 640

Gly Leu Val Gly Tyr Cys Asp Asp Gly Asp Asn Leu Ala Leu Ile Tyr
                645                 650                 655

Glu Tyr Met Ala Asn Gly Asp Leu Arg Glu Asn Met Ser Gly Lys Arg
            660                 665                 670

Gly Gly Asn Val Leu Thr Trp Glu Asn Arg Met Gln Ile Ala Val Glu
        675                 680                 685

Ala Ala Gln Gly Leu Glu Tyr Leu His Asn Gly Cys Arg Pro Pro Met
    690                 695                 700

Val His Arg Asp Val Lys Thr Thr Asn Ile Leu Leu Asn Glu Arg Cys
705                 710                 715                 720

Gly Ala Lys Leu Ala Asp Phe Gly Leu Ser Arg Ser Phe Pro Ile Asp
                725                 730                 735

Gly Glu Cys His Val Ser Thr Val Val Ala Gly Thr Pro Gly Tyr Leu
            740                 745                 750

Asp Pro Glu Tyr Tyr Arg Thr Asn Trp Leu Ser Glu Lys Ser Asp Val
        755                 760                 765

Tyr Ser Phe Gly Val Val Leu Leu Glu Ile Val Thr Asn Gln Pro Val
    770                 775                 780

Ile Asp Lys Thr Arg Glu Arg Pro His Ile Asn Asp Trp Val Gly Phe
785                 790                 795                 800

Met Leu Thr Lys Gly Asp Ile Lys Ser Ile Val Asp Pro Lys Leu Met
                805                 810                 815

Gly Asp Tyr Asp Thr Asn Gly Ala Trp Lys Ile Val Glu Leu Ala Leu
            820                 825                 830

Ala Cys Val Asn Pro Ser Ser Asn Arg Arg Pro Thr Met Ala His Val
        835                 840                 845

Val Met Glu Leu Asn Asp Cys Val Ala Leu Glu Asn Ala Arg Arg Gln
    850                 855                 860

Gly Ser Glu Glu Met Tyr Ser Met Gly Ser Val Asp Tyr Ser Leu Ser
```

-continued 865 870 875 880

Ser Thr Ser Asp Phe Ala Pro Gly Ala Arg
885 890

<210> SEQ ID NO 9
<211> LENGTH: 1998
<212> TYPE: DNA
<213> ORGANISM: Arabidopsis thaliana

<400> SEQUENCE: 9
atggcgactg gtcgatacat cgttgaggtt gagaagggaa agcaaggcgt tgatggagga 60
agtccatcgg tcggtccagt gtaccggagt atctatgcta aagacggttt tcctgaaccg 120
cctgatgatc tcgtcagtgc atgggatatt ttccgtttat ctgtggagaa atctccaaat 180
aatcctatgc ttggtcgtag agaaatagtt gatggaaaag ctgggaaata tgtatggcaa 240
acttacaaag aagtacataa tgtagtgatt aagcttggaa actctatcag aactattgga 300
gttggaaaag gagataaatg cggtatttat ggcgccaata gtcctgaatg gattataagc 360
atggaggctt gcaatgctca tggactctac tgtgtacctt tatatgacac tctaggtgct 420
ggagcaatag aattcatcat ttgtcatgct gaggtctcac ttgcttttgc tgaggagaac 480
aagatttctg agttattgaa gacagctcca aaatcaacta aatatttgaa gtatattgtg 540
agctttggtg aggttacaaa taatcagaga gtagaagctg agaggcacag attaacaata 600
tattcatggg accaattctt gaagctaggc gagggtaaac attatgaatt accagagaag 660
aggagaagcg atgtttgcac cataatgtat acaagtggca caactggtga tcctaaagga 720
gtattgctta caaatgagag cattattcat ctccttgaag gtgttaaaaa attgcttaaa 780
actattgatg aagagttaac cagtaaagat gtatatctct catatctacc tctggctcat 840
atcttcgatc gtgtgattga ggagctgtgt atttatgaag cagcctctat cggattctgg 900
cgaggggatg ttaagatatt gatagaagac attgctgcat tgaaaccgac tgttttctgc 960
gctgttcctc gcgttctaga gagaatatac accggtcttc agcagaaact ttctgatggt 1020
ggttttgtaa agaagaaatt attcaacttt gcattcaaat acaaacataa aaacatggag 1080
aaagggcagc ctcatgaaca agcatctcca atagctgaca aaattgtatt taaaaaggta 1140
aaagaagggt tgggaggaaa cgtgcgtctt atcctctcag gagcagctcc tcttgcagct 1200
cacatcgaat ctttccttcg agttgtcgcg tgtgctcatg ttttgcaagg atacggtcta 1260
acagagagtt gtggtgggac ttttgtgtcc attccaaacg agctttcaat gcttggaacg 1320
gttggtccac cggttccaaa cgttgacata aggctagagt cagttccaga gatgggttat 1380
gacgctcttg caagcaatcc acgtggagag atttgcatca ggggaaagac tttgttctct 1440
ggatactaca aacgtgaaga tctcactcaa gaagtcttca ttgatggatg gcttcacact 1500
ggtgatgtcg gtgagtggca accagatgga gccatgaaga tcatcgaccg taagaagaac 1560
atctttaaac tgtctcaagg agaatacgtt gccgttgaga acttggagaa catatacagt 1620
catgtcgccg ccattgaatc gatatgggta tatggaaaca gctatgagtc ttacttagtg 1680
gctgtggtat gtccaagcaa gatccagatc gagcattggg ccaaagaaca caaagtttca 1740
ggagactttg agtctatctg ccgaaaccaa aagactaaag agtttgtcct tggagagttc 1800
aacagagtag ccaaagacaa aaagctgaag ggatttgagc tgatcaaagg tgttcatttg 1860
gacacagtcc cgttcgacat ggaaagagat ctcatcactc cttcttacaa gatgaaaaga 1920
cctcagcttc tcaagtacta tcagaaagag attgatgaaa tgtataagaa aaacagagaa 1980

-continued gtgcagctac gagtgtaa 1998

<210> SEQ ID NO 10
<211> LENGTH: 665
<212> TYPE: PRT
<213> ORGANISM: Arabidopsis thaliana

<400> SEQUENCE: 10

Met Ala Thr Gly Arg Tyr Ile Val Glu Val Glu Lys Gly Lys Gln Gly
1 5 10 15

Val Asp Gly Gly Ser Pro Ser Val Gly Pro Val Tyr Arg Ser Ile Tyr
20 25 30

Ala Lys Asp Gly Phe Pro Glu Pro Pro Asp Asp Leu Val Ser Ala Trp
35 40 45

Asp Ile Phe Arg Leu Ser Val Glu Lys Ser Pro Asn Asn Pro Met Leu
50 55 60

Gly Arg Arg Glu Ile Val Asp Gly Lys Ala Gly Lys Tyr Val Trp Gln
65 70 75 80

Thr Tyr Lys Glu Val His Asn Val Val Ile Lys Leu Gly Asn Ser Ile
85 90 95

Arg Thr Ile Gly Val Gly Lys Gly Asp Lys Cys Gly Ile Tyr Gly Ala
100 105 110

Asn Ser Pro Glu Trp Ile Ile Ser Met Glu Ala Cys Asn Ala His Gly
115 120 125

Leu Tyr Cys Val Pro Leu Tyr Asp Thr Leu Gly Ala Gly Ala Ile Glu
130 135 140

Phe Ile Ile Cys His Ala Glu Val Ser Leu Ala Phe Ala Glu Glu Asn
145 150 155 160

Lys Ile Ser Glu Leu Leu Lys Thr Ala Pro Lys Ser Thr Lys Tyr Leu
165 170 175

Lys Tyr Ile Val Ser Phe Gly Glu Val Thr Asn Asn Gln Arg Val Glu
180 185 190

Ala Glu Arg His Arg Leu Thr Ile Tyr Ser Trp Asp Gln Phe Leu Lys
195 200 205

Leu Gly Glu Gly Lys His Tyr Glu Leu Pro Glu Lys Arg Arg Ser Asp
210 215 220

Val Cys Thr Ile Met Tyr Thr Ser Gly Thr Thr Gly Asp Pro Lys Gly
225 230 235 240

Val Leu Leu Thr Asn Glu Ser Ile Ile His Leu Leu Glu Gly Val Lys
245 250 255

Lys Leu Leu Lys Thr Ile Asp Glu Glu Leu Thr Ser Lys Asp Val Tyr
260 265 270

Leu Ser Tyr Leu Pro Leu Ala His Ile Phe Asp Arg Val Ile Glu Glu
275 280 285

Leu Cys Ile Tyr Glu Ala Ala Ser Ile Gly Phe Trp Arg Gly Asp Val
290 295 300

Lys Ile Leu Ile Glu Asp Ile Ala Ala Leu Lys Pro Thr Val Phe Cys
305 310 315 320

Ala Val Pro Arg Val Leu Glu Arg Ile Tyr Thr Gly Leu Gln Gln Lys
325 330 335

Leu Ser Asp Gly Gly Phe Val Lys Lys Lys Leu Phe Asn Phe Ala Phe
340 345 350

Lys Tyr Lys His Lys Asn Met Glu Lys Gly Gln Pro His Glu Gln Ala
355 360 365

-continued

```
Ser Pro Ile Ala Asp Lys Ile Val Phe Lys Lys Val Lys Glu Gly Leu
    370                 375                 380

Gly Gly Asn Val Arg Leu Ile Leu Ser Gly Ala Ala Pro Leu Ala Ala
385                 390                 395                 400

His Ile Glu Ser Phe Leu Arg Val Val Ala Cys Ala His Val Leu Gln
                405                 410                 415

Gly Tyr Gly Leu Thr Glu Ser Cys Gly Gly Thr Phe Val Ser Ile Pro
            420                 425                 430

Asn Glu Leu Ser Met Leu Gly Thr Val Gly Pro Pro Val Pro Asn Val
        435                 440                 445

Asp Ile Arg Leu Glu Ser Val Pro Glu Met Gly Tyr Asp Ala Leu Ala
    450                 455                 460

Ser Asn Pro Arg Gly Glu Ile Cys Ile Arg Gly Lys Thr Leu Phe Ser
465                 470                 475                 480

Gly Tyr Tyr Lys Arg Glu Asp Leu Thr Gln Glu Val Phe Ile Asp Gly
                485                 490                 495

Trp Leu His Thr Gly Asp Val Gly Glu Trp Gln Pro Asp Gly Ala Met
            500                 505                 510

Lys Ile Ile Asp Arg Lys Lys Asn Ile Phe Lys Leu Ser Gln Gly Glu
        515                 520                 525

Tyr Val Ala Val Glu Asn Leu Glu Asn Ile Tyr Ser His Val Ala Ala
    530                 535                 540

Ile Glu Ser Ile Trp Val Tyr Gly Asn Ser Tyr Glu Ser Tyr Leu Val
545                 550                 555                 560

Ala Val Val Cys Pro Ser Lys Ile Gln Ile Glu His Trp Ala Lys Glu
                565                 570                 575

His Lys Val Ser Gly Asp Phe Glu Ser Ile Cys Arg Asn Gln Lys Thr
            580                 585                 590

Lys Glu Phe Val Leu Gly Glu Phe Asn Arg Val Ala Lys Asp Lys Lys
        595                 600                 605

Leu Lys Gly Phe Glu Leu Ile Lys Gly Val His Leu Asp Thr Val Pro
    610                 615                 620

Phe Asp Met Glu Arg Asp Leu Ile Thr Pro Ser Tyr Lys Met Lys Arg
625                 630                 635                 640

Pro Gln Leu Leu Lys Tyr Tyr Gln Lys Glu Ile Asp Glu Met Tyr Lys
                645                 650                 655

Lys Asn Arg Glu Val Gln Leu Arg Val
            660                 665
```

<210> SEQ ID NO 11
<211> LENGTH: 882
<212> TYPE: DNA
<213> ORGANISM: Arabidopsis thaliana

<400> SEQUENCE: 11

```
atgaagaaga cgccagttcc agaagcgaac aaatctttac actctttatc gtctgatgga      60

atctctattg acctcaacgg tcagaatgat tcttttaacc ataagcagga gaagccatcg     120

cgaactgttc ctctatcccc aaacagcatg gctgatcgtg ggaaaccctt atcaccacga     180

cctcaagggc atgaacacag tggcaagaat gacacagcca gtgagattag tttgtttaat     240

gttgtaagcc ctccaagatc atgcgccaat gatgatgatg atgatgatga tgaaaacaat     300

ggttacgagg agggagtgga gttagacctt atatcagtaa tgtcagactc atgtgtttcg     360

gttggaaaat accgtgtgaa ctcaagtgtt tccacaatcc tacagtcaat cattgataaa     420
```

-continued

```
cacggagaca tagcagcaaa ctgcaagcta gaatcagcat caatgcgatc ccgataccta    480

gagtgtctat gctcattgat gcaagaactt ggatcaaccc cggtgggtca gttaaccgaa    540

ctaaaagtaa aagagatggt cgcggttctc aaggacttgg agtctgtgaa catcgacgtt    600

ggctggatgc gttcggttct tgaggagttt gctcagtatc aagagaacac agactcagag    660

aaggagagac aagaaggatt ggtgaggtct aagaaacaag aaatggagat tcaagaagct    720

gatttggctc ggattgagaa ggaagtagcg gaggcgaggt tgagggtcga ggagatgaaa    780

gcagagctcg ctgagctcga gacagagcgg ttgcggatgg aggagatggg atttaaggtc    840

gagaaatata aagggaagac gtttcttgat gaacttctgt ga                       882
```

<210> SEQ ID NO 12
<211> LENGTH: 1149
<212> TYPE: DNA
<213> ORGANISM: Arabidopsis thaliana

<400> SEQUENCE: 12

```
atggatgtca atcggaaagc tcacccggat tgtcgatatt cttcaaatcc tttccatgaa     60

tgtgcttcag attgtttaga gaagatctct caaggccgtg gaaataagaa ttcaaagaag    120

caaggttcaa agattcttag ccttccgggg agttttggta agaaaaagac ggagtcacag    180

ccaccgtcac ccctgagtac aaggaactat cagaatggtg ctgctaatac cccaaaggtt    240

cgtcaatcaa gaccttcacc agtagctatg aagaagacgc cagttccaga agcgaacaaa    300

tctttacact ctttatcgtc tgatggaatc tctattgacc tcaacggtca gaatgattct    360

tttaaccata agcaggagaa gccatcgcga actgttcctc tatccccaaa cagcatggct    420

gatcgtggga aacccttatc accacgacct caagggcatg aacacagtgg caagaatgac    480

acagccagtg agattagttt gtttaatgtt gtaagccctc caagatcatg cgccaatgat    540

gatgatgatg atgatgatga aaacaatggt tacgaggagg gagtggagtt agaccttata    600

tcagtaatgt cagactcatg tgtttcggtt ggaaaatacc gtgtgaactc aagtgtttcc    660

acaatcctac agtcaatcat tgataaacac ggagacatag cagcaaactg caagctagaa    720

tcagcatcaa tgcgatcccg atacctagag tgtctatgct cattgatgca agaacttgga    780

tcaaccccgg tgggtcagtt aaccgaacta aaagtaaaag agatggtcgc ggttctcaag    840

gacttggagt ctgtgaacat cgacgttggc tggatgcgtt cggttcttga ggagtttgct    900

cagtatcaag agaacacaga ctcagagaag gagagacaag aaggattggt gaggtctaag    960

aaacaagaaa tggagattca agaagctgat ttggctcgga ttgagaagga agtagcggag   1020

gcgaggttga gggtcgagga gatgaaagca gagctcgctg agctcgagac agagcggttg   1080

cggatggagg agatgggatt taaggtcgag aaatataaag ggaagacgtt tcttgatgaa   1140

cttctgtga                                                           1149
```

<210> SEQ ID NO 13
<211> LENGTH: 882
<212> TYPE: DNA
<213> ORGANISM: Arabidopsis thaliana

<400> SEQUENCE: 13

```
atgaagaaga cgccagttcc agaagcgaac aaatctttac actctttatc gtctgatgga     60

atctctattg acctcaacgg tcagaatgat tcttttaacc ataagcagga gaagccatcg    120

cgaactgttc ctctatcccc aaacagcatg gctgatcgtg ggaaaccctt atcaccacga    180

cctcaagggc atgaacacag tggcaagaat gacacagcca gtgagattag tttgtttaat    240
```

```
gttgtaagcc ctccaagatc atgcgccaat gatgatgatg atgatgatga tgaaaacaat    300

ggttacgagg agggagtgga gttagacctt atatcagtaa tgtcagactc atgtgtttcg    360

gttggaaaat accgtgtgaa ctcaagtgtt tccacaatcc tacagtcaat cattgataaa    420

cacggagaca tagcagcaaa ctgcaagcta gaatcagcat caatgcgatc ccgataccta    480

gagtgtctat gctcattgat gcaagaactt ggatcaaccc cggtgggtca gttaaccgaa    540

ctaaaagtaa aagagatggt cgcggttctc aaggacttgg agtctgtgaa catcgacgtt    600

ggctggatgc gttcggttct tgaggagttt gctcagtatc aagagaacac agactcagag    660

aaggagagac aagaaggatt ggtgaggtct aagaaacaag aaatggagat tcaagaagct    720

gatttggctc ggattgagaa ggaagtagcg gaggcgaggt tgagggtcga ggagatgaaa    780

gcagagctcg ctgagctcga gacagagcgg ttgcggatgg aggagatggg atttaaggtc    840

gagaaatata aagggaagac gtttcttgat gaacttctgt ga                       882
```

<210> SEQ ID NO 14
<211> LENGTH: 293
<212> TYPE: PRT
<213> ORGANISM: Arabidopsis thaliana

<400> SEQUENCE: 14

```
Met Lys Lys Thr Pro Val Pro Glu Ala Asn Lys Ser Leu His Ser Leu
1               5                   10                  15

Ser Ser Asp Gly Ile Ser Ile Asp Leu Asn Gly Gln Asn Asp Ser Phe
            20                  25                  30

Asn His Lys Gln Glu Lys Pro Ser Arg Thr Val Pro Leu Ser Pro Asn
        35                  40                  45

Ser Met Ala Asp Arg Gly Lys Pro Leu Ser Pro Arg Pro Gln Gly His
    50                  55                  60

Glu His Ser Gly Lys Asn Asp Thr Ala Ser Glu Ile Ser Leu Phe Asn
65                  70                  75                  80

Val Val Ser Pro Pro Arg Ser Cys Ala Asn Asp Asp Asp Asp Asp Asp
                85                  90                  95

Asp Glu Asn Asn Gly Tyr Glu Glu Gly Val Glu Leu Asp Leu Ile Ser
            100                 105                 110

Val Met Ser Asp Ser Cys Val Ser Val Gly Lys Tyr Arg Val Asn Ser
        115                 120                 125

Ser Val Ser Thr Ile Leu Gln Ser Ile Ile Asp Lys His Gly Asp Ile
    130                 135                 140

Ala Ala Asn Cys Lys Leu Glu Ser Ala Ser Met Arg Ser Arg Tyr Leu
145                 150                 155                 160

Glu Cys Leu Cys Ser Leu Met Gln Glu Leu Gly Ser Thr Pro Val Gly
                165                 170                 175

Gln Leu Thr Glu Leu Lys Val Lys Glu Met Val Ala Val Leu Lys Asp
            180                 185                 190

Leu Glu Ser Val Asn Ile Asp Val Gly Trp Met Arg Ser Val Leu Glu
        195                 200                 205

Glu Phe Ala Gln Tyr Gln Glu Asn Thr Asp Ser Glu Lys Glu Arg Gln
    210                 215                 220

Glu Gly Leu Val Arg Ser Lys Lys Gln Glu Met Glu Ile Gln Glu Ala
225                 230                 235                 240

Asp Leu Ala Arg Ile Glu Lys Glu Val Ala Glu Ala Arg Leu Arg Val
                245                 250                 255
```

-continued

```
Glu Glu Met Lys Ala Glu Leu Ala Glu Leu Glu Thr Glu Arg Leu Arg
            260                 265                 270

Met Glu Glu Met Gly Phe Lys Val Glu Lys Tyr Lys Gly Lys Thr Phe
        275                 280                 285

Leu Asp Glu Leu Leu
    290


<210> SEQ ID NO 15
<211> LENGTH: 382
<212> TYPE: PRT
<213> ORGANISM: Arabidopsis thaliana

<400> SEQUENCE: 15

Met Asp Val Asn Arg Lys Ala His Pro Asp Cys Arg Tyr Ser Ser Asn
1               5                   10                  15

Pro Phe His Glu Cys Ala Ser Asp Cys Leu Glu Lys Ile Ser Gln Gly
            20                  25                  30

Arg Gly Asn Lys Asn Ser Lys Lys Gln Gly Ser Lys Ile Leu Ser Leu
        35                  40                  45

Pro Gly Ser Phe Gly Lys Lys Lys Thr Glu Ser Gln Pro Pro Ser Pro
    50                  55                  60

Leu Ser Thr Arg Asn Tyr Gln Asn Gly Ala Ala Asn Thr Pro Lys Val
65                  70                  75                  80

Arg Gln Ser Arg Pro Ser Pro Val Ala Met Lys Lys Thr Pro Val Pro
                85                  90                  95

Glu Ala Asn Lys Ser Leu His Ser Leu Ser Ser Asp Gly Ile Ser Ile
            100                 105                 110

Asp Leu Asn Gly Gln Asn Asp Ser Phe Asn His Lys Gln Glu Lys Pro
        115                 120                 125

Ser Arg Thr Val Pro Leu Ser Pro Asn Ser Met Ala Asp Arg Gly Lys
    130                 135                 140

Pro Leu Ser Pro Arg Pro Gln Gly His Glu His Ser Gly Lys Asn Asp
145                 150                 155                 160

Thr Ala Ser Glu Ile Ser Leu Phe Asn Val Val Ser Pro Pro Arg Ser
                165                 170                 175

Cys Ala Asn Asp Asp Asp Asp Asp Asp Asp Glu Asn Asn Gly Tyr Glu
            180                 185                 190

Glu Gly Val Glu Leu Asp Leu Ile Ser Val Met Ser Asp Ser Cys Val
        195                 200                 205

Ser Val Gly Lys Tyr Arg Val Asn Ser Ser Val Ser Thr Ile Leu Gln
    210                 215                 220

Ser Ile Ile Asp Lys His Gly Asp Ile Ala Ala Asn Cys Lys Leu Glu
225                 230                 235                 240

Ser Ala Ser Met Arg Ser Arg Tyr Leu Glu Cys Leu Cys Ser Leu Met
                245                 250                 255

Gln Glu Leu Gly Ser Thr Pro Val Gly Gln Leu Thr Glu Leu Lys Val
            260                 265                 270

Lys Glu Met Val Ala Val Leu Lys Asp Leu Glu Ser Val Asn Ile Asp
        275                 280                 285

Val Gly Trp Met Arg Ser Val Leu Glu Glu Phe Ala Gln Tyr Gln Glu
    290                 295                 300

Asn Thr Asp Ser Glu Lys Glu Arg Gln Glu Gly Leu Val Arg Ser Lys
305                 310                 315                 320

Lys Gln Glu Met Glu Ile Gln Glu Ala Asp Leu Ala Arg Ile Glu Lys
                325                 330                 335
```

```
Glu Val Ala Glu Ala Arg Leu Arg Val Glu Glu Met Lys Ala Glu Leu
            340                 345                 350

Ala Glu Leu Glu Thr Glu Arg Leu Arg Met Glu Glu Met Gly Phe Lys
        355                 360                 365

Val Glu Lys Tyr Lys Gly Lys Thr Phe Leu Asp Glu Leu Leu
    370                 375                 380


<210> SEQ ID NO 16
<211> LENGTH: 293
<212> TYPE: PRT
<213> ORGANISM: Arabidopsis thaliana

<400> SEQUENCE: 16

Met Lys Lys Thr Pro Val Pro Glu Ala Asn Lys Ser Leu His Ser Leu
1               5                   10                  15

Ser Ser Asp Gly Ile Ser Ile Asp Leu Asn Gly Gln Asn Asp Ser Phe
            20                  25                  30

Asn His Lys Gln Glu Lys Pro Ser Arg Thr Val Pro Leu Ser Pro Asn
        35                  40                  45

Ser Met Ala Asp Arg Gly Lys Pro Leu Ser Pro Arg Pro Gln Gly His
    50                  55                  60

Glu His Ser Gly Lys Asn Asp Thr Ala Ser Glu Ile Ser Leu Phe Asn
65                  70                  75                  80

Val Val Ser Pro Pro Arg Ser Cys Ala Asn Asp Asp Asp Asp Asp Asp
                85                  90                  95

Asp Glu Asn Asn Gly Tyr Glu Glu Gly Val Glu Leu Asp Leu Ile Ser
            100                 105                 110

Val Met Ser Asp Ser Cys Val Ser Val Gly Lys Tyr Arg Val Asn Ser
        115                 120                 125

Ser Val Ser Thr Ile Leu Gln Ser Ile Ile Asp Lys His Gly Asp Ile
    130                 135                 140

Ala Ala Asn Cys Lys Leu Glu Ser Ala Ser Met Arg Ser Arg Tyr Leu
145                 150                 155                 160

Glu Cys Leu Cys Ser Leu Met Gln Glu Leu Gly Ser Thr Pro Val Gly
                165                 170                 175

Gln Leu Thr Glu Leu Lys Val Lys Glu Met Val Ala Val Leu Lys Asp
            180                 185                 190

Leu Glu Ser Val Asn Ile Asp Val Gly Trp Met Arg Ser Val Leu Glu
        195                 200                 205

Glu Phe Ala Gln Tyr Gln Glu Asn Thr Asp Ser Glu Lys Glu Arg Gln
    210                 215                 220

Glu Gly Leu Val Arg Ser Lys Lys Gln Glu Met Glu Ile Gln Glu Ala
225                 230                 235                 240

Asp Leu Ala Arg Ile Glu Lys Glu Val Ala Glu Ala Arg Leu Arg Val
                245                 250                 255

Glu Glu Met Lys Ala Glu Leu Ala Glu Leu Glu Thr Glu Arg Leu Arg
            260                 265                 270

Met Glu Glu Met Gly Phe Lys Val Glu Lys Tyr Lys Gly Lys Thr Phe
        275                 280                 285

Leu Asp Glu Leu Leu
    290


<210> SEQ ID NO 17
<211> LENGTH: 654
<212> TYPE: DNA
```

<213> ORGANISM: Arabidopsis thaliana

<400> SEQUENCE: 17
atggatgaat atgtagagga tgaacacgaa ttcagctacg aatggaacca agagaacggg 60
ccagcgaaat ggggaaagct aagaccggaa tggaaaatgt gcggaaaagg agaaatgcaa 120
tcgcctattg atcttatgaa caaaagagtt agacttgtta ctcatcttaa aaagcttact 180
agacactaca aaccttgtaa cgccactctc aaaaatagag gccatgatat gatgctgaaa 240
tttggagaag aagggtcagg gagtattacg gtcaatggaa ctgagtataa actcttacag 300
cttcattggc attctccctc tgaacatact atgaatggaa gaaggtttgc tctcgagcta 360
cacatggttc acgaaaacat taacggaagt ttggctgtag tcacagtcct ctacaaaatc 420
ggaaggccag attcttttct cggattgctg gaaaataaat tgtcggcaat tacagatcaa 480
aatgaggcgg agaaatatgt agatgtgatt gacccaaggg atattaagat tgggagcaga 540
aaattttata gatacattgg atcacttact actcctcctt gtacgcaaaa tgttatttgg 600
accgtcgtta aaaaggtaaa tactcatcgt tattttcttc tctttttac ttaa 654

<210> SEQ ID NO 18
<211> LENGTH: 217
<212> TYPE: PRT
<213> ORGANISM: Arabidopsis thaliana

<400> SEQUENCE: 18

Met Asp Glu Tyr Val Glu Asp Glu His Glu Phe Ser Tyr Glu Trp Asn
1               5                   10                  15

Gln Glu Asn Gly Pro Ala Lys Trp Gly Lys Leu Arg Pro Glu Trp Lys
            20                  25                  30

Met Cys Gly Lys Gly Glu Met Gln Ser Pro Ile Asp Leu Met Asn Lys
        35                  40                  45

Arg Val Arg Leu Val Thr His Leu Lys Lys Leu Thr Arg His Tyr Lys
    50                  55                  60

Pro Cys Asn Ala Thr Leu Lys Asn Arg Gly His Asp Met Met Leu Lys
65                  70                  75                  80

Phe Gly Glu Glu Gly Ser Gly Ser Ile Thr Val Asn Gly Thr Glu Tyr
                85                  90                  95

Lys Leu Leu Gln Leu His Trp His Ser Pro Ser Glu His Thr Met Asn
            100                 105                 110

Gly Arg Arg Phe Ala Leu Glu Leu His Met Val His Glu Asn Ile Asn
        115                 120                 125

Gly Ser Leu Ala Val Val Thr Val Leu Tyr Lys Ile Gly Arg Pro Asp
    130                 135                 140

Ser Phe Leu Gly Leu Leu Glu Asn Lys Leu Ser Ala Ile Thr Asp Gln
145                 150                 155                 160

Asn Glu Ala Glu Lys Tyr Val Asp Val Ile Asp Pro Arg Asp Ile Lys
                165                 170                 175

Ile Gly Ser Arg Lys Phe Tyr Arg Tyr Ile Gly Ser Leu Thr Thr Pro
            180                 185                 190

Pro Cys Thr Gln Asn Val Ile Trp Thr Val Val Lys Lys Val Asn Thr
        195                 200                 205

His Arg Tyr Phe Leu Leu Phe Phe Thr
    210                 215

<210> SEQ ID NO 19
<211> LENGTH: 1518

<212> TYPE: DNA
<213> ORGANISM: Arabidopsis thaliana

<400> SEQUENCE: 19
atggacctcc tcttgctgga gaagtcttta atcgccgtct tcgtggcggt gattctcgcc 60
acggtgattt caaagctccg cggcaagaaa ttgaagctac ctccaggtcc tataccaatt 120
ccgatcttcg gaaactggct tcaagtcgga gatgatctca accaccgtaa tctcgtcgat 180
tacgctaaga aattcggcga tctcttcctc ctccgtatgg gtcagcgaaa cctagtcgtc 240
gtctcctcac cggatctaac aaaggaagtg ctcctcactc aaggcgttga gtttggatcc 300
agaacgagaa acgtcgtgtt cgacattttc accgggaaag gtcaagatat ggtgttcact 360
gtttacggcg agcattggag gaagatgaga agaatcatga cggttccttt cttcaccaac 420
aaagttgttc aacagaatcg tgaaggttgg gagtttgaag cagctagtgt tgttgaagat 480
gttaagaaga atccagattc tgctacgaaa ggaatcgtgt tgaggaaacg tttgcaattg 540
atgatgtata acaatatgtt ccgtatcatg ttcgatagaa gatttgagag tgaggatgat 600
cctcttttcc ttaggcttaa ggctttgaat ggtgagagaa gtcgattagc tcagagcttt 660
gagtataact atggagattt cattcctatc cttagaccat tcctcagagg ctatttgaag 720
atttgtcaag atgtgaaaga tcgaagaatc gctcttttca agaagtactt tgttgatgag 780
aggaagcaaa ttgcgagttc taagcctaca ggtagtgaag gattgaaatg tgccattgat 840
cacatccttg aagctgagca gaagggagaa atcaacgagg acaatgttct ttacatcgtc 900
gagaacatca atgtcgccgc gattgagaca acattgtggt ctatcgagtg gggaattgca 960
gagctagtga accatcctga aatccagagt aagctaagga acgaactcga cacagttctt 1020
ggaccgggtg tgcaagtcac cgagcctgat cttcacaaac ttccatacct tcaagctgtg 1080
gttaaggaga ctcttcgtct gagaatggcg attcctctcc tcgtgcctca catgaacctc 1140
catgatgcga agctcgctgg ctacgatatc ccagcagaaa gcaaaatcct tgttaatgct 1200
tggtggctag caaacaaccc caacagctgg aagaagcctg aagagtttag accagagagg 1260
ttctttgaag aagaatcgca cgtggaagct aacggtaatg acttcaggta tgtgccattt 1320
ggtgttggac gtcgaagctg tcccgggatt atattggcat tgcctatttt ggggatcacc 1380
attggtagga tggtccagaa cttcgagctt cttcctcctc caggacagtc taaagtggat 1440
actagtgaga aaggtggaca attcagcttg cacatcctta accactccat aatcgttatg 1500
aaaccaagga actgttaa 1518

<210> SEQ ID NO 20
<211> LENGTH: 505
<212> TYPE: PRT
<213> ORGANISM: Arabidopsis thaliana

<400> SEQUENCE: 20

Met Asp Leu Leu Leu Leu Glu Lys Ser Leu Ile Ala Val Phe Val Ala
1 5 10 15

Val Ile Leu Ala Thr Val Ile Ser Lys Leu Arg Gly Lys Lys Leu Lys
20 25 30

Leu Pro Pro Gly Pro Ile Pro Ile Pro Ile Phe Gly Asn Trp Leu Gln
35 40 45

Val Gly Asp Asp Leu Asn His Arg Asn Leu Val Asp Tyr Ala Lys Lys
50 55 60

Phe Gly Asp Leu Phe Leu Leu Arg Met Gly Gln Arg Asn Leu Val Val
65 70 75 80

-continued

```
Val Ser Ser Pro Asp Leu Thr Lys Glu Val Leu Leu Thr Gln Gly Val
                85                  90                  95

Glu Phe Gly Ser Arg Thr Arg Asn Val Val Phe Asp Ile Phe Thr Gly
            100                 105                 110

Lys Gly Gln Asp Met Val Phe Thr Val Tyr Gly Glu His Trp Arg Lys
        115                 120                 125

Met Arg Arg Ile Met Thr Val Pro Phe Phe Thr Asn Lys Val Val Gln
    130                 135                 140

Gln Asn Arg Glu Gly Trp Glu Phe Glu Ala Ala Ser Val Val Glu Asp
145                 150                 155                 160

Val Lys Lys Asn Pro Asp Ser Ala Thr Lys Gly Ile Val Leu Arg Lys
                165                 170                 175

Arg Leu Gln Leu Met Met Tyr Asn Asn Met Phe Arg Ile Met Phe Asp
            180                 185                 190

Arg Arg Phe Glu Ser Glu Asp Asp Pro Leu Phe Leu Arg Leu Lys Ala
        195                 200                 205

Leu Asn Gly Glu Arg Ser Arg Leu Ala Gln Ser Phe Glu Tyr Asn Tyr
    210                 215                 220

Gly Asp Phe Ile Pro Ile Leu Arg Pro Phe Leu Arg Gly Tyr Leu Lys
225                 230                 235                 240

Ile Cys Gln Asp Val Lys Asp Arg Arg Ile Ala Leu Phe Lys Lys Tyr
                245                 250                 255

Phe Val Asp Glu Arg Lys Gln Ile Ala Ser Ser Lys Pro Thr Gly Ser
            260                 265                 270

Glu Gly Leu Lys Cys Ala Ile Asp His Ile Leu Glu Ala Glu Gln Lys
        275                 280                 285

Gly Glu Ile Asn Glu Asp Asn Val Leu Tyr Ile Val Glu Asn Ile Asn
    290                 295                 300

Val Ala Ala Ile Glu Thr Thr Leu Trp Ser Ile Glu Trp Gly Ile Ala
305                 310                 315                 320

Glu Leu Val Asn His Pro Glu Ile Gln Ser Lys Leu Arg Asn Glu Leu
                325                 330                 335

Asp Thr Val Leu Gly Pro Gly Val Gln Val Thr Glu Pro Asp Leu His
            340                 345                 350

Lys Leu Pro Tyr Leu Gln Ala Val Val Lys Glu Thr Leu Arg Leu Arg
        355                 360                 365

Met Ala Ile Pro Leu Leu Val Pro His Met Asn Leu His Asp Ala Lys
    370                 375                 380

Leu Ala Gly Tyr Asp Ile Pro Ala Glu Ser Lys Ile Leu Val Asn Ala
385                 390                 395                 400

Trp Trp Leu Ala Asn Asn Pro Asn Ser Trp Lys Lys Pro Glu Glu Phe
                405                 410                 415

Arg Pro Glu Arg Phe Phe Glu Glu Glu Ser His Val Glu Ala Asn Gly
            420                 425                 430

Asn Asp Phe Arg Tyr Val Pro Phe Gly Val Gly Arg Arg Ser Cys Pro
        435                 440                 445

Gly Ile Ile Leu Ala Leu Pro Ile Leu Gly Ile Thr Ile Gly Arg Met
    450                 455                 460

Val Gln Asn Phe Glu Leu Leu Pro Pro Pro Gly Gln Ser Lys Val Asp
465                 470                 475                 480

Thr Ser Glu Lys Gly Gly Gln Phe Ser Leu His Ile Leu Asn His Ser
                485                 490                 495
```

```
Ile Ile Val Met Lys Pro Arg Asn Cys
            500                 505


<210> SEQ ID NO 21
<211> LENGTH: 1536
<212> TYPE: DNA
<213> ORGANISM: Arabidopsis thaliana

<400> SEQUENCE: 21

atggagatca ccactatcat attcctcatc atatcctctc tcaccttctc catcttcctt     60

aaactcatct tcttcttctc aactcacaaa ctcccaccgg gaccacctcg ttttccggtc    120

atcggaaaca tcatctggct taagaaaaac aacttctccg atttccaagg cgttctccgt    180

gacttagcct cccgtcacgg accaatcata acactccacg taggctccaa accttccatc    240

tgggtcacag acagatcact cgctcaccaa gcccttgtcc aaaacggtgc cgttttctcc    300

gaccgttctc tcgctctccc taccaccaaa gtcatcacca gcaaccaaca cgacatccac    360

tcctccgtct atggctctct ctggagaacc ctccgccgca acctcacctc cgaaatcctc    420

cagccctcgc gcgtgaaagc acacgcgccg tcgaggaaat ggtctctcga gattctcgtg    480

gatctgttcg agacagagca gagagagaaa ggacatatct ccgacgcttt agatcattta    540

cgtcacgcta tgttttattt gttggctctg atgtgtttcg gagagaaact gagaaaagaa    600

gagatcagag agatcgaaga agctcagtac caaatgctca taagctacac caagttcagc    660

gtcctcaaca tcttcccaag cgtaaccaag ttcttgctcc ggcgaaaatg gaaagagttt    720

ttagaactaa ggaaatctca agagagcgtt atacttcgat acgtgaacgc aagaagcaaa    780

gaaaccaccg gagatgttct ctgttacgtc gatacgctgc tgaatcttga gatcccgacg    840

gaggagaaag aaggagggaa gaagaggaaa ctgagtgact cggagatcgt gagtctgtgt    900

tcggagtttc ttaacgcagc tacggatcca acggcgacgt cgatgcagtg gatcatggcg    960

atcatggtga agtatccaga gatacagagg aaagtatacg aggaaatgaa gactgtgttc   1020

gccggagaag aagaagaaag agaagagatc agagaagagg atttggggaa gttgagttac   1080

ctcaaagctg tgatcttgga gtgtctaaga agacaccctc ctggtcatta cttgtcttac   1140

cataaggtca cacacgacac cgttttgggt ggatttctca ttccgcgcca aggtactata   1200

aactttatgg taggagaaat gggccgggac ccaaaaatat gggaagatcc tctaacgttc   1260

aagccagaaa gatttctaga gaacggagaa gcatgtgatt ttgatatgac gggaactcgc   1320

gagattaaaa tgatgccgtt tggagcggga cgacggatgt gtcccggcta cgcgctttcg   1380

ttgcttcacc tggaatatta tgtggccaat ttggtttgga aattcgagtg gaaatgtgtg   1440

gaaggtgaag aagttgatct atccgagaag caacagttca tcacaatggt catgaaaaac   1500

cctttcaaag caaatattta tccaaggaga aagtga                              1536


<210> SEQ ID NO 22
<211> LENGTH: 511
<212> TYPE: PRT
<213> ORGANISM: Arabidopsis thaliana

<400> SEQUENCE: 22

Met Glu Ile Thr Thr Ile Ile Phe Leu Ile Ile Ser Ser Leu Thr Phe
1               5                   10                  15

Ser Ile Phe Leu Lys Leu Ile Phe Phe Phe Ser Thr His Lys Leu Pro
            20                  25                  30

Pro Gly Pro Pro Arg Phe Pro Val Ile Gly Asn Ile Ile Trp Leu Lys
        35                  40                  45
```

-continued

```
Lys Asn Asn Phe Ser Asp Phe Gln Gly Val Leu Arg Asp Leu Ala Ser
    50                  55                  60

Arg His Gly Pro Ile Ile Thr Leu His Val Gly Ser Lys Pro Ser Ile
65                  70                  75                  80

Trp Val Thr Asp Arg Ser Leu Ala His Gln Ala Leu Val Gln Asn Gly
                85                  90                  95

Ala Val Phe Ser Asp Arg Ser Leu Ala Leu Pro Thr Thr Lys Val Ile
            100                 105                 110

Thr Ser Asn Gln His Asp Ile His Ser Ser Val Tyr Gly Ser Leu Trp
        115                 120                 125

Arg Thr Leu Arg Arg Asn Leu Thr Ser Glu Ile Leu Gln Pro Ser Arg
    130                 135                 140

Val Lys Ala His Ala Pro Ser Arg Lys Trp Ser Leu Glu Ile Leu Val
145                 150                 155                 160

Asp Leu Phe Glu Thr Glu Gln Arg Glu Lys Gly His Ile Ser Asp Ala
                165                 170                 175

Leu Asp His Leu Arg His Ala Met Phe Tyr Leu Leu Ala Leu Met Cys
            180                 185                 190

Phe Gly Glu Lys Leu Arg Lys Glu Glu Ile Arg Glu Ile Glu Glu Ala
        195                 200                 205

Gln Tyr Gln Met Leu Ile Ser Tyr Thr Lys Phe Ser Val Leu Asn Ile
    210                 215                 220

Phe Pro Ser Val Thr Lys Phe Leu Leu Arg Arg Lys Trp Lys Glu Phe
225                 230                 235                 240

Leu Glu Leu Arg Lys Ser Gln Glu Ser Val Ile Leu Arg Tyr Val Asn
                245                 250                 255

Ala Arg Ser Lys Glu Thr Thr Gly Asp Val Leu Cys Tyr Val Asp Thr
            260                 265                 270

Leu Leu Asn Leu Glu Ile Pro Thr Glu Glu Lys Glu Gly Gly Lys Lys
        275                 280                 285

Arg Lys Leu Ser Asp Ser Glu Ile Val Ser Leu Cys Ser Glu Phe Leu
    290                 295                 300

Asn Ala Ala Thr Asp Pro Thr Ala Thr Ser Met Gln Trp Ile Met Ala
305                 310                 315                 320

Ile Met Val Lys Tyr Pro Glu Ile Gln Arg Lys Val Tyr Glu Glu Met
                325                 330                 335

Lys Thr Val Phe Ala Gly Glu Glu Glu Glu Arg Glu Glu Ile Arg Glu
            340                 345                 350

Glu Asp Leu Gly Lys Leu Ser Tyr Leu Lys Ala Val Ile Leu Glu Cys
        355                 360                 365

Leu Arg Arg His Pro Pro Gly His Tyr Leu Ser Tyr His Lys Val Thr
    370                 375                 380

His Asp Thr Val Leu Gly Gly Phe Leu Ile Pro Arg Gln Gly Thr Ile
385                 390                 395                 400

Asn Phe Met Val Gly Glu Met Gly Arg Asp Pro Lys Ile Trp Glu Asp
                405                 410                 415

Pro Leu Thr Phe Lys Pro Glu Arg Phe Leu Glu Asn Gly Glu Ala Cys
            420                 425                 430

Asp Phe Asp Met Thr Gly Thr Arg Glu Ile Lys Met Met Pro Phe Gly
        435                 440                 445

Ala Gly Arg Arg Met Cys Pro Gly Tyr Ala Leu Ser Leu Leu His Leu
    450                 455                 460
```

-continued

```
Glu Tyr Tyr Val Ala Asn Leu Val Trp Lys Phe Glu Trp Lys Cys Val
465                 470                 475                 480

Glu Gly Glu Glu Val Asp Leu Ser Glu Lys Gln Gln Phe Ile Thr Met
                485                 490                 495

Val Met Lys Asn Pro Phe Lys Ala Asn Ile Tyr Pro Arg Arg Lys
            500                 505                 510


<210> SEQ ID NO 23
<211> LENGTH: 936
<212> TYPE: DNA
<213> ORGANISM: Arabidopsis thaliana

<400> SEQUENCE: 23

atgatgaccc aaaaaccacg aactgtgatc tgcgtcggag acatccatgg aaacatatca      60

aagctcaata aactctggct taatcttcaa tccgatatcc aaaactcaga tttcagctca     120

gctctcgtca tcttcctcgg cgactactgc gatcgtggac cggagactcg aaaagtcatc     180

gacttcttga tctctttgcc ggagaaacat cccgatcaga cccatgtctt tcttgccgga     240

aaccacgact ttgcttttgc tggcttcttg ggtttgttac ctcgcccttc agatgggtct     300

gagtttaagg aaacgtggaa agagtactca aaaagtgagg agagagaagg atggtataaa     360

ggtgaagggt ttgagaatat gcatctccaa agcaggagat gggcgggaaa gattagggtt     420

cagttcgatt attccgcata tggagtgttg tataatggat caatatacga tgcggcgtct     480

acttttgaat cttatggcgt tcctcatgga tcttctgatt tgataaaggc agtacctgag     540

agtcacaaga aattcttgac caatatggtt tgggtacata aagaggatga tgtttgtata     600

gaaacagagg aaggccttac gcattgtaag ttgattgccg tacatgctgg tctagagaca     660

aagaataacg tagaagaaca gcttaaacta ttgagagata aagacacaag catcccaaga     720

atacaacctc taactggtcg gaaaaccgtt tgggggatcc cacaggaact ggatgataaa     780

aagactattg ttgttagcgg ccaccatggg aaacttcaca tcgatggctt gagattgatc     840

atcgatgaag gtggtggata taccgataca cctttggctg caattgttct tccttctaag     900

aagattatcc gcgacaccga taatttttcc aattaa                               936


<210> SEQ ID NO 24
<211> LENGTH: 311
<212> TYPE: PRT
<213> ORGANISM: Arabidopsis thaliana

<400> SEQUENCE: 24

Met Met Thr Gln Lys Pro Arg Thr Val Ile Cys Val Gly Asp Ile His
1               5                   10                  15

Gly Asn Ile Ser Lys Leu Asn Lys Leu Trp Leu Asn Leu Gln Ser Asp
            20                  25                  30

Ile Gln Asn Ser Asp Phe Ser Ser Ala Leu Val Ile Phe Leu Gly Asp
        35                  40                  45

Tyr Cys Asp Arg Gly Pro Glu Thr Arg Lys Val Ile Asp Phe Leu Ile
    50                  55                  60

Ser Leu Pro Glu Lys His Pro Asp Gln Thr His Val Phe Leu Ala Gly
65                  70                  75                  80

Asn His Asp Phe Ala Phe Ala Gly Phe Leu Gly Leu Leu Pro Arg Pro
                85                  90                  95

Ser Asp Gly Ser Glu Phe Lys Glu Thr Trp Lys Glu Tyr Ser Lys Ser
            100                 105                 110

Glu Glu Arg Glu Gly Trp Tyr Lys Gly Glu Gly Phe Glu Asn Met His
```

-continued

```
        115                 120                 125

Leu Gln Ser Arg Arg Trp Ala Gly Lys Ile Arg Val Gln Phe Asp Tyr
    130                 135                 140

Ser Ala Tyr Gly Val Leu Tyr Asn Gly Ser Ile Tyr Asp Ala Ala Ser
145                 150                 155                 160

Thr Phe Glu Ser Tyr Gly Val Pro His Gly Ser Ser Asp Leu Ile Lys
                165                 170                 175

Ala Val Pro Glu Ser His Lys Lys Phe Leu Thr Asn Met Val Trp Val
            180                 185                 190

His Lys Glu Asp Asp Val Cys Ile Glu Thr Glu Glu Gly Leu Thr His
        195                 200                 205

Cys Lys Leu Ile Ala Val His Ala Gly Leu Glu Thr Lys Asn Asn Val
    210                 215                 220

Glu Glu Gln Leu Lys Leu Leu Arg Asp Lys Asp Thr Ser Ile Pro Arg
225                 230                 235                 240

Ile Gln Pro Leu Thr Gly Arg Lys Thr Val Trp Gly Ile Pro Gln Glu
                245                 250                 255

Leu Asp Asp Lys Lys Thr Ile Val Val Ser Gly His His Gly Lys Leu
            260                 265                 270

His Ile Asp Gly Leu Arg Leu Ile Ile Asp Glu Gly Gly Gly Tyr Thr
        275                 280                 285

Asp Thr Pro Leu Ala Ala Ile Val Leu Pro Ser Lys Lys Ile Ile Arg
    290                 295                 300

Asp Thr Asp Asn Phe Ser Asn
305                 310


<210> SEQ ID NO 25
<211> LENGTH: 4401
<212> TYPE: DNA
<213> ORGANISM: Arabidopsis thaliana

<400> SEQUENCE: 25

atggaaaatc ctatcgattc tcttctcctc cagcccatct acctttcggt actttcgttt     60

ttcttgaatc tggtgttgtt gctaattctt tttggttcat ggcttttcaa aaagagagta    120

gcttgtgaag atactgatgc tatcatgaat gaagagttta aacacatatc tttctcgtat    180

aataaactgg ttcttatttg ttgtgtctca ttatctgtgt tttattctgt gctttcgttg    240

ctaagttgcc ttcactggca tacaaatggt tggccttttct tagatcttct gttggctgcc    300

cttacttggg gttccatctc tgtttacctg tttggtcgat acactaattc ttgtgagcaa    360

aaagtactat ttttgcttag agtttggtgg gttttctttt tcgtggtttc ttgctaccat    420

cttgtggtag actttgttct atacaagaag caagaaatgg tgtcagttca ctttgtaatt    480

tctgatttgg tgggcgtctg cgctggcttg tttctctgtt gttcgtgctt gtggaagaaa    540

ggagaaggtg aaaggatcga ccttctcaaa gaaccactct tgagcagtgc tgaatctagt    600

gataatgaag aggtcactgc accttttttca aaagctggga ttctaagccg catgagtttc    660

tcctggatga gccctttgat taccttagga aatgagaaaa tcatagacat caaggatgtt    720

cctcaacttg accgtagtga cacaactgag agcctatttt ggatatttag gagtaagctt    780

gaatgggacg atggtgaaag aaggatcacc acatttaagc taatcaaggc tctcttcctc    840

tcagtgtggc gagatattgt tttgtcagct ctgcttgctt ttgtctacac ggtgtcttgc    900

tacgttgcac catatctcat ggataatttc gttcagtacc tgaatggtaa cagacaatat    960

aagaaccaag gttatgtgtt agtgacaact ttctttgttg ctaagcttgt ggaatgccaa   1020
```

-continued

```
acacagaggc agtggttctt tagggggcaa aaagctgggc ttgggatgag atcggtcctg   1080
gtttcgatga tctatgaaaa ggggttgacc cttccatgtc attcgaagca aggacacact   1140
agtggcgaga ttataaacct catggcagta gatgctgaca ggatcagtgc ttttagttgg   1200
tttatgcatg atccatggat acttgtttta caagttagtt tggccttatg gatcttgtat   1260
aaaagcctcg gattaggatc aattgcagct tttcctgcaa ctattttagt tatgctggca   1320
aattatccct ttgcaaagtt ggaagagaag tttcagagca gtttgatgaa gtccaaagac   1380
aacagaatga agaaaacatc ggaggtctta ctgaacatga agattctcaa acttcaggga   1440
tgggagatga agtttctttc taagatcctt gaacttagac atattgaagc aggctggcta   1500
aaaaagtttg tgtacaattc gtccgctatc aactctgttt tgtgggcggc accttctttc   1560
atatctgcaa cagcttttgg cgcatgttta ttgctgaaaa ttcctcttga atcagggaag   1620
atactggcgg ctcttgcaac tttccggatt ctgcaaggcc caatctacaa acttcccgaa   1680
acaatctcaa tgattgttca aactaaggta tctcttaata ggattgcatc ttttctctgt   1740
ctagatgact tgcagcaaga tgttgtgggg aggcttccta gtggaagttc agaaatggct   1800
gtggaaatca gtaatggtac tttctcctgg gatgactctt ccccaatccc gacattgaga   1860
gacatgaatt tcaaagtttc tcagggcatg aatgtagcta tttgtggtac tgttggctcg   1920
gggaaatcaa gcctactctc atccatactg ggtgaagttc ccaaaatatc tggaaatctt   1980
aaagtttgtg gaagaaaggc atacattgca caatcacctt ggatccaaag cggcaaagtc   2040
gaagagaaca ttctgtttgg taagccaatg gaaagagagt ggtacgatag ggtgcttgaa   2100
gcatgttctt taaataaaga cttggagata cttccgttcc atgaccagac agttattggg   2160
gaaaggggta tcaatttaag cggtgggcag aagcagcgta tacaaatcgc ccgtgctctc   2220
taccaagacg cagatattta tctgtttgat gaccctttta gtgcagtaga cgctcatact   2280
ggatcacatc tctttaagga agttctgctg gggcttctga gacacaagac agtcatatat   2340
gtcactcatc aagttgaatt cttgcctgaa gctgatctta tattggtcat gaaagatggc   2400
aagataacac aagcggggaa ataccatgag attctcgatt caggaacaga tttcatggaa   2460
cttgtaggag ctcacactga agccttagca acaattgatt catgtgaaac aggctatgct   2520
tctgaaaaat caactacgga caaagaaaac gaagtactcc atcataaaga aaaacaagag   2580
aatggttcgg ataacaagcc aagcggacaa ctagttcaag aagaggaaag ggagaaggga   2640
aaagttgggt tcactgtgta caaaaaatac atggcactag catacggagg agcagttatt   2700
cctttaatat tggtggtaca ggttctcttt cagcttctga gcattgggag caattattgg   2760
atgacctggg tgactcctgt ttccaaggac gtggaacctc cagtgagcgg cttcacattg   2820
attctagtct atgtacttct agcggtcgca agctccttct gcatactcat cagagctttg   2880
ctggttgcga tgactggttt caagatggct actgaactct tcacccaaat gcatctccgc   2940
attttccgtg cctccatgtc attctttgat gccaccccaa tggggcgaat tttgaataga   3000
gcttctacag accaaagtgt cgcagatttg agattacccg gtcaatttgc atatgttgct   3060
atcgcagcta ttaacatttt ggggattatc ggagtgatag tacaggttgc ttggcaggtc   3120
cttattgtct tcatccctgt cgtcgctgca tgtgcctggt accggcaata ttacatatcc   3180
gcagctcgag aactcgcaag attagctgga ataagcagat ctcctgtggt acatcatttt   3240
tctgaaacac tttcagggat aacaactatc aggagttttg atcaagaacc aaggttccgt   3300
ggtgacatca tgagacttag tgattgttat tcacggctga agttccattc gaccggtgca   3360
```

-continued atggaatggc tctgcttccg ccttgaactt ttatccactt tcgcattcgc ttcttcactt 3420
gttatcttag tttctgcccc tgaaggagtc attaatccaa gcttagcagg actggcgatt 3480
acatatgcac tcaatctaaa taccctgcaa gcaactttaa tatggacgct ttgtgatctc 3540
gagaacaaaa tgatatctgt ggagagaatg cttcaataca caaacatccc cagtgaacca 3600
cctcttgtga ttgaaacaac tcggcctgag aaatcatggc cttctcgtgg agagattact 3660
atctgtaatc tgcaagtacg atatgggcca catttgccca tggtgctgca tggactgaca 3720
tgcacttttc caggaggcct gaaaaccgga atcgttggaa gaacaggatg tggcaaatcc 3780
actctaattc aaaccctttt taggattgtg gaacctgcag cgggagaaat caggatagat 3840
gggataaaca tcttgtccat tgggctgcat gaccttcgtt ctagactaag tatcatacct 3900
caagatccaa ccatgtttga aggcacgatt cgtagtaact tggaccctct tgaggaatac 3960
actgatgacc aaatctggga ggcactcgac aattgtcaac ttggggacga agtaaggaag 4020
aaagaactaa agctggattc ccctgttagt gagaatggac agaactggag tgttggtcag 4080
agacaattgg tgtgcctggg acgagtcttg ctcaagagaa gcaaattact ggttcttgat 4140
gaagccacag cttctatcga taccgctact gataatctga tccaggagac tctgaggcac 4200
cactttgcgg attgtacagt gataacaatc gcacatagaa tatcttctgt gatagacagc 4260
gatatggtcc tgctcctaga ccaaggtctt atcaaagaac atgattcacc ggcgagattg 4320
ctagaagaca ggtcgtcatt attctcaaag cttgtggcag agtacacaac aagttctgaa 4380
tccaaatcca aaagaagctg a 4401

<210> SEQ ID NO 26
<211> LENGTH: 1466
<212> TYPE: PRT
<213> ORGANISM: Arabidopsis thaliana

<400> SEQUENCE: 26

Met Glu Asn Pro Ile Asp Ser Leu Leu Leu Gln Pro Ile Tyr Leu Ser
1 5 10 15

Val Leu Ser Phe Phe Leu Asn Leu Val Leu Leu Leu Ile Leu Phe Gly
20 25 30

Ser Trp Leu Phe Lys Lys Arg Val Ala Cys Glu Asp Thr Asp Ala Ile
35 40 45

Met Asn Glu Glu Phe Lys His Ile Ser Phe Ser Tyr Asn Lys Leu Val
50 55 60

Leu Ile Cys Cys Val Ser Leu Ser Val Phe Tyr Ser Val Leu Ser Leu
65 70 75 80

Leu Ser Cys Leu His Trp His Thr Asn Gly Trp Pro Phe Leu Asp Leu
85 90 95

Leu Leu Ala Ala Leu Thr Trp Gly Ser Ile Ser Val Tyr Leu Phe Gly
100 105 110

Arg Tyr Thr Asn Ser Cys Glu Gln Lys Val Leu Phe Leu Leu Arg Val
115 120 125

Trp Trp Val Phe Phe Phe Val Val Ser Cys Tyr His Leu Val Val Asp
130 135 140

Phe Val Leu Tyr Lys Lys Gln Glu Met Val Ser Val His Phe Val Ile
145 150 155 160

Ser Asp Leu Val Gly Val Cys Ala Gly Leu Phe Leu Cys Cys Ser Cys
165 170 175

Leu Trp Lys Lys Gly Glu Gly Glu Arg Ile Asp Leu Leu Lys Glu Pro
180 185 190

-continued

```
Leu Leu Ser Ser Ala Glu Ser Ser Asp Asn Glu Glu Val Thr Ala Pro
        195                 200                 205

Phe Ser Lys Ala Gly Ile Leu Ser Arg Met Ser Phe Ser Trp Met Ser
    210                 215                 220

Pro Leu Ile Thr Leu Gly Asn Glu Lys Ile Ile Asp Ile Lys Asp Val
225                 230                 235                 240

Pro Gln Leu Asp Arg Ser Asp Thr Thr Glu Ser Leu Phe Trp Ile Phe
                245                 250                 255

Arg Ser Lys Leu Glu Trp Asp Asp Gly Glu Arg Arg Ile Thr Thr Phe
            260                 265                 270

Lys Leu Ile Lys Ala Leu Phe Leu Ser Val Trp Arg Asp Ile Val Leu
        275                 280                 285

Ser Ala Leu Leu Ala Phe Val Tyr Thr Val Ser Cys Tyr Val Ala Pro
    290                 295                 300

Tyr Leu Met Asp Asn Phe Val Gln Tyr Leu Asn Gly Asn Arg Gln Tyr
305                 310                 315                 320

Lys Asn Gln Gly Tyr Val Leu Val Thr Thr Phe Phe Val Ala Lys Leu
                325                 330                 335

Val Glu Cys Gln Thr Gln Arg Gln Trp Phe Phe Arg Gly Gln Lys Ala
            340                 345                 350

Gly Leu Gly Met Arg Ser Val Leu Val Ser Met Ile Tyr Glu Lys Gly
        355                 360                 365

Leu Thr Leu Pro Cys His Ser Lys Gln Gly His Thr Ser Gly Glu Ile
    370                 375                 380

Ile Asn Leu Met Ala Val Asp Ala Asp Arg Ile Ser Ala Phe Ser Trp
385                 390                 395                 400

Phe Met His Asp Pro Trp Ile Leu Val Leu Gln Val Ser Leu Ala Leu
                405                 410                 415

Trp Ile Leu Tyr Lys Ser Leu Gly Leu Gly Ser Ile Ala Ala Phe Pro
            420                 425                 430

Ala Thr Ile Leu Val Met Leu Ala Asn Tyr Pro Phe Ala Lys Leu Glu
        435                 440                 445

Glu Lys Phe Gln Ser Ser Leu Met Lys Ser Lys Asp Asn Arg Met Lys
    450                 455                 460

Lys Thr Ser Glu Val Leu Leu Asn Met Lys Ile Leu Lys Leu Gln Gly
465                 470                 475                 480

Trp Glu Met Lys Phe Leu Ser Lys Ile Leu Glu Leu Arg His Ile Glu
                485                 490                 495

Ala Gly Trp Leu Lys Lys Phe Val Tyr Asn Ser Ser Ala Ile Asn Ser
            500                 505                 510

Val Leu Trp Ala Ala Pro Ser Phe Ile Ser Ala Thr Ala Phe Gly Ala
        515                 520                 525

Cys Leu Leu Leu Lys Ile Pro Leu Glu Ser Gly Lys Ile Leu Ala Ala
    530                 535                 540

Leu Ala Thr Phe Arg Ile Leu Gln Gly Pro Ile Tyr Lys Leu Pro Glu
545                 550                 555                 560

Thr Ile Ser Met Ile Val Gln Thr Lys Val Ser Leu Asn Arg Ile Ala
                565                 570                 575

Ser Phe Leu Cys Leu Asp Asp Leu Gln Gln Asp Val Val Gly Arg Leu
            580                 585                 590

Pro Ser Gly Ser Ser Glu Met Ala Val Glu Ile Ser Asn Gly Thr Phe
        595                 600                 605
```

-continued

```
Ser Trp Asp Asp Ser Ser Pro Ile Pro Thr Leu Arg Asp Met Asn Phe
    610                 615                 620

Lys Val Ser Gln Gly Met Asn Val Ala Ile Cys Gly Thr Val Gly Ser
625                 630                 635                 640

Gly Lys Ser Ser Leu Leu Ser Ser Ile Leu Gly Glu Val Pro Lys Ile
                645                 650                 655

Ser Gly Asn Leu Lys Val Cys Gly Arg Lys Ala Tyr Ile Ala Gln Ser
            660                 665                 670

Pro Trp Ile Gln Ser Gly Lys Val Glu Glu Asn Ile Leu Phe Gly Lys
        675                 680                 685

Pro Met Glu Arg Glu Trp Tyr Asp Arg Val Leu Glu Ala Cys Ser Leu
    690                 695                 700

Asn Lys Asp Leu Glu Ile Leu Pro Phe His Asp Gln Thr Val Ile Gly
705                 710                 715                 720

Glu Arg Gly Ile Asn Leu Ser Gly Gly Gln Lys Gln Arg Ile Gln Ile
                725                 730                 735

Ala Arg Ala Leu Tyr Gln Asp Ala Asp Ile Tyr Leu Phe Asp Asp Pro
            740                 745                 750

Phe Ser Ala Val Asp Ala His Thr Gly Ser His Leu Phe Lys Glu Val
        755                 760                 765

Leu Leu Gly Leu Leu Arg His Lys Thr Val Ile Tyr Val Thr His Gln
    770                 775                 780

Val Glu Phe Leu Pro Glu Ala Asp Leu Ile Leu Val Met Lys Asp Gly
785                 790                 795                 800

Lys Ile Thr Gln Ala Gly Lys Tyr His Glu Ile Leu Asp Ser Gly Thr
                805                 810                 815

Asp Phe Met Glu Leu Val Gly Ala His Thr Glu Ala Leu Ala Thr Ile
            820                 825                 830

Asp Ser Cys Glu Thr Gly Tyr Ala Ser Glu Lys Ser Thr Thr Asp Lys
        835                 840                 845

Glu Asn Glu Val Leu His His Lys Glu Lys Gln Glu Asn Gly Ser Asp
    850                 855                 860

Asn Lys Pro Ser Gly Gln Leu Val Gln Glu Glu Glu Arg Glu Lys Gly
865                 870                 875                 880

Lys Val Gly Phe Thr Val Tyr Lys Lys Tyr Met Ala Leu Ala Tyr Gly
                885                 890                 895

Gly Ala Val Ile Pro Leu Ile Leu Val Val Gln Val Leu Phe Gln Leu
            900                 905                 910

Leu Ser Ile Gly Ser Asn Tyr Trp Met Thr Trp Val Thr Pro Val Ser
        915                 920                 925

Lys Asp Val Glu Pro Pro Val Ser Gly Phe Thr Leu Ile Leu Val Tyr
    930                 935                 940

Val Leu Leu Ala Val Ala Ser Ser Phe Cys Ile Leu Ile Arg Ala Leu
945                 950                 955                 960

Leu Val Ala Met Thr Gly Phe Lys Met Ala Thr Glu Leu Phe Thr Gln
                965                 970                 975

Met His Leu Arg Ile Phe Arg Ala Ser Met Ser Phe Phe Asp Ala Thr
            980                 985                 990

Pro Met Gly Arg Ile Leu Asn Arg  Ala Ser Thr Asp Gln  Ser Val Ala
        995                 1000                1005

Asp Leu  Arg Leu Pro Gly Gln  Phe Ala Tyr Val Ala  Ile Ala Ala
    1010                1015                1020

Ile Asn  Ile Leu Gly Ile Ile  Gly Val Ile Val Gln  Val Ala Trp
```

```
    1025                1030                1035

Gln Val  Leu Ile Val Phe Ile  Pro Val Val Ala Ala  Cys Ala Trp
    1040                1045                1050

Tyr Arg  Gln Tyr Tyr Ile Ser  Ala Ala Arg Glu Leu  Ala Arg Leu
    1055                1060                1065

Ala Gly  Ile Ser Arg Ser Pro  Val Val His His Phe  Ser Glu Thr
    1070                1075                1080

Leu Ser  Gly Ile Thr Thr Ile  Arg Ser Phe Asp Gln  Glu Pro Arg
    1085                1090                1095

Phe Arg  Gly Asp Ile Met Arg  Leu Ser Asp Cys Tyr  Ser Arg Leu
    1100                1105                1110

Lys Phe  His Ser Thr Gly Ala  Met Glu Trp Leu Cys  Phe Arg Leu
    1115                1120                1125

Glu Leu  Leu Ser Thr Phe Ala  Phe Ala Ser Ser Leu  Val Ile Leu
    1130                1135                1140

Val Ser  Ala Pro Glu Gly Val  Ile Asn Pro Ser Leu  Ala Gly Leu
    1145                1150                1155

Ala Ile  Thr Tyr Ala Leu Asn  Leu Asn Thr Leu Gln  Ala Thr Leu
    1160                1165                1170

Ile Trp  Thr Leu Cys Asp Leu  Glu Asn Lys Met Ile  Ser Val Glu
    1175                1180                1185

Arg Met  Leu Gln Tyr Thr Asn  Ile Pro Ser Glu Pro  Pro Leu Val
    1190                1195                1200

Ile Glu  Thr Thr Arg Pro Glu  Lys Ser Trp Pro Ser  Arg Gly Glu
    1205                1210                1215

Ile Thr  Ile Cys Asn Leu Gln  Val Arg Tyr Gly Pro  His Leu Pro
    1220                1225                1230

Met Val  Leu His Gly Leu Thr  Cys Thr Phe Pro Gly  Gly Leu Lys
    1235                1240                1245

Thr Gly  Ile Val Gly Arg Thr  Gly Cys Gly Lys Ser  Thr Leu Ile
    1250                1255                1260

Gln Thr  Leu Phe Arg Ile Val  Glu Pro Ala Ala Gly  Glu Ile Arg
    1265                1270                1275

Ile Asp  Gly Ile Asn Ile Leu  Ser Ile Gly Leu His  Asp Leu Arg
    1280                1285                1290

Ser Arg  Leu Ser Ile Ile Pro  Gln Asp Pro Thr Met  Phe Glu Gly
    1295                1300                1305

Thr Ile  Arg Ser Asn Leu Asp  Pro Leu Glu Glu Tyr  Thr Asp Asp
    1310                1315                1320

Gln Ile  Trp Glu Ala Leu Asp  Asn Cys Gln Leu Gly  Asp Glu Val
    1325                1330                1335

Arg Lys  Lys Glu Leu Lys Leu  Asp Ser Pro Val Ser  Glu Asn Gly
    1340                1345                1350

Gln Asn  Trp Ser Val Gly Gln  Arg Gln Leu Val Cys  Leu Gly Arg
    1355                1360                1365

Val Leu  Leu Lys Arg Ser Lys  Leu Leu Val Leu Asp  Glu Ala Thr
    1370                1375                1380

Ala Ser  Ile Asp Thr Ala Thr  Asp Asn Leu Ile Gln  Glu Thr Leu
    1385                1390                1395

Arg His  His Phe Ala Asp Cys  Thr Val Ile Thr Ile  Ala His Arg
    1400                1405                1410

Ile Ser  Ser Val Ile Asp Ser  Asp Met Val Leu Leu  Leu Asp Gln
    1415                1420                1425
```

Gly Leu Ile Lys Glu His Asp Ser Pro Ala Arg Leu Leu Glu Asp
1430 1435 1440

Arg Ser Ser Leu Phe Ser Lys Leu Val Ala Glu Tyr Thr Thr Ser
1445 1450 1455

Ser Glu Ser Lys Ser Lys Arg Ser
1460 1465

<210> SEQ ID NO 27
<211> LENGTH: 1491
<212> TYPE: DNA
<213> ORGANISM: Arabidopsis thaliana

<400> SEQUENCE: 27
atggagctag aatcttctcc tcctctacct cctcatgtga tgctcgtatc ttttccaggg 60
caaggccacg ttaatccact tcttcgtctt ggtaagctct tagcttcaaa gggtttgctc 120
ataaccttcg tcaccactga gtcatggggc aaaaagatgc gaatctccaa caaaatccaa 180
gaccgtgtcc tcaaaccggt tggtaaaggc tatctccggt atgatttctt cgacgacggg 240
cttcctgaag acgacgaagc tagcagaacc aacttaacca tcctccgacc acatctagag 300
ctggtcggca aaagagagat caagaacctt gtgaaacgtt acaaggaagt aacgaaacag 360
cccgtgacat gtcttatcaa caaccctttc gtctcttggg tctgtgacgt ggcagaagat 420
cttcaaatcc cttgtgctgt tctttgggtt caatcttgtg cctgcttagc tgcttattac 480
tattaccacc acaacctagt tgacttcccg accaaaacag aacccgagat cgatgtccaa 540
atctctggca tgcctctctt gaaacatgac gagatccctt ctttcattca cccttcaagt 600
cctcactccg ctttgcgaga agtgatcata gatcagatta aacggcttca caagactttc 660
tccattttca tcgacacttt caactcattg gagaaagaca tcattgacca catgtcgacg 720
ctctctctcc ccggtgttat cagaccgcta ggaccactct acaaaatggc taaaaccgta 780
gcttatgatg tcgttaaagt aaacatctct gagccaacgg atccttgcat ggagtggtta 840
gactcgcagc cagtttcctc cgttgtttac atctcattcg ggaccgttgc ttacttgaaa 900
caagaacaaa tagacgagat cgcttacggt gtgttaaacg ccgacgttac gttcttgtgg 960
gtgattagac aacaagagtt aggtttcaac aaagagaaac atgttttgcc ggaagaagtt 1020
aaagggaaag ggaagatcgt tgaatggtgt tcacaagaga aagtattatc tcatccttca 1080
gtggcatgtt tcgtgactca ctgtggatgg aactcaacga tggaagctgt gtcttccgga 1140
gtcccgacgg tttgttttcc tcaatgggga gatcaagtca cggacgccgt ttacatgatc 1200
gatgtttgga agacgggagt gaggctaagc cgtggagagg cggaggagag gttagtgccg 1260
agggaggaag ttgcggagag gttgagagag gttactaaag gagagaaagc gatcgagttg 1320
aaaaagaatg ctttgaagtg gaaggaagag gcggaggcgg cggttgctcg cggtggttcg 1380
tcggatagga atcttgaaaa gtttgtggag aagttgggtg ccaaacctgt ggggaaagta 1440
caaaacggga gtcataatca tgtcttggct ggatcaatca aaagctttta a 1491

<210> SEQ ID NO 28
<211> LENGTH: 496
<212> TYPE: PRT
<213> ORGANISM: Arabidopsis thaliana

<400> SEQUENCE: 28

Met Glu Leu Glu Ser Ser Pro Pro Leu Pro Pro His Val Met Leu Val
1 5 10 15

-continued

```
Ser Phe Pro Gly Gln Gly His Val Asn Pro Leu Leu Arg Leu Gly Lys
            20                  25                  30

Leu Leu Ala Ser Lys Gly Leu Leu Ile Thr Phe Val Thr Thr Glu Ser
        35                  40                  45

Trp Gly Lys Lys Met Arg Ile Ser Asn Lys Ile Gln Asp Arg Val Leu
    50                  55                  60

Lys Pro Val Gly Lys Gly Tyr Leu Arg Tyr Asp Phe Phe Asp Asp Gly
65                  70                  75                  80

Leu Pro Glu Asp Asp Glu Ala Ser Arg Thr Asn Leu Thr Ile Leu Arg
                85                  90                  95

Pro His Leu Glu Leu Val Gly Lys Arg Glu Ile Lys Asn Leu Val Lys
            100                 105                 110

Arg Tyr Lys Glu Val Thr Lys Gln Pro Val Thr Cys Leu Ile Asn Asn
        115                 120                 125

Pro Phe Val Ser Trp Val Cys Asp Val Ala Glu Asp Leu Gln Ile Pro
    130                 135                 140

Cys Ala Val Leu Trp Val Gln Ser Cys Ala Cys Leu Ala Ala Tyr Tyr
145                 150                 155                 160

Tyr Tyr His His Asn Leu Val Asp Phe Pro Thr Lys Thr Glu Pro Glu
                165                 170                 175

Ile Asp Val Gln Ile Ser Gly Met Pro Leu Leu Lys His Asp Glu Ile
            180                 185                 190

Pro Ser Phe Ile His Pro Ser Ser Pro His Ser Ala Leu Arg Glu Val
        195                 200                 205

Ile Ile Asp Gln Ile Lys Arg Leu His Lys Thr Phe Ser Ile Phe Ile
    210                 215                 220

Asp Thr Phe Asn Ser Leu Glu Lys Asp Ile Ile Asp His Met Ser Thr
225                 230                 235                 240

Leu Ser Leu Pro Gly Val Ile Arg Pro Leu Gly Pro Leu Tyr Lys Met
                245                 250                 255

Ala Lys Thr Val Ala Tyr Asp Val Val Lys Val Asn Ile Ser Glu Pro
            260                 265                 270

Thr Asp Pro Cys Met Glu Trp Leu Asp Ser Gln Pro Val Ser Ser Val
        275                 280                 285

Val Tyr Ile Ser Phe Gly Thr Val Ala Tyr Leu Lys Gln Glu Gln Ile
    290                 295                 300

Asp Glu Ile Ala Tyr Gly Val Leu Asn Ala Asp Val Thr Phe Leu Trp
305                 310                 315                 320

Val Ile Arg Gln Gln Glu Leu Gly Phe Asn Lys Glu Lys His Val Leu
                325                 330                 335

Pro Glu Glu Val Lys Gly Lys Gly Lys Ile Val Glu Trp Cys Ser Gln
            340                 345                 350

Glu Lys Val Leu Ser His Pro Ser Val Ala Cys Phe Val Thr His Cys
        355                 360                 365

Gly Trp Asn Ser Thr Met Glu Ala Val Ser Ser Gly Val Pro Thr Val
    370                 375                 380

Cys Phe Pro Gln Trp Gly Asp Gln Val Thr Asp Ala Val Tyr Met Ile
385                 390                 395                 400

Asp Val Trp Lys Thr Gly Val Arg Leu Ser Arg Gly Glu Ala Glu Glu
                405                 410                 415

Arg Leu Val Pro Arg Glu Glu Val Ala Glu Arg Leu Arg Glu Val Thr
            420                 425                 430

Lys Gly Glu Lys Ala Ile Glu Leu Lys Lys Asn Ala Leu Lys Trp Lys
```

-continued

```
        435                 440                 445

Glu Glu Ala Glu Ala Ala Val Ala Arg Gly Gly Ser Ser Asp Arg Asn
    450                 455                 460

Leu Glu Lys Phe Val Glu Lys Leu Gly Ala Lys Pro Val Gly Lys Val
465                 470                 475                 480

Gln Asn Gly Ser His Asn His Val Leu Ala Gly Ser Ile Lys Ser Phe
                485                 490                 495


<210> SEQ ID NO 29
<211> LENGTH: 3054
<212> TYPE: DNA
<213> ORGANISM: Arabidopsis thaliana

<400> SEQUENCE: 29

atgcggagaa acgtatctga tcatgcagag aagaaggaca aggtgggcgt tgaggttctt      60

ctggaacttc ccaaaaccct aagcaaatca aacaaaaaat ggcaattagc attgatcaag     120

ctctactgtt caagaactct cctcaattgc gccaaacacg ctatccgaaa acccggtttg     180

ttccctcgtt ctctttcata caccgccatt gatcttgatc accatcatgg agatgatcac     240

ttcaagattg atactgaaac cttaaacgat ctcgtcaaga acaagaacca agagaaactt     300

gagtctcttg gtggtcctaa tggcttagtc tcagctctca agagtaacac acgtctcggg     360

atcaacgaag aaggtgatga gattcaacgt agacgttcaa cgttcgggtc caacacttac     420

acaagacaac catcgaaggg tcttttccat tttgtggtgg aagctttcaa ggacttaacg     480

attcttatcc ttctcggttg cgcaacgctc tctctcgggt ttggtatcaa agagcatgga     540

ttaaaagaag gatggtacga tggaggaagt atattcgtag cggtttttctt ggtggtagct     600

gtctctgcgg tcagcaactt cagacagaac agacagtttg ataaactctc taaagtaagt     660

agtaacatta agatcgatgt tgttagaaac ggacgtcgtc aagagatttc gatctttgat     720

attgtcgttg gagatatcgt ttgtttgaac atcggagatc aagttccagc tgatggagtg     780

ttcgttgaag gacatttgtt acacgttgat gaatcaagca tgactggaga aagcgatcat     840

gtcgaggtta gcctaaccgg aaacacattt ttgttctccg ggactaaaat agctgatggg     900

ttcggtaaaa tggcggttac ttccgttggg atgaacacag cttggggaca aatgatgagt     960

catatctcgc gtgacactaa cgagcaaact ccgttgcagt ctcgtctcga taagcttact    1020

tcttccatag gtaaagttgg tttacttgta gctttcttgg ttcttttggt tctgttaatt    1080

cgttacttca cgggaaccac gaaagacgag agcggaaacc gtgagtataa cggaaagact    1140

acgaagagcg atgagatagt gaacgctgtg gttaagatgg ttgcagctgc ggttacaatc    1200

atcgtagttg cgatacctga aggattgcca ttagctgtga cattgacatt ggcgtattca    1260

atgaagagaa tgatgaaaga taatgctatg gtgagaaagc tctctgcttg tgagacaatg    1320

ggctctgcaa cggttatttg taccgataaa accggtactt tgacgcttaa ccagatgaag    1380

gtaaccgatt tctggttcgg tctcgaatca ggaaaagctt cttctgtgtc tcagagagtt    1440

gttgaattgt ttcatcaagg agttgcaatg aacactacag ggagtgtgtt taaggctaaa    1500

gcaggaacag agtatgagtt ctctggttct ccaacggaga aagcgattct tagctgggcg    1560

gttgaggaac tggagatggg tatggagaaa gtgattgaag aacatgatgt tgttcatgtg    1620

gaaggtttca attcagagaa gaagagaagt ggtgtgttga tgaagaagaa aggcgtaaac    1680

acagagaaca atgttgttca ttggaaagga gctgctgaga agattctagc tatgtgttca    1740

acgttctgtg atggttctgg agttgtgaga gagatgaaag aagatgataa gattcagttt    1800
```

```
gagaagatta ttcaatctat ggcagctaaa tctctccgtt gcatcgcctt tgcgtattca   1860
gaagacaatg aggacaacaa gaagttgaaa gaagagaagt tgagcttact tgggatcatt   1920
ggaatcaaag atccgtgtag accaggagtg aagaaagctg ttgaggattg tcaattcgcc   1980
ggtgtaaaca tcaaaatgat caccggggat aacattttca cggcgagagc aatagctgtt   2040
gagtgtggaa tcttgacacc tgaagatgag atgaatagtg aagctgtgtt agaaggagaa   2100
aagtttcgaa actacactca agaagaaaga ttagagaaag tcgaaagaat caaagtgatg   2160
gcgagatctt caccctttga taagcttctt atggtgaaat gtctcaagga gttaggtcat   2220
gtggtggcgg ttactggaga tggtactaac gatgcaccag cgttgaaaga agctgatatt   2280
ggactttcta tggggattca aggtacggaa gtagcgaaag agagctcaga tatcgtgatt   2340
cttgacgata actttgcttc tgttgcaacg gttttgaaat ggggaagatg cgtgtacaac   2400
aatattcaga agtttattca gtttcagctc actgtcaatg tagctgctct agtgatcaac   2460
ttcgtggctg cagtttcagc tggagacgtt cctttgacag cggttcagtt actgtgggtt   2520
aatctgatca tggacacact cggtgcattg gctttagcta cagagaagcc aacaaacgat   2580
cttatgaaga agaaaccgat agggagagtg gcgccattga tcacaaacat catgtggagg   2640
aatctactag ctcaagcgtt ttaccaaatc tctgtgctct tggtgcttca gtttagagga   2700
agatcgattt tcaacgtgac tgagaaagtg aagaacactt tgatcttcaa tacatttgtg   2760
ctttgtcagg tgttcaacga gtttaacgct aggagtttgg agaagaagaa tgtgtttaaa   2820
gggttacaca agaacagact cttcattgga attatagttg tgactgtggt tttgcaagtt   2880
gtgatggttg agtttctcaa gagatttgct gatacagaga ggctaaactt gggtcaatgg   2940
ggagtttgca ttgccatcgc agctgcatcg tggccgattg gatggttagt gaagtctgtt   3000
ccggttccag agagacactt ctttagctac ctgaaatgga agaagagatc atga         3054
```

<210> SEQ ID NO 30
<211> LENGTH: 1017
<212> TYPE: PRT
<213> ORGANISM: Arabidopsis thaliana

<400> SEQUENCE: 30

```
Met Arg Arg Asn Val Ser Asp His Ala Glu Lys Lys Asp Lys Val Gly
1               5                   10                  15

Val Glu Val Leu Leu Glu Leu Pro Lys Thr Leu Ser Lys Ser Asn Lys
            20                  25                  30

Lys Trp Gln Leu Ala Leu Ile Lys Leu Tyr Cys Ser Arg Thr Leu Leu
        35                  40                  45

Asn Cys Ala Lys His Ala Ile Arg Lys Pro Gly Leu Phe Pro Arg Ser
    50                  55                  60

Leu Ser Tyr Thr Ala Ile Asp Leu Asp His His His Gly Asp Asp His
65                  70                  75                  80

Phe Lys Ile Asp Thr Glu Thr Leu Asn Asp Leu Val Lys Asn Lys Asn
                85                  90                  95

Gln Glu Lys Leu Glu Ser Leu Gly Gly Pro Asn Gly Leu Val Ser Ala
            100                 105                 110

Leu Lys Ser Asn Thr Arg Leu Gly Ile Asn Glu Glu Gly Asp Glu Ile
        115                 120                 125

Gln Arg Arg Arg Ser Thr Phe Gly Ser Asn Thr Tyr Thr Arg Gln Pro
    130                 135                 140

Ser Lys Gly Leu Phe His Phe Val Val Glu Ala Phe Lys Asp Leu Thr
145                 150                 155                 160
```

```
Ile Leu Ile Leu Leu Gly Cys Ala Thr Leu Ser Leu Gly Phe Gly Ile
                165                 170                 175

Lys Glu His Gly Leu Lys Glu Gly Trp Tyr Asp Gly Gly Ser Ile Phe
            180                 185                 190

Val Ala Val Phe Leu Val Val Ala Val Ser Ala Val Ser Asn Phe Arg
        195                 200                 205

Gln Asn Arg Gln Phe Asp Lys Leu Ser Lys Val Ser Ser Asn Ile Lys
    210                 215                 220

Ile Asp Val Val Arg Asn Gly Arg Arg Gln Glu Ile Ser Ile Phe Asp
225                 230                 235                 240

Ile Val Val Gly Asp Ile Val Cys Leu Asn Ile Gly Asp Gln Val Pro
                245                 250                 255

Ala Asp Gly Val Phe Val Glu Gly His Leu Leu His Val Asp Glu Ser
            260                 265                 270

Ser Met Thr Gly Glu Ser Asp His Val Glu Val Ser Leu Thr Gly Asn
        275                 280                 285

Thr Phe Leu Phe Ser Gly Thr Lys Ile Ala Asp Gly Phe Gly Lys Met
    290                 295                 300

Ala Val Thr Ser Val Gly Met Asn Thr Ala Trp Gly Gln Met Met Ser
305                 310                 315                 320

His Ile Ser Arg Asp Thr Asn Glu Gln Thr Pro Leu Gln Ser Arg Leu
                325                 330                 335

Asp Lys Leu Thr Ser Ser Ile Gly Lys Val Gly Leu Leu Val Ala Phe
            340                 345                 350

Leu Val Leu Leu Val Leu Leu Ile Arg Tyr Phe Thr Gly Thr Thr Lys
        355                 360                 365

Asp Glu Ser Gly Asn Arg Glu Tyr Asn Gly Lys Thr Thr Lys Ser Asp
    370                 375                 380

Glu Ile Val Asn Ala Val Val Lys Met Val Ala Ala Ala Val Thr Ile
385                 390                 395                 400

Ile Val Val Ala Ile Pro Glu Gly Leu Pro Leu Ala Val Thr Leu Thr
                405                 410                 415

Leu Ala Tyr Ser Met Lys Arg Met Met Lys Asp Asn Ala Met Val Arg
            420                 425                 430

Lys Leu Ser Ala Cys Glu Thr Met Gly Ser Ala Thr Val Ile Cys Thr
        435                 440                 445

Asp Lys Thr Gly Thr Leu Thr Leu Asn Gln Met Lys Val Thr Asp Phe
    450                 455                 460

Trp Phe Gly Leu Glu Ser Gly Lys Ala Ser Ser Val Ser Gln Arg Val
465                 470                 475                 480

Val Glu Leu Phe His Gln Gly Val Ala Met Asn Thr Thr Gly Ser Val
                485                 490                 495

Phe Lys Ala Lys Ala Gly Thr Glu Tyr Glu Phe Ser Gly Ser Pro Thr
            500                 505                 510

Glu Lys Ala Ile Leu Ser Trp Ala Val Glu Glu Leu Glu Met Gly Met
        515                 520                 525

Glu Lys Val Ile Glu Glu His Asp Val Val His Val Glu Gly Phe Asn
    530                 535                 540

Ser Glu Lys Lys Arg Ser Gly Val Leu Met Lys Lys Lys Gly Val Asn
545                 550                 555                 560

Thr Glu Asn Asn Val Val His Trp Lys Gly Ala Ala Glu Lys Ile Leu
                565                 570                 575
```

-continued

```
Ala Met Cys Ser Thr Phe Cys Asp Gly Ser Gly Val Val Arg Glu Met
            580                 585                 590

Lys Glu Asp Asp Lys Ile Gln Phe Glu Lys Ile Ile Gln Ser Met Ala
        595                 600                 605

Ala Lys Ser Leu Arg Cys Ile Ala Phe Ala Tyr Ser Glu Asp Asn Glu
    610                 615                 620

Asp Asn Lys Lys Leu Lys Glu Glu Lys Leu Ser Leu Leu Gly Ile Ile
625                 630                 635                 640

Gly Ile Lys Asp Pro Cys Arg Pro Gly Val Lys Lys Ala Val Glu Asp
                645                 650                 655

Cys Gln Phe Ala Gly Val Asn Ile Lys Met Ile Thr Gly Asp Asn Ile
            660                 665                 670

Phe Thr Ala Arg Ala Ile Ala Val Glu Cys Gly Ile Leu Thr Pro Glu
        675                 680                 685

Asp Glu Met Asn Ser Glu Ala Val Leu Glu Gly Glu Lys Phe Arg Asn
    690                 695                 700

Tyr Thr Gln Glu Glu Arg Leu Glu Lys Val Glu Arg Ile Lys Val Met
705                 710                 715                 720

Ala Arg Ser Ser Pro Phe Asp Lys Leu Leu Met Val Lys Cys Leu Lys
                725                 730                 735

Glu Leu Gly His Val Val Ala Val Thr Gly Asp Gly Thr Asn Asp Ala
            740                 745                 750

Pro Ala Leu Lys Glu Ala Asp Ile Gly Leu Ser Met Gly Ile Gln Gly
        755                 760                 765

Thr Glu Val Ala Lys Glu Ser Ser Asp Ile Val Ile Leu Asp Asp Asn
    770                 775                 780

Phe Ala Ser Val Ala Thr Val Leu Lys Trp Gly Arg Cys Val Tyr Asn
785                 790                 795                 800

Asn Ile Gln Lys Phe Ile Gln Phe Gln Leu Thr Val Asn Val Ala Ala
                805                 810                 815

Leu Val Ile Asn Phe Val Ala Ala Val Ser Ala Gly Asp Val Pro Leu
            820                 825                 830

Thr Ala Val Gln Leu Leu Trp Val Asn Leu Ile Met Asp Thr Leu Gly
        835                 840                 845

Ala Leu Ala Leu Ala Thr Glu Lys Pro Thr Asn Asp Leu Met Lys Lys
    850                 855                 860

Lys Pro Ile Gly Arg Val Ala Pro Leu Ile Thr Asn Ile Met Trp Arg
865                 870                 875                 880

Asn Leu Leu Ala Gln Ala Phe Tyr Gln Ile Ser Val Leu Leu Val Leu
                885                 890                 895

Gln Phe Arg Gly Arg Ser Ile Phe Asn Val Thr Glu Lys Val Lys Asn
            900                 905                 910

Thr Leu Ile Phe Asn Thr Phe Val Leu Cys Gln Val Phe Asn Glu Phe
        915                 920                 925

Asn Ala Arg Ser Leu Glu Lys Lys Asn Val Phe Lys Gly Leu His Lys
    930                 935                 940

Asn Arg Leu Phe Ile Gly Ile Ile Val Val Thr Val Val Leu Gln Val
945                 950                 955                 960

Val Met Val Glu Phe Leu Lys Arg Phe Ala Asp Thr Glu Arg Leu Asn
                965                 970                 975

Leu Gly Gln Trp Gly Val Cys Ile Ala Ile Ala Ala Ala Ser Trp Pro
            980                 985                 990

Ile Gly Trp Leu Val Lys Ser Val  Pro Val Pro Glu Arg  His Phe Phe
```

-continued

```
        995                 1000                1005

Ser Tyr  Leu Lys Trp Lys Lys  Arg Ser
    1010                1015
```

<210> SEQ ID NO 31
<211> LENGTH: 1995
<212> TYPE: DNA
<213> ORGANISM: Arabidopsis thaliana

<400> SEQUENCE: 31

```
atggcttgta gactatattt ggctttgatc ttctcttgcg tttatctgat ttgcctgtca     60

agtcaacaag aaaccgggtt tgtctacaat ggcttcgagc aagcagatct ttttattgat    120

gggatcgcca aaatactacc tgatgggctt ttgcagttga caaatactac agagttgcaa    180

atgggtcatg ctttcttcaa gaagccgttt gattttgatc catcttcatc actatcgttc    240

tatacacatt ttgtgtgtgc gcttgtgcct cctaagttgg gagctgatgg tggccatggg    300

attgtctttg ttgtatctcc ttccattgat ctctctcatg catacgcaac tcagtacttg    360

ggggtcttca gcaacttaac aaatgggact tcctcttcac atctgctagc tattgagctc    420

gataccgtta agacagtaga gtttaatgag ctggagaagc ctcatgttgg tattgatttg    480

aacagcccaa tatctgttga atctgctctg ccatcttact tttccaacgc tttggggaag    540

aatataagca taaatcttct tagtggggag cctatacagg tctgggtaga ttacgatggc    600

tcgtttctaa atgttacact ggcccctata gaaatcaaga agccaaatca gcctcttata    660

tcaagagcca tcaatctttc agaaatcttt caagagaaga tgtatgttgg gttctcttca    720

tcaacaggga atcttctcag taaccattat atacttggat ggagttttag tagaagaaaa    780

gaacaattac agagcctgaa cctctctaca cttcctcggg ttcctcttcc taaagaggaa    840

aaaaagaaat tatctccatt acttattggt ttggtcatct tattagtgat tcctgtggtg    900

atggttcttg gaggagttta ttggtacagg agaaagaaat atgcagaagt aaaagaatgg    960

tgggaaaagg aatacggccc acaccgattc tcctataagt ctctgtacaa agcaacaaat   1020

gggtttcgta aagattgtcg tgttgggaaa ggtgggtttg gagaagtcta caaaggaact   1080

ttgcccggag gcaggcatat agctgtgaaa agactatccc acgatgcaga gcaagggatg   1140

aaacagtttg tggcagaagt tgtaaccatg ggaaatttac aacatcggaa cttggttcct   1200

cttctcgggt attgcaggag aaaatgtgag ttacttttgg tgtctgagta catgcccaac   1260

ggtagccttg accagtactt gtttcatgag ggaaacccat ctccttcatg gtatcaaaga   1320

atttctattc ttaaggacat tgcctcagct ctcagttact tgcatacagg aaccaagcaa   1380

gttgttttgc accgggatat aaaagcttct aacgtcatgt tggattccga gttcaacggg   1440

aggttaggtg attttggaat ggccaagttt cacgaccgtg gaaccaactt atctgcaaca   1500

gccgctgtgg gaaccatagg ttacatggca cctgaactaa taacaatggg cacgtctatg   1560

aaaaccgatg tgtatgcttt tggtgctttt cttcttgaag taatttgtgg caggcgacca   1620

gtggaacctg agctaccagt cggaaagcaa tatttggtca agtgggtcta tgaatgctgg   1680

aaagaggctt gcttattcaa gaccagagat ccaagattgg gagtagaatt cttacccgag   1740

gaagtcgaga tggttctgaa acttgggtta ctctgcacaa atgctatgcc agaatcaagg   1800

cctgcgatgg aacaagtggt gcaatacctt aaccaagact taccccttacc gattttctcg   1860

ccgtctactc caggtatcgg ggcttttatg ccagtttcta tggaagcatt atctgccatt   1920

ggggtctcca gtgtaaggaa ctcatcagtt tctatgtttg ttactcacac aatcttggac   1980
```

-continued

```
gggcatggaa gataa                                                    1995


<210> SEQ ID NO 32
<211> LENGTH: 664
<212> TYPE: PRT
<213> ORGANISM: Arabidopsis thaliana

<400> SEQUENCE: 32

Met Ala Cys Arg Leu Tyr Leu Ala Leu Ile Phe Ser Cys Val Tyr Leu
1               5                   10                  15

Ile Cys Leu Ser Ser Gln Gln Glu Thr Gly Phe Val Tyr Asn Gly Phe
            20                  25                  30

Glu Gln Ala Asp Leu Phe Ile Asp Gly Ile Ala Lys Ile Leu Pro Asp
        35                  40                  45

Gly Leu Leu Gln Leu Thr Asn Thr Thr Glu Leu Gln Met Gly His Ala
    50                  55                  60

Phe Phe Lys Lys Pro Phe Asp Phe Asp Pro Ser Ser Ser Leu Ser Phe
65                  70                  75                  80

Tyr Thr His Phe Val Cys Ala Leu Val Pro Pro Lys Leu Gly Ala Asp
                85                  90                  95

Gly Gly His Gly Ile Val Phe Val Val Ser Pro Ser Ile Asp Leu Ser
            100                 105                 110

His Ala Tyr Ala Thr Gln Tyr Leu Gly Val Phe Ser Asn Leu Thr Asn
        115                 120                 125

Gly Thr Ser Ser Ser His Leu Leu Ala Ile Glu Leu Asp Thr Val Lys
    130                 135                 140

Thr Val Glu Phe Asn Glu Leu Glu Lys Pro His Val Gly Ile Asp Leu
145                 150                 155                 160

Asn Ser Pro Ile Ser Val Glu Ser Ala Leu Pro Ser Tyr Phe Ser Asn
                165                 170                 175

Ala Leu Gly Lys Asn Ile Ser Ile Asn Leu Leu Ser Gly Glu Pro Ile
            180                 185                 190

Gln Val Trp Val Asp Tyr Asp Gly Ser Phe Leu Asn Val Thr Leu Ala
        195                 200                 205

Pro Ile Glu Ile Lys Lys Pro Asn Gln Pro Leu Ile Ser Arg Ala Ile
    210                 215                 220

Asn Leu Ser Glu Ile Phe Gln Glu Lys Met Tyr Val Gly Phe Ser Ser
225                 230                 235                 240

Ser Thr Gly Asn Leu Leu Ser Asn His Tyr Ile Leu Gly Trp Ser Phe
                245                 250                 255

Ser Arg Arg Lys Glu Gln Leu Gln Ser Leu Asn Leu Ser Thr Leu Pro
            260                 265                 270

Arg Val Pro Leu Pro Lys Glu Glu Lys Lys Lys Leu Ser Pro Leu Leu
        275                 280                 285

Ile Gly Leu Val Ile Leu Leu Val Ile Pro Val Val Met Val Leu Gly
    290                 295                 300

Gly Val Tyr Trp Tyr Arg Arg Lys Lys Tyr Ala Glu Val Lys Glu Trp
305                 310                 315                 320

Trp Glu Lys Glu Tyr Gly Pro His Arg Phe Ser Tyr Lys Ser Leu Tyr
                325                 330                 335

Lys Ala Thr Asn Gly Phe Arg Lys Asp Cys Arg Val Gly Lys Gly Gly
            340                 345                 350

Phe Gly Glu Val Tyr Lys Gly Thr Leu Pro Gly Gly Arg His Ile Ala
        355                 360                 365
```

```
Val Lys Arg Leu Ser His Asp Ala Glu Gln Gly Met Lys Gln Phe Val
    370                 375                 380

Ala Glu Val Val Thr Met Gly Asn Leu Gln His Arg Asn Leu Val Pro
385                 390                 395                 400

Leu Leu Gly Tyr Cys Arg Arg Lys Cys Glu Leu Leu Leu Val Ser Glu
                405                 410                 415

Tyr Met Pro Asn Gly Ser Leu Asp Gln Tyr Leu Phe His Glu Gly Asn
            420                 425                 430

Pro Ser Pro Ser Trp Tyr Gln Arg Ile Ser Ile Leu Lys Asp Ile Ala
        435                 440                 445

Ser Ala Leu Ser Tyr Leu His Thr Gly Thr Lys Gln Val Val Leu His
    450                 455                 460

Arg Asp Ile Lys Ala Ser Asn Val Met Leu Asp Ser Glu Phe Asn Gly
465                 470                 475                 480

Arg Leu Gly Asp Phe Gly Met Ala Lys Phe His Asp Arg Gly Thr Asn
                485                 490                 495

Leu Ser Ala Thr Ala Ala Val Gly Thr Ile Gly Tyr Met Ala Pro Glu
            500                 505                 510

Leu Ile Thr Met Gly Thr Ser Met Lys Thr Asp Val Tyr Ala Phe Gly
        515                 520                 525

Ala Phe Leu Leu Glu Val Ile Cys Gly Arg Arg Pro Val Glu Pro Glu
    530                 535                 540

Leu Pro Val Gly Lys Gln Tyr Leu Val Lys Trp Val Tyr Glu Cys Trp
545                 550                 555                 560

Lys Glu Ala Cys Leu Phe Lys Thr Arg Asp Pro Arg Leu Gly Val Glu
                565                 570                 575

Phe Leu Pro Glu Glu Val Glu Met Val Leu Lys Leu Gly Leu Leu Cys
            580                 585                 590

Thr Asn Ala Met Pro Glu Ser Arg Pro Ala Met Glu Gln Val Val Gln
        595                 600                 605

Tyr Leu Asn Gln Asp Leu Pro Leu Pro Ile Phe Ser Pro Ser Thr Pro
    610                 615                 620

Gly Ile Gly Ala Phe Met Pro Val Ser Met Glu Ala Leu Ser Ala Ile
625                 630                 635                 640

Gly Val Ser Ser Val Arg Asn Ser Ser Val Ser Met Phe Val Thr His
                645                 650                 655

Thr Ile Leu Asp Gly His Gly Arg
            660
```

<210> SEQ ID NO 33
<211> LENGTH: 546
<212> TYPE: DNA
<213> ORGANISM: Arabidopsis thaliana

<400> SEQUENCE: 33

```
atgcagctca aatcatcatc accatcttct tcttcttctt cttcatcatc atccatgaaa      60

ctcaaaactc taatccaaaa cctcctcaca caccctctct accgtttcct aagagctctt     120

gcgaaagcca aatcaatctt tctagagatc tcaaaacaca acagcaacaa caagaaacga     180

aaactcatga tgctttttcc aacaaaggct tcaaagaacc aacgcaagat cttcttcgga     240

tctttcagat tgcattacaa ctggtgttcc tctcatgttg ttcctgtccc tcaaccgttt     300

cctttccctt cttcttacat caatggtgaa gaagaagatg attctcagct ttctggctac     360

ctcgagtggc ttgaacacaa gaagttcgat gatgtggaag agatcggaga tgttgtagct     420
```

```
gatggtggtg atgacgatat tgatcatttg gcggatatgt tcatcgctaa ttgccacgag    480

aagttcttgc tcgagaaagt tgaatcttac cggagatttc aagaaatgtt agaaaggggt    540

ttgtga                                                               546
```

<210> SEQ ID NO 34
<211> LENGTH: 181
<212> TYPE: PRT
<213> ORGANISM: Arabidopsis thaliana

<400> SEQUENCE: 34

```
Met Gln Leu Lys Ser Ser Ser Pro Ser Ser Ser Ser Ser Ser Ser Ser
1               5                   10                  15

Ser Ser Met Lys Leu Lys Thr Leu Ile Gln Asn Leu Leu Thr His Pro
            20                  25                  30

Leu Tyr Arg Phe Leu Arg Ala Leu Ala Lys Ala Lys Ser Ile Phe Leu
        35                  40                  45

Glu Ile Ser Lys His Asn Ser Asn Asn Lys Lys Arg Lys Leu Met Met
    50                  55                  60

Leu Phe Pro Thr Lys Ala Ser Lys Asn Gln Arg Lys Ile Phe Phe Gly
65                  70                  75                  80

Ser Phe Arg Leu His Tyr Asn Trp Cys Ser Ser His Val Val Pro Val
                85                  90                  95

Pro Gln Pro Phe Pro Phe Pro Ser Ser Tyr Ile Asn Gly Glu Glu Glu
            100                 105                 110

Asp Asp Ser Gln Leu Ser Gly Tyr Leu Glu Trp Leu Glu His Lys Lys
        115                 120                 125

Phe Asp Asp Val Glu Glu Ile Gly Asp Val Val Ala Asp Gly Gly Asp
    130                 135                 140

Asp Asp Ile Asp His Leu Ala Asp Met Phe Ile Ala Asn Cys His Glu
145                 150                 155                 160

Lys Phe Leu Leu Glu Lys Val Glu Ser Tyr Arg Arg Phe Gln Glu Met
                165                 170                 175

Leu Glu Arg Gly Leu
            180
```

<210> SEQ ID NO 35
<211> LENGTH: 1947
<212> TYPE: DNA
<213> ORGANISM: Arabidopsis thaliana

<400> SEQUENCE: 35

```
atgaagaact ctgctgcgat cttccttact tcttccctta ttcttctcct tcaaaccctc     60

cacggagtta aagccggttt catctgcgtc ggaagctcct tccccaccaa cagtagctac    120

caaaaaaacc gtgactctct cttctctact ctttctgata aagtcaccac aaacggtgga    180

ttctacaatg cttcactcga tggagttcac gttgttggcc tctgtagaag agactacgat    240

cggcaaggtt gtatcaactg cgtagaagaa tccattcgac agattaaaac aagttgttct    300

aatcgtgttc agtcgttcca ttgcaatagt gacgatagag aacgtgtttc ttgtcttgta    360

cgtaccacgg atcaatcaac ttatcggata ctcgagcttg gaccagctac gaatgacccg    420

agtcctgttg ctatcgacac attcgcaaag aacatgaccc ttttccgcca agaatgggaa    480

gcaatggttg accggacgct cgaggctgta accattgaca attccacaac ggttctcaag    540

tattacggtg ctctcaaatc agagttcagt gagtttccaa atgtatatat gatgatgcaa    600

tgcacacccg acataaattc aggcgcgtgc aagagatgtt tgcaagcgtc cgttacatat    660
```

-continued

```
tttagagacc agaattgggg cagacaagga ggcgggattt gtcgaccgag ctgtgttttc    720

aggtgggagt tttatccctt ttacggcgct tttgctaatg taacaagagt tccagcgcct    780

cctcgagctt tgattcctcg aacagaagca atctccatca ctcgcttgaa aggaggaatt    840

atcgcaatat ttgtggttcc tatcgtcatt aatcttctcg tctttatcgg tctgatcaga    900

gcatatactc gaataagaaa atcgtacaac ggaatcaatg aggcgcaata tgattatggt    960

ggtcagtcta agctacggtt cgattttcgc atgatcctaa cggcaaccga tgatttttcc   1020

tttgaaaata agattggcca aggtggattt ggatctgtct acaaggggaa attaccggga   1080

ggggaagaga tagcggtaaa aagattaaca agaggctcag gacaaggaga gatagagttt   1140

agaaacgagg tcttactctt gacaagactc caacatagga atctagttaa gcttcttgga   1200

ttttgtaatg aaggcgatga agagattctt gtttacgagt ttgtccccaa ttcaagcctc   1260

gaccacttca tatttgatga agagaagcgt ttgcttctaa cgtgggacat gagagccaga   1320

attatagaag gcgttgcgcg aggtcttgtt tatttacacg aagattctca gctgaggata   1380

attcaccgag acttgaaagc aagcaatatc cttttagatg catatatgaa ccctaaagtt   1440

gcagactttg ggatggcgag gttgttcaac atggaccaga ctcgagcagt gacaagaaaa   1500

gtagttggaa cctttggcta tatggctccc gagtacgtta ggaacagaac attttcagtc   1560

aagacagacg tttacagctt cggagtcgtg cttctcgaga tgataaccgg tcgaagtaac   1620

aagaactatt tcgaagccct cggcctccct gcatatgcat ggaagtgttg ggttgcgggc   1680

gaggcagcga gtatcatcga tcatgtcctc agtaggagcc gaagcaacga aatcatgaga   1740

ttcatccaca ttggtttgtt gtgtgttcaa gagaatgttt caaaaagacc aaccatgagt   1800

ttggttattc aatggcttgg aagtgagact atcgccattc ctttacctac agttgctggt   1860

tttacgaatg catcgtatca agctgaacat gaagctggta cattatcact aaatgagctt   1920

tcaatcaccg agttaagtcc tcgttga                                       1947
```

```
<210> SEQ ID NO 36
<211> LENGTH: 648
<212> TYPE: PRT
<213> ORGANISM: Arabidopsis thaliana

<400> SEQUENCE: 36

Met Lys Asn Ser Ala Ala Ile Phe Leu Thr Ser Ser Leu Ile Leu Leu
1               5                   10                  15

Leu Gln Thr Leu His Gly Val Lys Ala Gly Phe Ile Cys Val Gly Ser
            20                  25                  30

Ser Phe Pro Thr Asn Ser Ser Tyr Gln Lys Asn Arg Asp Ser Leu Phe
        35                  40                  45

Ser Thr Leu Ser Asp Lys Val Thr Thr Asn Gly Gly Phe Tyr Asn Ala
    50                  55                  60

Ser Leu Asp Gly Val His Val Val Gly Leu Cys Arg Arg Asp Tyr Asp
65                  70                  75                  80

Arg Gln Gly Cys Ile Asn Cys Val Glu Glu Ser Ile Arg Gln Ile Lys
                85                  90                  95

Thr Ser Cys Ser Asn Arg Val Gln Ser Phe His Cys Asn Ser Asp Asp
            100                 105                 110

Arg Glu Arg Val Ser Cys Leu Val Arg Thr Thr Asp Gln Ser Thr Tyr
        115                 120                 125

Arg Ile Leu Glu Leu Gly Pro Ala Thr Asn Asp Pro Ser Pro Val Ala
    130                 135                 140
```

-continued

```
Ile Asp Thr Phe Ala Lys Asn Met Thr Leu Phe Arg Gln Glu Trp Glu
145                 150                 155                 160

Ala Met Val Asp Arg Thr Leu Glu Ala Val Thr Ile Asp Asn Ser Thr
                165                 170                 175

Thr Val Leu Lys Tyr Tyr Gly Ala Leu Lys Ser Glu Phe Ser Glu Phe
            180                 185                 190

Pro Asn Val Tyr Met Met Met Gln Cys Thr Pro Asp Ile Asn Ser Gly
        195                 200                 205

Ala Cys Lys Arg Cys Leu Gln Ala Ser Val Thr Tyr Phe Arg Asp Gln
    210                 215                 220

Asn Trp Gly Arg Gln Gly Gly Gly Ile Cys Arg Pro Ser Cys Val Phe
225                 230                 235                 240

Arg Trp Glu Phe Tyr Pro Phe Tyr Gly Ala Phe Ala Asn Val Thr Arg
                245                 250                 255

Val Pro Ala Pro Pro Arg Ala Leu Ile Pro Arg Thr Glu Ala Ile Ser
            260                 265                 270

Ile Thr Arg Leu Lys Gly Gly Ile Ile Ala Ile Phe Val Val Pro Ile
        275                 280                 285

Val Ile Asn Leu Leu Val Phe Ile Gly Leu Ile Arg Ala Tyr Thr Arg
    290                 295                 300

Ile Arg Lys Ser Tyr Asn Gly Ile Asn Glu Ala Gln Tyr Asp Tyr Gly
305                 310                 315                 320

Gly Gln Ser Lys Leu Arg Phe Asp Phe Arg Met Ile Leu Thr Ala Thr
                325                 330                 335

Asp Asp Phe Ser Phe Glu Asn Lys Ile Gly Gln Gly Gly Phe Gly Ser
            340                 345                 350

Val Tyr Lys Gly Lys Leu Pro Gly Gly Glu Glu Ile Ala Val Lys Arg
        355                 360                 365

Leu Thr Arg Gly Ser Gly Gln Gly Glu Ile Glu Phe Arg Asn Glu Val
    370                 375                 380

Leu Leu Leu Thr Arg Leu Gln His Arg Asn Leu Val Lys Leu Leu Gly
385                 390                 395                 400

Phe Cys Asn Glu Gly Asp Glu Glu Ile Leu Val Tyr Glu Phe Val Pro
                405                 410                 415

Asn Ser Ser Leu Asp His Phe Ile Phe Asp Glu Glu Lys Arg Leu Leu
            420                 425                 430

Leu Thr Trp Asp Met Arg Ala Arg Ile Ile Glu Gly Val Ala Arg Gly
        435                 440                 445

Leu Val Tyr Leu His Glu Asp Ser Gln Leu Arg Ile Ile His Arg Asp
    450                 455                 460

Leu Lys Ala Ser Asn Ile Leu Leu Asp Ala Tyr Met Asn Pro Lys Val
465                 470                 475                 480

Ala Asp Phe Gly Met Ala Arg Leu Phe Asn Met Asp Gln Thr Arg Ala
                485                 490                 495

Val Thr Arg Lys Val Val Gly Thr Phe Gly Tyr Met Ala Pro Glu Tyr
            500                 505                 510

Val Arg Asn Arg Thr Phe Ser Val Lys Thr Asp Val Tyr Ser Phe Gly
        515                 520                 525

Val Val Leu Leu Glu Met Ile Thr Gly Arg Ser Asn Lys Asn Tyr Phe
    530                 535                 540

Glu Ala Leu Gly Leu Pro Ala Tyr Ala Trp Lys Cys Trp Val Ala Gly
545                 550                 555                 560
```

-continued

```
Glu Ala Ala Ser Ile Ile Asp His Val Leu Ser Arg Ser Arg Ser Asn
                565                 570                 575

Glu Ile Met Arg Phe Ile His Ile Gly Leu Leu Cys Val Gln Glu Asn
            580                 585                 590

Val Ser Lys Arg Pro Thr Met Ser Leu Val Ile Gln Trp Leu Gly Ser
        595                 600                 605

Glu Thr Ile Ala Ile Pro Leu Pro Thr Val Ala Gly Phe Thr Asn Ala
    610                 615                 620

Ser Tyr Gln Ala Glu His Glu Ala Gly Thr Leu Ser Leu Asn Glu Leu
625                 630                 635                 640

Ser Ile Thr Glu Leu Ser Pro Arg
                645


<210> SEQ ID NO 37
<211> LENGTH: 2160
<212> TYPE: DNA
<213> ORGANISM: Arabidopsis thaliana

<400> SEQUENCE: 37

atgaagatga caatatggag cttgtgttta atcttgtccc tttctaattc aaaactggtt     60

ttggcttctc atgttaagca cttatgtcgt caagaccaga agaatgctct tttggagttt    120

aagaacgagt tttatgtcca tgagttcaac tccaatggga ttgttggtgt taagaagaca    180

gagaagtgga ggaacaacac cgattgctgt tcttgggatg gtatctcttg tgatcctaaa    240

acgggtaagg tggtagagtt agacctcatg aacagttttc ttaatggtcc tttgagatat    300

gatagtagct tgtttagact acaacatctt cataatctgg atcttggctc gaataatttt    360

tcgggtattc taccggattc cataggcagc ctcaaatatt tgagggtttt gagtcttggt    420

gattgtaatc tctttggaaa gattccttct tcacttggaa atcttactta tctcactaat    480

cttgatcttt ctgttaatga tttcaccggg gagctaccgg attcgatggg acatttaaac    540

aagctaacag agttgcatct tggatcggcc aagctcagtg ggaactttcc tagtatgcta    600

ctcaatttga gcgagcttac gttgatcgac cttggttcta accagttcgg aggtatgctc    660

ccatctaata tgagtagcct ctctaaattg gtgtattttg ggattgatag aaattcattt    720

tccggatcta tcccatcgtc tctcttcatg ctaccttcat tgacctctct tgttttggga    780

agaaacgact tcaacggtcc tcttgacttt ggtaatatct cttcaccatc taatcttgga    840

gttttgtccc ttctagaaaa caatttcaat gggccaatcc cggagtctat atcgaaacta    900

gttggtctct tttatcttga cctctcttta tggaacacaa agagaggcat ggtcgatttc    960

aacactttct tgcatctcaa gtcacttacg ttccttgacc tctcttatat taatacaaga   1020

agcatggttg acataagtat attctcacct ctcttgtcac ttggttattt ggatctttcc   1080

gggattaatt tgaagatcag ttcaactcta agtcttccct cacccatggg caccttgatt   1140

ttatcatctt gcaatattcc tgagttcccc aattttctag aaaaccaaac cactttgtat   1200

tatttagaca tctctgccaa taaaattgga ggccaagtac cacaatggtt gtggagtcta   1260

ccggagttgc agtatgttaa catttctcaa aattctttca gtggctttga aggaccagca   1320

gatgttattc aaagatgtgg agaattactt atgcttgaca taagttcaaa cacattccaa   1380

gatccgtttc ctttgttacc aaactcgaca acgatctttt taggctctga taatcggttt   1440

tcgggagaga ttcctaagac tatatgcaaa ttggtttctc ttgatacact tgttttatcc   1500

aacaacaact tcaacggctc cattcctcgg tgtttcgaga agtttaatac tactctttcg   1560

gttttgcatc ttcggaataa caacttatcc ggtgagtttc cagaggaatc tatcagtgat   1620
```

```
cacttgagat cacttgacgt tggtcgcaac cggttatcag gagaacttcc caagtctttg   1680

atcaactgca ctcgtctcga gtttctgaac gtggaagaca acataatcaa tgacaagttt   1740

ccattctggt tgagaatgtt gcccaaactt cagatttttg tccttcgttc taacgagttt   1800

catggtccaa tatcttctct tggagattct ttgagcttcc ccaagctgcg aatctttgac   1860

atttcggaaa accgcttcaa tggagtcctt cgatcagatt tctttgcggg ttggagtgca   1920

atgtcatcag ccgtagacat cgtagatatt atgccgagta ggtatgctgg acgtgactca   1980

ggaaactatt ataactcagt gactatgacg gtcaaaggat cgataataga gttggttggg   2040

agtgttttca cgatttacaa aaccatcgat gtctccggaa acagattcga aggacgtatt   2100

cccgagtcaa tcggtttact taaagaactg attgtgctca atatgtcaaa caacggttga   2160
```

```
<210> SEQ ID NO 38
<211> LENGTH: 719
<212> TYPE: PRT
<213> ORGANISM: Arabidopsis thaliana

<400> SEQUENCE: 38

Met Lys Met Thr Ile Trp Ser Leu Cys Leu Ile Leu Ser Leu Ser Asn
1               5                   10                  15

Ser Lys Leu Val Leu Ala Ser His Val Lys His Leu Cys Arg Gln Asp
            20                  25                  30

Gln Lys Asn Ala Leu Leu Glu Phe Lys Asn Glu Phe Tyr Val His Glu
        35                  40                  45

Phe Asn Ser Asn Gly Ile Val Gly Val Lys Lys Thr Glu Lys Trp Arg
    50                  55                  60

Asn Asn Thr Asp Cys Cys Ser Trp Asp Gly Ile Ser Cys Asp Pro Lys
65                  70                  75                  80

Thr Gly Lys Val Val Glu Leu Asp Leu Met Asn Ser Phe Leu Asn Gly
                85                  90                  95

Pro Leu Arg Tyr Asp Ser Ser Leu Phe Arg Leu Gln His Leu His Asn
            100                 105                 110

Leu Asp Leu Gly Ser Asn Asn Phe Ser Gly Ile Leu Pro Asp Ser Ile
        115                 120                 125

Gly Ser Leu Lys Tyr Leu Arg Val Leu Ser Leu Gly Asp Cys Asn Leu
    130                 135                 140

Phe Gly Lys Ile Pro Ser Ser Leu Gly Asn Leu Thr Tyr Leu Thr Asn
145                 150                 155                 160

Leu Asp Leu Ser Val Asn Asp Phe Thr Gly Glu Leu Pro Asp Ser Met
                165                 170                 175

Gly His Leu Asn Lys Leu Thr Glu Leu His Leu Gly Ser Ala Lys Leu
            180                 185                 190

Ser Gly Asn Phe Pro Ser Met Leu Leu Asn Leu Ser Glu Leu Thr Leu
        195                 200                 205

Ile Asp Leu Gly Ser Asn Gln Phe Gly Gly Met Leu Pro Ser Asn Met
    210                 215                 220

Ser Ser Leu Ser Lys Leu Val Tyr Phe Gly Ile Asp Arg Asn Ser Phe
225                 230                 235                 240

Ser Gly Ser Ile Pro Ser Ser Leu Phe Met Leu Pro Ser Leu Thr Ser
                245                 250                 255

Leu Val Leu Gly Arg Asn Asp Phe Asn Gly Pro Leu Asp Phe Gly Asn
            260                 265                 270

Ile Ser Ser Pro Ser Asn Leu Gly Val Leu Ser Leu Leu Glu Asn Asn
```

-continued

```
        275                 280                 285

Phe Asn Gly Pro Ile Pro Glu Ser Ile Ser Lys Leu Val Gly Leu Phe
    290                 295                 300

Tyr Leu Asp Leu Ser Leu Trp Asn Thr Lys Arg Gly Met Val Asp Phe
305                 310                 315                 320

Asn Thr Phe Leu His Leu Lys Ser Leu Thr Phe Leu Asp Leu Ser Tyr
                325                 330                 335

Ile Asn Thr Arg Ser Met Val Asp Ile Ser Ile Phe Ser Pro Leu Leu
            340                 345                 350

Ser Leu Gly Tyr Leu Asp Leu Ser Gly Ile Asn Leu Lys Ile Ser Ser
        355                 360                 365

Thr Leu Ser Leu Pro Ser Pro Met Gly Thr Leu Ile Leu Ser Ser Cys
    370                 375                 380

Asn Ile Pro Glu Phe Pro Asn Phe Leu Glu Asn Gln Thr Thr Leu Tyr
385                 390                 395                 400

Tyr Leu Asp Ile Ser Ala Asn Lys Ile Gly Gly Gln Val Pro Gln Trp
                405                 410                 415

Leu Trp Ser Leu Pro Glu Leu Gln Tyr Val Asn Ile Ser Gln Asn Ser
            420                 425                 430

Phe Ser Gly Phe Glu Gly Pro Ala Asp Val Ile Gln Arg Cys Gly Glu
        435                 440                 445

Leu Leu Met Leu Asp Ile Ser Ser Asn Thr Phe Gln Asp Pro Phe Pro
    450                 455                 460

Leu Leu Pro Asn Ser Thr Thr Ile Phe Leu Gly Ser Asp Asn Arg Phe
465                 470                 475                 480

Ser Gly Glu Ile Pro Lys Thr Ile Cys Lys Leu Val Ser Leu Asp Thr
                485                 490                 495

Leu Val Leu Ser Asn Asn Asn Phe Asn Gly Ser Ile Pro Arg Cys Phe
            500                 505                 510

Glu Lys Phe Asn Thr Thr Leu Ser Val Leu His Leu Arg Asn Asn Asn
        515                 520                 525

Leu Ser Gly Glu Phe Pro Glu Glu Ser Ile Ser Asp His Leu Arg Ser
    530                 535                 540

Leu Asp Val Gly Arg Asn Arg Leu Ser Gly Glu Leu Pro Lys Ser Leu
545                 550                 555                 560

Ile Asn Cys Thr Arg Leu Glu Phe Leu Asn Val Glu Asp Asn Ile Ile
                565                 570                 575

Asn Asp Lys Phe Pro Phe Trp Leu Arg Met Leu Pro Lys Leu Gln Ile
            580                 585                 590

Phe Val Leu Arg Ser Asn Glu Phe His Gly Pro Ile Ser Ser Leu Gly
        595                 600                 605

Asp Ser Leu Ser Phe Pro Lys Leu Arg Ile Phe Asp Ile Ser Glu Asn
    610                 615                 620

Arg Phe Asn Gly Val Leu Arg Ser Asp Phe Phe Ala Gly Trp Ser Ala
625                 630                 635                 640

Met Ser Ser Ala Val Asp Ile Val Asp Ile Met Pro Ser Arg Tyr Ala
                645                 650                 655

Gly Arg Asp Ser Gly Asn Tyr Tyr Asn Ser Val Thr Met Thr Val Lys
            660                 665                 670

Gly Ser Ile Ile Glu Leu Val Gly Ser Val Phe Thr Ile Tyr Lys Thr
        675                 680                 685

Ile Asp Val Ser Gly Asn Arg Phe Glu Gly Arg Ile Pro Glu Ser Ile
    690                 695                 700
```

Gly Leu Leu Lys Glu Leu Ile Val Leu Asn Met Ser Asn Asn Gly
705 710 715

<210> SEQ ID NO 39
<211> LENGTH: 2085
<212> TYPE: DNA
<213> ORGANISM: Arabidopsis thaliana

<400> SEQUENCE: 39
atggacgaac tttttgtctc aatctcgtca acctttagca aaacctcttg cattactgat 60
cttcttcttc cacttgagct agatagaatt gaggcacaaa ggtcaacaga tgcgtctcat 120
gatcaacaga acagaacata cttacccatg aacatacacg gttcacaaga cttctctcaa 180
agcggaggag atggcgtcac gccacttaca ggagacaccg aatctgtgcc agagttcctt 240
actaacctta gattgtcgga tctttacgct atccgtggtg aagatgtccg gatgattcca 300
gaggttttta gtaaaataag tgatgggaac aaagaatgtc tggagaagtt gagaagccgt 360
ggaatttcag tggcacgtat caagagcaat acaggagatt caattcttca tcttgctgtt 420
acatggggtc atctagaact agtgaaggag attgtctgtg aatgcccgcg tcttctcttg 480
gagcaaaact caagcggtca gacaccgcta catgtggcgg ctcatagcgg tcataccact 540
attgttgagg cttttgtcgc attggtaaca ttttcttcag ctagactgtg taatgaagag 600
agtgagagaa tgaacccata tgttctcaag gacaaagatg gaaatactgc tctgtactac 660
gcgattgaag ggcgctattt cgagatggct gtatgtctgg tgaacgcaaa ccaggatgct 720
ccttttcttg gaaataagta tggagtatct tccttgtttg tggcaataaa tactggagat 780
gtatctcttg tgaaagcaat tttgaaaatc ataggcaaca aggaccttaa agggaagaag 840
tctaacttgg agtcaaagtt acaagggcag aaatctcttg cacatgttgc tttggtgacc 900
cagagtatag caggtgtcct tgatgttatt cttgatgaat atccaagtct tatggacgag 960
cgagatataa atggttggac ttgtctttca ctcgcagcac atatagggta ttatgaagga 1020
gtatgcaacc tcttagaacg atcaacaaag ggtgtttatg tctgcgacca agatggttct 1080
tttccaattc atacagctgc agagaaaggt catgaaaata ttgttgaaga gtttataaaa 1140
cgatgtccag gttcaaaaca cttacttaac aaacttggtc agaacgttct ccacattgca 1200
gcaaaaaatg ggaaattttg gatttcgaac atgttgataa ttaataaaga tacggaacat 1260
ctgggtgttg ggcaagatgt ggacgggaat acacctttgc atcttgccgt catgaactgg 1320
cactttaaat ccattacttg gcttgctagg agtagcaaga tactgaaagt gcggaacaaa 1380
aacggcttaa gagctaggga tattgccgag agagaggtga aaccccacta catctttcag 1440
gagaggtgga cactggcgct cttattatac gctattcact caaggggttt cgaatctgta 1500
cactcattaa caaaaccgtc agtgccacta gaccctaaaa ataacagaga ttacgtcaac 1560
actcttctcc tggtagctgc tcttgtagcc acaatgacgt ttgctgcagg ttttacaata 1620
ccaggtgggt ttaacagctc tgctccacac ttgggcaggg caactttggc cactaatcca 1680
actctcttca tttttctggt acttgacatc ttggccatgc aaagttccgt tgcaacaata 1740
ggtattctta tttgggcgca gttaggtgat ccagtgctca ttcgctcatc cttacatgtg 1800
gctttgccct tactgctttt tgctttactc tgcatgccct tggcattcct ttttggcgtg 1860
gtcactgcag ttgggcatgt gaaatggctt gtagtcatca tttgcattat atctgtttta 1920
ttcttttctt gggcgatctt tgtccttggc cctcacgtca tgctacaacg gtcatacgtt 1980
tctcccaagt acgctggtga ctttctcgtg acttttatgc agtataaaga cataattggg 2040

```
ctttttgtgt ctttgataaa gtttcttttt tgtggttgtt attaa                 2085


<210> SEQ ID NO 40
<211> LENGTH: 694
<212> TYPE: PRT
<213> ORGANISM: Arabidopsis thaliana

<400> SEQUENCE: 40

Met Asp Glu Leu Phe Val Ser Ile Ser Ser Thr Phe Ser Lys Thr Ser
1               5                   10                  15

Cys Ile Thr Asp Leu Leu Leu Pro Leu Glu Leu Asp Arg Ile Glu Ala
            20                  25                  30

Gln Arg Ser Thr Asp Ala Ser His Asp Gln Gln Asn Arg Thr Tyr Leu
        35                  40                  45

Pro Met Asn Ile His Gly Ser Gln Asp Phe Ser Gln Ser Gly Gly Asp
    50                  55                  60

Gly Val Thr Pro Leu Thr Gly Asp Thr Glu Ser Val Pro Glu Phe Leu
65                  70                  75                  80

Thr Asn Leu Arg Leu Ser Asp Leu Tyr Ala Ile Arg Gly Glu Asp Val
                85                  90                  95

Arg Met Ile Pro Glu Val Phe Ser Lys Ile Ser Asp Gly Asn Lys Glu
            100                 105                 110

Cys Leu Glu Lys Leu Arg Ser Arg Gly Ile Ser Val Ala Arg Ile Lys
        115                 120                 125

Ser Asn Thr Gly Asp Ser Ile Leu His Leu Ala Val Thr Trp Gly His
    130                 135                 140

Leu Glu Leu Val Lys Glu Ile Val Cys Glu Cys Pro Arg Leu Leu Leu
145                 150                 155                 160

Glu Gln Asn Ser Ser Gly Gln Thr Pro Leu His Val Ala Ala His Ser
                165                 170                 175

Gly His Thr Thr Ile Val Glu Ala Phe Val Ala Leu Val Thr Phe Ser
            180                 185                 190

Ser Ala Arg Leu Cys Asn Glu Glu Ser Glu Arg Met Asn Pro Tyr Val
        195                 200                 205

Leu Lys Asp Lys Asp Gly Asn Thr Ala Leu Tyr Tyr Ala Ile Glu Gly
    210                 215                 220

Arg Tyr Phe Glu Met Ala Val Cys Leu Val Asn Ala Asn Gln Asp Ala
225                 230                 235                 240

Pro Phe Leu Gly Asn Lys Tyr Gly Val Ser Ser Leu Phe Val Ala Ile
                245                 250                 255

Asn Thr Gly Asp Val Ser Leu Val Lys Ala Ile Leu Lys Ile Ile Gly
            260                 265                 270

Asn Lys Asp Leu Lys Gly Lys Lys Ser Asn Leu Glu Ser Lys Leu Gln
        275                 280                 285

Gly Gln Lys Ser Leu Ala His Val Ala Leu Val Thr Gln Ser Ile Ala
    290                 295                 300

Gly Val Leu Asp Val Ile Leu Asp Glu Tyr Pro Ser Leu Met Asp Glu
305                 310                 315                 320

Arg Asp Ile Asn Gly Trp Thr Cys Leu Ser Leu Ala Ala His Ile Gly
                325                 330                 335

Tyr Tyr Glu Gly Val Cys Asn Leu Leu Glu Arg Ser Thr Lys Gly Val
            340                 345                 350

Tyr Val Cys Asp Gln Asp Gly Ser Phe Pro Ile His Thr Ala Ala Glu
        355                 360                 365
```

-continued

```
Lys Gly His Glu Asn Ile Val Glu Glu Phe Ile Lys Arg Cys Pro Gly
    370                 375                 380

Ser Lys His Leu Leu Asn Lys Leu Gly Gln Asn Val Leu His Ile Ala
385                 390                 395                 400

Ala Lys Asn Gly Lys Phe Trp Ile Ser Asn Met Leu Ile Ile Asn Lys
                405                 410                 415

Asp Thr Glu His Leu Gly Val Gly Gln Asp Val Asp Gly Asn Thr Pro
            420                 425                 430

Leu His Leu Ala Val Met Asn Trp His Phe Lys Ser Ile Thr Trp Leu
        435                 440                 445

Ala Arg Ser Ser Lys Ile Leu Lys Val Arg Asn Lys Asn Gly Leu Arg
    450                 455                 460

Ala Arg Asp Ile Ala Glu Arg Glu Val Lys Pro His Tyr Ile Phe Gln
465                 470                 475                 480

Glu Arg Trp Thr Leu Ala Leu Leu Leu Tyr Ala Ile His Ser Arg Gly
                485                 490                 495

Phe Glu Ser Val His Ser Leu Thr Lys Pro Ser Val Pro Leu Asp Pro
            500                 505                 510

Lys Asn Asn Arg Asp Tyr Val Asn Thr Leu Leu Leu Val Ala Ala Leu
        515                 520                 525

Val Ala Thr Met Thr Phe Ala Ala Gly Phe Thr Ile Pro Gly Gly Phe
    530                 535                 540

Asn Ser Ser Ala Pro His Leu Gly Arg Ala Thr Leu Ala Thr Asn Pro
545                 550                 555                 560

Thr Leu Phe Ile Phe Leu Val Leu Asp Ile Leu Ala Met Gln Ser Ser
                565                 570                 575

Val Ala Thr Ile Gly Ile Leu Ile Trp Ala Gln Leu Gly Asp Pro Val
            580                 585                 590

Leu Ile Arg Ser Ser Leu His Val Ala Leu Pro Leu Leu Leu Phe Ala
        595                 600                 605

Leu Leu Cys Met Pro Leu Ala Phe Leu Phe Gly Val Val Thr Ala Val
    610                 615                 620

Gly His Val Lys Trp Leu Val Val Ile Ile Cys Ile Ile Ser Val Leu
625                 630                 635                 640

Phe Phe Ser Trp Ala Ile Phe Val Leu Gly Pro His Val Met Leu Gln
                645                 650                 655

Arg Ser Tyr Val Ser Pro Lys Tyr Ala Gly Asp Phe Leu Val Thr Phe
            660                 665                 670

Met Gln Tyr Lys Asp Ile Ile Gly Leu Phe Val Ser Leu Ile Lys Phe
        675                 680                 685

Leu Phe Cys Gly Cys Tyr
    690
```

<210> SEQ ID NO 41
<211> LENGTH: 1962
<212> TYPE: DNA
<213> ORGANISM: Arabidopsis thaliana

<400> SEQUENCE: 41

```
atggctggta aaggagaagg tcctgcgatc ggtatcgatc ttggtacgac gtactcttgc      60

gtcggagtgt ggcaacacga ccgtgttgag atcatcgcta atgatcaagg aaacagaacc     120

actccctcgt acgttgcttt cactgactcc gagaggttga tcggtgatgc tgctaagaac     180

caagtcgcca tgaaccctgt taacactgtt ttcgatgcaa agaggttgat tggtcgtaga     240
```

```
ttcagtgacg catctgtcca aagtgacaga cagttatggc ctttcactat catctccgga    300

actgcagaga aaccaatgat tgtcgtcgaa tacaagggag aagagaaaca gttcgctgct    360

gaagagatct cttccatggt tcttattaag atgcgtgaga tcgctgaggc tttccttggc    420

actacggtca agaacgctgt cgtcactgtt cctgcttact tcaatgactc tcaacgtcag    480

gctacaaagg atgctggtgt catcgctggt ttgaatgttt tgcgtatcat caacgagccc    540

actgctgcag ccattgctta tggtcttgac aagaaggcca caagtgttgg agagaagaat    600

gttttgatct ttgatcttgg tggtggtact tttgatgtct ctcttcttac aatcgaagag    660

ggtatctttg aggtgaaggc aacagctggt gatactcatc ttggtgggga agattttgac    720

aacagaatgg ttaaccattt tgttcaagag tttaagagaa agaacaagca ggatatcacc    780

ggtcaaccga gagccctcag gagattgaga acagcttgtg agagagcaaa gaggactctt    840

tcttccaccg ctcaaacgac catcgagatt gactctttat atggtggagc tgacttctat    900

tctccaatca cccgtgctag attcgaagag atgaacatgg atctctttag gaagtgtatg    960

gagcctgttg agaagtgtct ccgtgatgct aagatggaca agagcactgt tcacgagatt   1020

gtccttgttg gtggatccac ccgtatccct aaggttcagc aattgcttca ggacttcttc   1080

aacggcaaag agctttgcaa gtctatcaac cctgatgagg ctgtagctta tggtgcagct   1140

gttcaggctg cgatcctaag cggtgaagga aacgaaaagg tccaagacct tctcttgctt   1200

gatgtcacac ctctctccct tggtcttgaa actgctggtg gtgtcatgac cactttgatt   1260

caaagaaaca caaccattcc aaccaagaag gaacaggtct tctcaactta ttcggacaac   1320

cagcctggag tgttgatcca agtttttgaa ggtgagaggg ctaggaccaa ggacaacaac   1380

ctcctcggta aatttgagct ttctggaatt ccccctgctc cacgaggtgt ccctcaaatc   1440

actgtctgct tcgacattga cgccaatggt atcctcaacg tctctgctga ggacaagacc   1500

actggaaaga agaacaagat cacaatcact aatgacaagg gtcgtttgtc taaagaggat   1560

attgagaaga tggttcaaga agcggagaag tacaagtctg aggatgagga gcacaagaag   1620

aaggtcgagg ccaagaacgc tcttgagaac tacgcttaca acatgaggaa caccatccgt   1680

gatgagaaga tcggtgagaa gcttccagct gcagacaaga agaaggttga ggactctatt   1740

gaggaagcaa tccaatggct agatggtaac caattgggtg aagctgacga gtttgaagac   1800

aagatgaagg agttggagag tgtttgcaat ccgatcatcg ctaagatgta ccaaggagga   1860

gctggtggtg aagctggtgg tcctggagct tctggaatgg acgaggatga agctcctcct   1920

gcatcaggtg gtgctggtcc caagatcgag gaagtcgact aa                      1962
```

```
<210> SEQ ID NO 42
<211> LENGTH: 653
<212> TYPE: PRT
<213> ORGANISM: Arabidopsis thaliana

<400> SEQUENCE: 42

Met Ala Gly Lys Gly Glu Gly Pro Ala Ile Gly Ile Asp Leu Gly Thr
1               5                   10                  15

Thr Tyr Ser Cys Val Gly Val Trp Gln His Asp Arg Val Glu Ile Ile
            20                  25                  30

Ala Asn Asp Gln Gly Asn Arg Thr Thr Pro Ser Tyr Val Ala Phe Thr
        35                  40                  45

Asp Ser Glu Arg Leu Ile Gly Asp Ala Ala Lys Asn Gln Val Ala Met
    50                  55                  60
```

-continued

```
Asn Pro Val Asn Thr Val Phe Asp Ala Lys Arg Leu Ile Gly Arg Arg
65                  70                  75                  80

Phe Ser Asp Ala Ser Val Gln Ser Asp Arg Gln Leu Trp Pro Phe Thr
                85                  90                  95

Ile Ile Ser Gly Thr Ala Glu Lys Pro Met Ile Val Val Glu Tyr Lys
            100                 105                 110

Gly Glu Glu Lys Gln Phe Ala Ala Glu Glu Ile Ser Ser Met Val Leu
        115                 120                 125

Ile Lys Met Arg Glu Ile Ala Glu Ala Phe Leu Gly Thr Thr Val Lys
    130                 135                 140

Asn Ala Val Val Thr Val Pro Ala Tyr Phe Asn Asp Ser Gln Arg Gln
145                 150                 155                 160

Ala Thr Lys Asp Ala Gly Val Ile Ala Gly Leu Asn Val Leu Arg Ile
                165                 170                 175

Ile Asn Glu Pro Thr Ala Ala Ala Ile Ala Tyr Gly Leu Asp Lys Lys
            180                 185                 190

Ala Thr Ser Val Gly Glu Lys Asn Val Leu Ile Phe Asp Leu Gly Gly
        195                 200                 205

Gly Thr Phe Asp Val Ser Leu Leu Thr Ile Glu Glu Gly Ile Phe Glu
    210                 215                 220

Val Lys Ala Thr Ala Gly Asp Thr His Leu Gly Gly Glu Asp Phe Asp
225                 230                 235                 240

Asn Arg Met Val Asn His Phe Val Gln Glu Phe Lys Arg Lys Asn Lys
                245                 250                 255

Gln Asp Ile Thr Gly Gln Pro Arg Ala Leu Arg Arg Leu Arg Thr Ala
            260                 265                 270

Cys Glu Arg Ala Lys Arg Thr Leu Ser Ser Thr Ala Gln Thr Thr Ile
        275                 280                 285

Glu Ile Asp Ser Leu Tyr Gly Gly Ala Asp Phe Tyr Ser Pro Ile Thr
    290                 295                 300

Arg Ala Arg Phe Glu Glu Met Asn Met Asp Leu Phe Arg Lys Cys Met
305                 310                 315                 320

Glu Pro Val Glu Lys Cys Leu Arg Asp Ala Lys Met Asp Lys Ser Thr
                325                 330                 335

Val His Glu Ile Val Leu Val Gly Gly Ser Thr Arg Ile Pro Lys Val
            340                 345                 350

Gln Gln Leu Leu Gln Asp Phe Phe Asn Gly Lys Glu Leu Cys Lys Ser
        355                 360                 365

Ile Asn Pro Asp Glu Ala Val Ala Tyr Gly Ala Ala Val Gln Ala Ala
    370                 375                 380

Ile Leu Ser Gly Glu Gly Asn Glu Lys Val Gln Asp Leu Leu Leu Leu
385                 390                 395                 400

Asp Val Thr Pro Leu Ser Leu Gly Leu Glu Thr Ala Gly Gly Val Met
                405                 410                 415

Thr Thr Leu Ile Gln Arg Asn Thr Thr Ile Pro Thr Lys Lys Glu Gln
            420                 425                 430

Val Phe Ser Thr Tyr Ser Asp Asn Gln Pro Gly Val Leu Ile Gln Val
        435                 440                 445

Phe Glu Gly Glu Arg Ala Arg Thr Lys Asp Asn Asn Leu Leu Gly Lys
    450                 455                 460

Phe Glu Leu Ser Gly Ile Pro Pro Ala Pro Arg Gly Val Pro Gln Ile
465                 470                 475                 480

Thr Val Cys Phe Asp Ile Asp Ala Asn Gly Ile Leu Asn Val Ser Ala
```

-continued

```
                485                 490                 495

Glu Asp Lys Thr Thr Gly Lys Lys Asn Lys Ile Thr Ile Thr Asn Asp
            500                 505                 510

Lys Gly Arg Leu Ser Lys Glu Asp Ile Glu Lys Met Val Gln Glu Ala
        515                 520                 525

Glu Lys Tyr Lys Ser Glu Asp Glu Glu His Lys Lys Lys Val Glu Ala
    530                 535                 540

Lys Asn Ala Leu Glu Asn Tyr Ala Tyr Asn Met Arg Asn Thr Ile Arg
545                 550                 555                 560

Asp Glu Lys Ile Gly Glu Lys Leu Pro Ala Ala Asp Lys Lys Lys Val
                565                 570                 575

Glu Asp Ser Ile Glu Glu Ala Ile Gln Trp Leu Asp Gly Asn Gln Leu
            580                 585                 590

Gly Glu Ala Asp Glu Phe Glu Asp Lys Met Lys Glu Leu Glu Ser Val
        595                 600                 605

Cys Asn Pro Ile Ile Ala Lys Met Tyr Gln Gly Gly Ala Gly Gly Glu
    610                 615                 620

Ala Gly Gly Pro Gly Ala Ser Gly Met Asp Glu Asp Glu Ala Pro Pro
625                 630                 635                 640

Ala Ser Gly Gly Ala Gly Pro Lys Ile Glu Glu Val Asp
                645                 650
```

<210> SEQ ID NO 43
<211> LENGTH: 1080
<212> TYPE: DNA
<213> ORGANISM: Arabidopsis thaliana

<400> SEQUENCE: 43

```
atggattctt tgatcaaact cttcttctgc ctctttatct tcttatgtac ttcgctctta     60

tttggagaaa tcaatggagt ggagggttca aatcaaaatc atcacttgta tccatttagg    120

ccaacgaagc tctttgtgtt cggagattct tatgccgata ccggaaacat taaaaaggct    180

ttctctagct cttggaaatt cccttacggt atcactttcc ccggaaaacc cgctggccgt    240

ttctccgatg gccgtgtggc aacagatttt ctagctaaat ttgtggggat aaaatcacca    300

atcccatact tttggaaaga ttacgcggga aagaaacgat tacagtacgg aatgaatttt    360

gcgtacggag gaacaggagt gttcaacact caaactccat tgcctaacat gacaactcaa    420

atcgacatct tccagaacat tctcaccacc ggcgacatct actatcctcc cgagcttact    480

tcatccgtgg ctctcgtcag tgtcgctggc aacgactact ccaatttcat cgccctaaac    540

cgccctgcct ctgaattccc agcattcata aagcaagttg tggatcaaac agaggtgaat    600

ttgagacgga tccacgcttt gggagtgaaa aagattgcag taccatccct gcaaccgctt    660

ggttgtctcc ctcccttcac attcgtaacc tcgttccagc gttgcaacga gacacaaaac    720

gctttagtta acctccacaa caacttattg cagcaagttg tggcaaagct caataacgag    780

actaaacagt cgactttcat catccttgat ctctacaatg ctttcttgac tgtgttcaag    840

aacaaaggat ctaatccagg gagtacaagg tttgagagtc cattaaagcc gtgttgcgta    900

ggtgtgagcc gcgagtataa ctgtggaagt gtggatgaga agggagtgaa gaagtatatt    960

gtatgtgata atcctaaaac tgctttcttt tgggatggac ttcaccctac agaagaagga   1020

tggagatcgg tttactctgt tttacgcgaa agtcttaccg cgtctttgat taaagcgtga   1080
```

<210> SEQ ID NO 44
<211> LENGTH: 359

<212> TYPE: PRT
<213> ORGANISM: Arabidopsis thaliana

<400> SEQUENCE: 44

```
Met Asp Ser Leu Ile Lys Leu Phe Phe Cys Leu Phe Ile Phe Leu Cys
1               5                   10                  15

Thr Ser Leu Leu Phe Gly Glu Ile Asn Gly Val Glu Gly Ser Asn Gln
            20                  25                  30

Asn His His Leu Tyr Pro Phe Arg Pro Thr Lys Leu Phe Val Phe Gly
        35                  40                  45

Asp Ser Tyr Ala Asp Thr Gly Asn Ile Lys Lys Ala Phe Ser Ser Ser
    50                  55                  60

Trp Lys Phe Pro Tyr Gly Ile Thr Phe Pro Gly Lys Pro Ala Gly Arg
65                  70                  75                  80

Phe Ser Asp Gly Arg Val Ala Thr Asp Phe Leu Ala Lys Phe Val Gly
                85                  90                  95

Ile Lys Ser Pro Ile Pro Tyr Phe Trp Lys Asp Tyr Ala Gly Lys Lys
            100                 105                 110

Arg Leu Gln Tyr Gly Met Asn Phe Ala Tyr Gly Gly Thr Gly Val Phe
        115                 120                 125

Asn Thr Gln Thr Pro Leu Pro Asn Met Thr Thr Gln Ile Asp Ile Phe
    130                 135                 140

Gln Asn Ile Leu Thr Thr Gly Asp Ile Tyr Tyr Pro Pro Glu Leu Thr
145                 150                 155                 160

Ser Ser Val Ala Leu Val Ser Val Ala Gly Asn Asp Tyr Ser Asn Phe
                165                 170                 175

Ile Ala Leu Asn Arg Pro Ala Ser Glu Phe Pro Ala Phe Ile Lys Gln
            180                 185                 190

Val Val Asp Gln Thr Glu Val Asn Leu Arg Arg Ile His Ala Leu Gly
        195                 200                 205

Val Lys Lys Ile Ala Val Pro Ser Leu Gln Pro Leu Gly Cys Leu Pro
    210                 215                 220

Pro Phe Thr Phe Val Thr Ser Phe Gln Arg Cys Asn Glu Thr Gln Asn
225                 230                 235                 240

Ala Leu Val Asn Leu His Asn Asn Leu Leu Gln Gln Val Val Ala Lys
                245                 250                 255

Leu Asn Asn Glu Thr Lys Gln Ser Thr Phe Ile Ile Leu Asp Leu Tyr
            260                 265                 270

Asn Ala Phe Leu Thr Val Phe Lys Asn Lys Gly Ser Asn Pro Gly Ser
        275                 280                 285

Thr Arg Phe Glu Ser Pro Leu Lys Pro Cys Cys Val Gly Val Ser Arg
    290                 295                 300

Glu Tyr Asn Cys Gly Ser Val Asp Glu Lys Gly Val Lys Lys Tyr Ile
305                 310                 315                 320

Val Cys Asp Asn Pro Lys Thr Ala Phe Phe Trp Asp Gly Leu His Pro
                325                 330                 335

Thr Glu Glu Gly Trp Arg Ser Val Tyr Ser Val Leu Arg Glu Ser Leu
            340                 345                 350

Thr Ala Ser Leu Ile Lys Ala
        355
```

<210> SEQ ID NO 45
<211> LENGTH: 1077
<212> TYPE: DNA
<213> ORGANISM: Arabidopsis thaliana -continued

<400> SEQUENCE: 45

```
atggctgtaa caagctcttc ttctacttgt gatggtttct tcatcatcag ccttattgtt      60
atcgtttctt cattgtttgg gacatcatct gcgcagttaa acgcaacgtt ttactcaggc     120
acatgcccta acgcctctgc catcgttcgc agcactattc agcaagctct tcaatccgat     180
gcaagaatcg gaggcagcct aatccgcctt cattttcacg actgttttgt taatggttgc     240
gatgggtcgc tcttgcttga cgacacttca agcatccaga gcgagaagaa cgctcctgcc     300
aatgcaaact caactagagg attcaatgtt gtcgatagta tcaagacagc cctcgagaat     360
gcttgtccgg gcattgtttc ttgctctgac attttagctc ttgcctcaga ggcctctgtg     420
tctttggcag gaggaccttc atggactgtg ttattaggaa gaagagatgg tctcaccgca     480
aacttgtctg gagccaattc gtctcttccc tctcccttcg aaggccttaa caacatcaca     540
tcaaaatttg tagctgtcgg gctaaagaca accgatgtag tatccttgtc tggagcgcat     600
acgtttgggc gtggtcaatg cgtaacgttc aacaatagac tattcaactt caacgggaca     660
ggaaaccccg acccgactct gaactcaaca cttctcagca gtcttcaaca gctatgtcct     720
caaaacggca gcaatacagg gatcaccaat ctcgatctga gcacacctga tgcgttcgat     780
aacaattact tcacgaacct tcagagtaac aatgggcttc tccagtcaga ccaggaactg     840
ttctcaaaca ccggttcagc caccgtcccg attgttaatt cctttgcaag taaccagacc     900
ctgtttttg aggcgtttgt tcagtctatg atcaagatgg ggaacattag tcccttgact      960
gggagtagtg gagagattag acaagactgt aaggtggtta atggacagtc atcagccact    1020
gaagcagggg acattcagtt acaatctgac ggaccagtga gtgtagcaga tatgtga       1077
```

<210> SEQ ID NO 46
<211> LENGTH: 358
<212> TYPE: PRT
<213> ORGANISM: Arabidopsis thaliana

<400> SEQUENCE: 46

```
Met Ala Val Thr Ser Ser Ser Ser Thr Cys Asp Gly Phe Phe Ile Ile
1               5                   10                  15

Ser Leu Ile Val Ile Val Ser Ser Leu Phe Gly Thr Ser Ser Ala Gln
            20                  25                  30

Leu Asn Ala Thr Phe Tyr Ser Gly Thr Cys Pro Asn Ala Ser Ala Ile
        35                  40                  45

Val Arg Ser Thr Ile Gln Gln Ala Leu Gln Ser Asp Ala Arg Ile Gly
    50                  55                  60

Gly Ser Leu Ile Arg Leu His Phe His Asp Cys Phe Val Asn Gly Cys
65                  70                  75                  80

Asp Gly Ser Leu Leu Leu Asp Asp Thr Ser Ser Ile Gln Ser Glu Lys
                85                  90                  95

Asn Ala Pro Ala Asn Ala Asn Ser Thr Arg Gly Phe Asn Val Val Asp
            100                 105                 110

Ser Ile Lys Thr Ala Leu Glu Asn Ala Cys Pro Gly Ile Val Ser Cys
        115                 120                 125

Ser Asp Ile Leu Ala Leu Ala Ser Glu Ala Ser Val Ser Leu Ala Gly
    130                 135                 140

Gly Pro Ser Trp Thr Val Leu Leu Gly Arg Arg Asp Gly Leu Thr Ala
145                 150                 155                 160

Asn Leu Ser Gly Ala Asn Ser Ser Leu Pro Ser Pro Phe Glu Gly Leu
                165                 170                 175
```

```
Asn Asn Ile Thr Ser Lys Phe Val Ala Val Gly Leu Lys Thr Thr Asp
            180                 185                 190

Val Val Ser Leu Ser Gly Ala His Thr Phe Gly Arg Gly Gln Cys Val
        195                 200                 205

Thr Phe Asn Asn Arg Leu Phe Asn Phe Asn Gly Thr Gly Asn Pro Asp
    210                 215                 220

Pro Thr Leu Asn Ser Thr Leu Leu Ser Ser Leu Gln Gln Leu Cys Pro
225                 230                 235                 240

Gln Asn Gly Ser Asn Thr Gly Ile Thr Asn Leu Asp Leu Ser Thr Pro
                245                 250                 255

Asp Ala Phe Asp Asn Asn Tyr Phe Thr Asn Leu Gln Ser Asn Asn Gly
            260                 265                 270

Leu Leu Gln Ser Asp Gln Glu Leu Phe Ser Asn Thr Gly Ser Ala Thr
        275                 280                 285

Val Pro Ile Val Asn Ser Phe Ala Ser Asn Gln Thr Leu Phe Phe Glu
    290                 295                 300

Ala Phe Val Gln Ser Met Ile Lys Met Gly Asn Ile Ser Pro Leu Thr
305                 310                 315                 320

Gly Ser Ser Gly Glu Ile Arg Gln Asp Cys Lys Val Val Asn Gly Gln
                325                 330                 335

Ser Ser Ala Thr Glu Ala Gly Asp Ile Gln Leu Gln Ser Asp Gly Pro
            340                 345                 350

Val Ser Val Ala Asp Met
        355
```

<210> SEQ ID NO 47
<211> LENGTH: 2490
<212> TYPE: DNA
<213> ORGANISM: Arabidopsis thaliana

<400> SEQUENCE: 47

```
atggcttcaa gacaaggatt gtcctcaacg tccgagactc caaacaaact gttgttggtg     60

ctgccgcttc agaagaggga agtggtggcc attattggac cagggacttc aatgcaagct    120

ccatttttaa tcaaccttgg aaaccaatct aaagttccaa tcatttcatt ctctgcaaca    180

agccctcttc ttgattccct ccgtagtcca tatttcatca gagccactca cgacgattcg    240

tctcaagtcc aagccattag cgccatcata gagtcattta gatggagaga agttgtgcct    300

atatatgtag acaatgagtt cggagaaggt attcttccta acttagttga tgcttttcaa    360

gagattaatg ttcgtatccg ataccgaagt gccatctcat tacattactc tgatgatcaa    420

atcaagaaag agctttacaa actaatgacc atgcctacta gggtttttat cgtgcacatg    480

ctgcctgatc tcgggtcaag actcttttcg atagcaaaag agattgatat gctgagcaaa    540

ggatatgtat ggatagtcac aaatggtata gctgatctca tgagtataat gggggaatca    600

agcttggtga atatgcatgg tgtcttgggc gtcaagacat attttgcaaa atccaaagag    660

ctactacatc ttgaagctcg ttggcaaaaa agattcggag gagaagagct gaacaacttt    720

gcatgttggg cttatgatgc tgccacagca cttgcaatgt cagttgagga aattaggcac    780

gtaaacatga gtttcaacac gaccaaagaa gacacttcaa gagatgatat tgggactgat    840

cttgatgaac tcggcgttgc tctatctggt cccaagcttc ttgatgcctt gtcaacagtc    900

agtttcaaag gtgttgccgg gagatttcag ctaaaaaacg gaaagctaga ggcgacgact    960

ttcaagatta tcaatataga ggaaagcggt gaaagaacgg ttggattttg gaaatcaaaa   1020
```

-continued

```
gtaggattag taaagagctt aagagtagat aaagtgtctc acagctcccg tcgccttaga   1080

ccgataatat ggcctggtga cactattttt gtgcctaaag gttgggaatt cccaacaaac   1140

gcaaagaagc tgcgaatagc agttccaaag aaggatggtt tcaacaattt tgttgaggta   1200

accaaggatg aaaatactaa tgttccaacg gtcaccgggt tttgcataga tgttttcaac   1260

acggtaatga gccaaatgcc atatgctgtc tcctatgagt acatcccctt tgatacgcct   1320

gatggaaaac ctcgtggaag ttacgatgaa atggtttata atgtgtttct tggggagttt   1380

gatggagctg taggtgatac aacaattttg gctaatcggt cgcattatgt tgatttcgcg   1440

ttgccatact cggagaccgg aattgtattc cttgtaccag tcaaggatgg gaaagaaaaa   1500

ggagaatggg tcttcttaaa gcctttaaca aaggagctat ggttggtcac tgctgcttct   1560

tttctctaca ttggaatcat ggtttggatt tttgagtacc aagcagatga ggagttcagg   1620

gaacagatga taattgataa aatatctagt gtgttctact tctcgttttc gactctcttt   1680

ttcgcacaca ggaggccatc agagagcttt tttacaaggg ttcttgttgt ggtttggtgc   1740

tttgtgttgc taattctgac tcagagctac acagcaacac tgacatcgat gctgacagtt   1800

caagagcttc gaccaacagt gagacacatg gatgatttga ggaagagcgg agtgaacatt   1860

ggatatcaaa ctggttcgtt tacattcgaa aggctgaaac aaatgcgttt cgatgaatcg   1920

aggttaaaga catataattc tcctgaagag atgcgtgaac tttttcttca caagagcagc   1980

aatggcggga ttgatgctgc gttcgatgag gtcgcttata tcaagctttt catggctaag   2040

tattgctcag agtattccat catcgagcct acctttaagg ctgatggctt tggctttgca   2100

tttccactag gatctccatt ggtgtcagat atttcaagac agatcttgaa cataacagag   2160

ggagatgcca tgaaagctat agagaacaag tggttccttg gagaaaaaca ttgtctggac   2220

tcgactacat cagattctcc aatccagctc gaccaccaca gctttgaagc tctatttctg   2280

atcgtctttg ttgtttctgt gattctactc ttactcatgt tggcttctag aggataccaa   2340

gagagacaac acaatgcttc acccaatcta ccaaatgatc aagccaatgc agctcaagaa   2400

gaagtcaatg aagaaggtaa tgttggagat catattgtgg aagtcgacac agctttggct   2460

aaagtcagca tagtcaaacc taaactctag                                     2490
```

<210> SEQ ID NO 48
<211> LENGTH: 829
<212> TYPE: PRT
<213> ORGANISM: Arabidopsis thaliana

<400> SEQUENCE: 48

```
Met Ala Ser Arg Gln Gly Leu Ser Ser Thr Ser Glu Thr Pro Asn Lys
1               5                   10                  15

Leu Leu Leu Val Leu Pro Leu Gln Lys Arg Glu Val Val Ala Ile Ile
            20                  25                  30

Gly Pro Gly Thr Ser Met Gln Ala Pro Phe Leu Ile Asn Leu Gly Asn
        35                  40                  45

Gln Ser Lys Val Pro Ile Ile Ser Phe Ser Ala Thr Ser Pro Leu Leu
    50                  55                  60

Asp Ser Leu Arg Ser Pro Tyr Phe Ile Arg Ala Thr His Asp Asp Ser
65                  70                  75                  80

Ser Gln Val Gln Ala Ile Ser Ala Ile Ile Glu Ser Phe Arg Trp Arg
                85                  90                  95

Glu Val Val Pro Ile Tyr Val Asp Asn Glu Phe Gly Glu Gly Ile Leu
            100                 105                 110
```

-continued

```
Pro Asn Leu Val Asp Ala Phe Gln Glu Ile Asn Val Arg Ile Arg Tyr
        115                 120                 125

Arg Ser Ala Ile Ser Leu His Tyr Ser Asp Asp Gln Ile Lys Lys Glu
    130                 135                 140

Leu Tyr Lys Leu Met Thr Met Pro Thr Arg Val Phe Ile Val His Met
145                 150                 155                 160

Leu Pro Asp Leu Gly Ser Arg Leu Phe Ser Ile Ala Lys Glu Ile Asp
                165                 170                 175

Met Leu Ser Lys Gly Tyr Val Trp Ile Val Thr Asn Gly Ile Ala Asp
            180                 185                 190

Leu Met Ser Ile Met Gly Glu Ser Ser Leu Val Asn Met His Gly Val
        195                 200                 205

Leu Gly Val Lys Thr Tyr Phe Ala Lys Ser Lys Glu Leu Leu His Leu
    210                 215                 220

Glu Ala Arg Trp Gln Lys Arg Phe Gly Gly Glu Glu Leu Asn Asn Phe
225                 230                 235                 240

Ala Cys Trp Ala Tyr Asp Ala Ala Thr Ala Leu Ala Met Ser Val Glu
                245                 250                 255

Glu Ile Arg His Val Asn Met Ser Phe Asn Thr Thr Lys Glu Asp Thr
            260                 265                 270

Ser Arg Asp Asp Ile Gly Thr Asp Leu Asp Glu Leu Gly Val Ala Leu
        275                 280                 285

Ser Gly Pro Lys Leu Leu Asp Ala Leu Ser Thr Val Ser Phe Lys Gly
    290                 295                 300

Val Ala Gly Arg Phe Gln Leu Lys Asn Gly Lys Leu Glu Ala Thr Thr
305                 310                 315                 320

Phe Lys Ile Ile Asn Ile Glu Glu Ser Gly Glu Arg Thr Val Gly Phe
                325                 330                 335

Trp Lys Ser Lys Val Gly Leu Val Lys Ser Leu Arg Val Asp Lys Val
            340                 345                 350

Ser His Ser Ser Arg Arg Leu Arg Pro Ile Ile Trp Pro Gly Asp Thr
        355                 360                 365

Ile Phe Val Pro Lys Gly Trp Glu Phe Pro Thr Asn Ala Lys Lys Leu
    370                 375                 380

Arg Ile Ala Val Pro Lys Lys Asp Gly Phe Asn Asn Phe Val Glu Val
385                 390                 395                 400

Thr Lys Asp Glu Asn Thr Asn Val Pro Thr Val Thr Gly Phe Cys Ile
                405                 410                 415

Asp Val Phe Asn Thr Val Met Ser Gln Met Pro Tyr Ala Val Ser Tyr
            420                 425                 430

Glu Tyr Ile Pro Phe Asp Thr Pro Asp Gly Lys Pro Arg Gly Ser Tyr
        435                 440                 445

Asp Glu Met Val Tyr Asn Val Phe Leu Gly Glu Phe Asp Gly Ala Val
    450                 455                 460

Gly Asp Thr Thr Ile Leu Ala Asn Arg Ser His Tyr Val Asp Phe Ala
465                 470                 475                 480

Leu Pro Tyr Ser Glu Thr Gly Ile Val Phe Leu Val Pro Val Lys Asp
                485                 490                 495

Gly Lys Glu Lys Gly Glu Trp Val Phe Leu Lys Pro Leu Thr Lys Glu
            500                 505                 510

Leu Trp Leu Val Thr Ala Ala Ser Phe Leu Tyr Ile Gly Ile Met Val
        515                 520                 525

Trp Ile Phe Glu Tyr Gln Ala Asp Glu Glu Phe Arg Glu Gln Met Ile
```

-continued

```
    530                 535                 540

Ile Asp Lys Ile Ser Ser Val Phe Tyr Phe Ser Phe Ser Thr Leu Phe
545                 550                 555                 560

Phe Ala His Arg Arg Pro Ser Glu Ser Phe Phe Thr Arg Val Leu Val
                565                 570                 575

Val Val Trp Cys Phe Val Leu Leu Ile Leu Thr Gln Ser Tyr Thr Ala
            580                 585                 590

Thr Leu Thr Ser Met Leu Thr Val Gln Glu Leu Arg Pro Thr Val Arg
        595                 600                 605

His Met Asp Asp Leu Arg Lys Ser Gly Val Asn Ile Gly Tyr Gln Thr
    610                 615                 620

Gly Ser Phe Thr Phe Glu Arg Leu Lys Gln Met Arg Phe Asp Glu Ser
625                 630                 635                 640

Arg Leu Lys Thr Tyr Asn Ser Pro Glu Glu Met Arg Glu Leu Phe Leu
                645                 650                 655

His Lys Ser Ser Asn Gly Gly Ile Asp Ala Ala Phe Asp Glu Val Ala
            660                 665                 670

Tyr Ile Lys Leu Phe Met Ala Lys Tyr Cys Ser Glu Tyr Ser Ile Ile
        675                 680                 685

Glu Pro Thr Phe Lys Ala Asp Gly Phe Gly Phe Ala Phe Pro Leu Gly
    690                 695                 700

Ser Pro Leu Val Ser Asp Ile Ser Arg Gln Ile Leu Asn Ile Thr Glu
705                 710                 715                 720

Gly Asp Ala Met Lys Ala Ile Glu Asn Lys Trp Phe Leu Gly Glu Lys
                725                 730                 735

His Cys Leu Asp Ser Thr Thr Ser Asp Ser Pro Ile Gln Leu Asp His
            740                 745                 750

His Ser Phe Glu Ala Leu Phe Leu Ile Val Phe Val Val Ser Val Ile
        755                 760                 765

Leu Leu Leu Leu Met Leu Ala Ser Arg Gly Tyr Gln Glu Arg Gln His
    770                 775                 780

Asn Ala Ser Pro Asn Leu Pro Asn Asp Gln Ala Asn Ala Ala Gln Glu
785                 790                 795                 800

Glu Val Asn Glu Glu Gly Asn Val Gly Asp His Ile Val Glu Val Asp
                805                 810                 815

Thr Ala Leu Ala Lys Val Ser Ile Val Lys Pro Lys Leu
            820                 825


<210> SEQ ID NO 49
<211> LENGTH: 1518
<212> TYPE: DNA
<213> ORGANISM: Arabidopsis thaliana

<400> SEQUENCE: 49

atgtttttct ctaaggatct tccttcacct acttcggttt tcacagctta cgcatcaatg     60

gcgggttaca tgatgatgat aagatcaatg gctcacgagc taatcccagc tcccctccaa    120

gatttcatct acaggactct ccggtctctc ttcttccgtt cttcttcctc cactttgacg    180

ctaaccatcg atgacgacaa catgggtatg aacaacgaga tctaccgagc tgctcagact    240

tatctctcca ccaagatcag tcctgatgca gtcaggctca gaataagtaa aggccataag    300

gataaacatg tcaacttgta tctcagcgac ggagaaatcg tcaacgatgt gtacgaagat    360

gtgcagctag tatggaggtt tgttactgac ggtggagaca agaaaggagg cggcggagga    420

gtaggaggaa gaggaggagg aggaggaaga agaggtggta tggacgatga cggtaaaagc    480
```

-continued

```
gagtacttcg agctgagttt cgacaagaaa cataaagatt tgatattgaa ctcttatgtg    540
ccttacatcg agagtaaagc taaagagata agagacgaga gaagaatctt gatgctgcat    600
tctctcaaca gtcttagatg ggaatcagtt attcttgaac acccttcgac ctttgagaca    660
atggctatgg aagatgatct caaacgtgac gtcatcgagg atcttgatcg gttcataaga    720
aggaaagagt tttacaagag agtagggaaa gcttggaaga ggggttactt gttgtacggt    780
ccaccgggta cggggaagtc tagtcttgtt gcagccatgg ctaattacct caagtttgat    840
gtttatgatc ttcagcttgc gagtgtgatg cgtgactctg atctaaggag gctcttacta    900
gctacacgta accggtcgat tcttgtcata gaagatatcg attgtgcagt ggatttaccc    960
aacagaattg agcagcctgt tgaaggcaag aaccgtggcg agtctcaggg accattgacg   1020
ttatcggggc tgctgaattt catagacgga ctatggtcaa gctgtggaga cgagcggatt   1080
ataatattca caacaaacca taaagatagg cttgacccgg cattgcttag accaggacgt   1140
atggatatgc acatttacat gggacattgc tcttttcaag gattcaagac tttagcttct   1200
aactacttgg gtttgagtga tgctgcgatg ccacaccgtc tatttccgga gattgagcgt   1260
ttgattgacg gggaagtaat gacgccggca caagtagcag aggagctgat gaagagtgag   1320
gatgctgacg tggcgctaga gggtttggtg aatgttttag agaaaatgag gctaaaatct   1380
aaggaatcga atccggtgat gatgaagcag aaagagagta gactggagat ggaggagatg   1440
agactaaaga gtgatactga gggttctccg aggaagaaca gcaaaagatt taagaagctt   1500
gtattgtttt ggacataa                                                 1518
```

<210> SEQ ID NO 50
<211> LENGTH: 1026
<212> TYPE: DNA
<213> ORGANISM: Arabidopsis thaliana

<400> SEQUENCE: 50

```
atgtttttct ctaaggatct tccttcacct acttcggttt tcacagctta cgcatcaatg     60
gcgggttaca tgatgatgat aagatcaatg gctcacgagc taatcccagc tcccctccaa    120
gatttcatct acaggactct ccggtctctc ttcttccgtt cttcttcctc cactttgacg    180
ctaaccatcg atgacgacaa catgggtatg aacaacgaga tctaccgagc tgctcagact    240
tatctctcca ccaagatcag tcctgatgca gtcaggctca gaataagtaa aggccataag    300
gataaacatg tcaacttgta tctcagcgac ggagaaatcg tcaacgatgt gtacgaagat    360
gtgcagctag tatggaggtt tgttactgac ggtggagaca agaaaggagg cggcggagga    420
gtaggaggaa gaggaggagg aggaggaaga agaggtggta tggacgatga cggtaaaagc    480
gagtacttcg agctgagttt cgacaagaaa cataaagatt tgatattgaa ctcttatgtg    540
ccttacatcg agagtaaagc taaagagata agagacgaga gaagaatctt gatgctgcat    600
tctctcaaca gtcttagatg ggaatcagtt attcttgaac acccttcgac ctttgagaca    660
atggctatgg aagatgatct caaacgtgac gtcatcgagg atcttgatcg gttcataaga    720
aggaaagagt tttacaagag agtagggaaa gcttggaaga ggggttactt gttgtacggt    780
ccaccgggta cggggaagtc tagtcttgtt gcagccatgg ctaattacct caagtttgat    840
gtttatgatc ttcagcttgc gagtgtgatg cgtgactctg atctaaggag gctcttacta    900
gctacacgta accggtcgat tcttgtcata gaagatatcg attgtgcagt ggatttaccc    960
aacagaattg agcagcctgt tgaaggcaag aaccgtggcg agtctcaggt tagatttcta   1020
```

```
ctatga                                                          1026


<210> SEQ ID NO 51
<211> LENGTH: 505
<212> TYPE: PRT
<213> ORGANISM: Arabidopsis thaliana

<400> SEQUENCE: 51

Met Phe Phe Ser Lys Asp Leu Pro Ser Pro Thr Ser Val Phe Thr Ala
1               5                   10                  15

Tyr Ala Ser Met Ala Gly Tyr Met Met Met Ile Arg Ser Met Ala His
            20                  25                  30

Glu Leu Ile Pro Ala Pro Leu Gln Asp Phe Ile Tyr Arg Thr Leu Arg
        35                  40                  45

Ser Leu Phe Phe Arg Ser Ser Ser Ser Thr Leu Thr Leu Thr Ile Asp
    50                  55                  60

Asp Asp Asn Met Gly Met Asn Asn Glu Ile Tyr Arg Ala Ala Gln Thr
65                  70                  75                  80

Tyr Leu Ser Thr Lys Ile Ser Pro Asp Ala Val Arg Leu Arg Ile Ser
                85                  90                  95

Lys Gly His Lys Asp Lys His Val Asn Leu Tyr Leu Ser Asp Gly Glu
            100                 105                 110

Ile Val Asn Asp Val Tyr Glu Asp Val Gln Leu Val Trp Arg Phe Val
        115                 120                 125

Thr Asp Gly Gly Asp Lys Lys Gly Gly Gly Gly Gly Val Gly Gly Arg
    130                 135                 140

Gly Gly Gly Gly Gly Arg Arg Gly Gly Met Asp Asp Asp Gly Lys Ser
145                 150                 155                 160

Glu Tyr Phe Glu Leu Ser Phe Asp Lys Lys His Lys Asp Leu Ile Leu
                165                 170                 175

Asn Ser Tyr Val Pro Tyr Ile Glu Ser Lys Ala Lys Glu Ile Arg Asp
            180                 185                 190

Glu Arg Arg Ile Leu Met Leu His Ser Leu Asn Ser Leu Arg Trp Glu
        195                 200                 205

Ser Val Ile Leu Glu His Pro Ser Thr Phe Glu Thr Met Ala Met Glu
    210                 215                 220

Asp Asp Leu Lys Arg Asp Val Ile Glu Asp Leu Asp Arg Phe Ile Arg
225                 230                 235                 240

Arg Lys Glu Phe Tyr Lys Arg Val Gly Lys Ala Trp Lys Arg Gly Tyr
                245                 250                 255

Leu Leu Tyr Gly Pro Pro Gly Thr Gly Lys Ser Ser Leu Val Ala Ala
            260                 265                 270

Met Ala Asn Tyr Leu Lys Phe Asp Val Tyr Asp Leu Gln Leu Ala Ser
        275                 280                 285

Val Met Arg Asp Ser Asp Leu Arg Arg Leu Leu Leu Ala Thr Arg Asn
    290                 295                 300

Arg Ser Ile Leu Val Ile Glu Asp Ile Asp Cys Ala Val Asp Leu Pro
305                 310                 315                 320

Asn Arg Ile Glu Gln Pro Val Glu Gly Lys Asn Arg Gly Glu Ser Gln
                325                 330                 335

Gly Pro Leu Thr Leu Ser Gly Leu Leu Asn Phe Ile Asp Gly Leu Trp
            340                 345                 350

Ser Ser Cys Gly Asp Glu Arg Ile Ile Ile Phe Thr Thr Asn His Lys
        355                 360                 365
```

-continued

```
Asp Arg Leu Asp Pro Ala Leu Leu Arg Pro Gly Arg Met Asp Met His
    370                 375                 380

Ile Tyr Met Gly His Cys Ser Phe Gln Gly Phe Lys Thr Leu Ala Ser
385                 390                 395                 400

Asn Tyr Leu Gly Leu Ser Asp Ala Ala Met Pro His Arg Leu Phe Pro
                405                 410                 415

Glu Ile Glu Arg Leu Ile Asp Gly Glu Val Met Thr Pro Ala Gln Val
            420                 425                 430

Ala Glu Glu Leu Met Lys Ser Glu Asp Ala Asp Val Ala Leu Glu Gly
        435                 440                 445

Leu Val Asn Val Leu Glu Lys Met Arg Leu Lys Ser Lys Glu Ser Asn
    450                 455                 460

Pro Val Met Met Lys Gln Lys Glu Ser Arg Leu Glu Met Glu Glu Met
465                 470                 475                 480

Arg Leu Lys Ser Asp Thr Glu Gly Ser Pro Arg Lys Asn Ser Lys Arg
                485                 490                 495

Phe Lys Lys Leu Val Leu Phe Trp Thr
            500                 505


<210> SEQ ID NO 52
<211> LENGTH: 341
<212> TYPE: PRT
<213> ORGANISM: Arabidopsis thaliana

<400> SEQUENCE: 52

Met Phe Phe Ser Lys Asp Leu Pro Ser Pro Thr Ser Val Phe Thr Ala
1               5                   10                  15

Tyr Ala Ser Met Ala Gly Tyr Met Met Met Ile Arg Ser Met Ala His
            20                  25                  30

Glu Leu Ile Pro Ala Pro Leu Gln Asp Phe Ile Tyr Arg Thr Leu Arg
        35                  40                  45

Ser Leu Phe Phe Arg Ser Ser Ser Ser Thr Leu Thr Leu Thr Ile Asp
    50                  55                  60

Asp Asp Asn Met Gly Met Asn Asn Glu Ile Tyr Arg Ala Ala Gln Thr
65                  70                  75                  80

Tyr Leu Ser Thr Lys Ile Ser Pro Asp Ala Val Arg Leu Arg Ile Ser
                85                  90                  95

Lys Gly His Lys Asp Lys His Val Asn Leu Tyr Leu Ser Asp Gly Glu
            100                 105                 110

Ile Val Asn Asp Val Tyr Glu Asp Val Gln Leu Val Trp Arg Phe Val
        115                 120                 125

Thr Asp Gly Gly Asp Lys Lys Gly Gly Gly Gly Gly Val Gly Gly Arg
    130                 135                 140

Gly Gly Gly Gly Gly Arg Arg Gly Gly Met Asp Asp Asp Gly Lys Ser
145                 150                 155                 160

Glu Tyr Phe Glu Leu Ser Phe Asp Lys Lys His Lys Asp Leu Ile Leu
                165                 170                 175

Asn Ser Tyr Val Pro Tyr Ile Glu Ser Lys Ala Lys Glu Ile Arg Asp
            180                 185                 190

Glu Arg Arg Ile Leu Met Leu His Ser Leu Asn Ser Leu Arg Trp Glu
        195                 200                 205

Ser Val Ile Leu Glu His Pro Ser Thr Phe Glu Thr Met Ala Met Glu
    210                 215                 220

Asp Asp Leu Lys Arg Asp Val Ile Glu Asp Leu Asp Arg Phe Ile Arg
225                 230                 235                 240
```

```
Arg Lys Glu Phe Tyr Lys Arg Val Gly Lys Ala Trp Lys Arg Gly Tyr
                245                 250                 255

Leu Leu Tyr Gly Pro Pro Gly Thr Gly Lys Ser Ser Leu Val Ala Ala
            260                 265                 270

Met Ala Asn Tyr Leu Lys Phe Asp Val Tyr Asp Leu Gln Leu Ala Ser
        275                 280                 285

Val Met Arg Asp Ser Asp Leu Arg Arg Leu Leu Leu Ala Thr Arg Asn
    290                 295                 300

Arg Ser Ile Leu Val Ile Glu Asp Ile Asp Cys Ala Val Asp Leu Pro
305                 310                 315                 320

Asn Arg Ile Glu Gln Pro Val Glu Gly Lys Asn Arg Gly Glu Ser Gln
                325                 330                 335

Val Arg Phe Leu Leu
            340
```

<210> SEQ ID NO 53
<211> LENGTH: 669
<212> TYPE: DNA
<213> ORGANISM: Arabidopsis thaliana

<400> SEQUENCE: 53

```
atgaaaagtt tctcatttct tgcagtttta tctatcttgg caataacact ttcattaagc     60

aaggcttcgg acccaagctc tcttcaggac ttttgcgttg gtgtcaacac cccagcagat    120

ggtgtttttg tgaacggaaa gttctgcaag gacccgaagc tcgtcacagt agaagacttc    180

ttttttacag ggctccacga ggcaagacca cctaatccaa aaactgggtc taacgtaaca    240

gccgtcaatg ttaacaacct accagggtta aacactcttg gaatctcact tgtccgtatc    300

gactatggag tttacggaca gaacccacct cacacccacc cacgtgcctc cgaggtcttg    360

tatgtcgcgg ttggaacact tttcgttggg tttgtcacgt caaaccccga aaatcgcctt    420

ttcagtaaaa cactttacga gggtgatgtc tttgtgtttc cacagggact cattcatttc    480

caagtgaacg ttggaaaata tccggcggtt gcattcgctg gtctcagcag ccaaaaccct    540

ggtgtcatca ctattgctga caccgtgttt gggtctaacc cacagataga cccaagtttt    600

cttgcaagtg cattccaggt tgaccctaag attgtcatgg atctacagac caagttcata    660

aaaccataa                                                            669
```

<210> SEQ ID NO 54
<211> LENGTH: 222
<212> TYPE: PRT
<213> ORGANISM: Arabidopsis thaliana

<400> SEQUENCE: 54

```
Met Lys Ser Phe Ser Phe Leu Ala Val Leu Ser Ile Leu Ala Ile Thr
1               5                   10                  15

Leu Ser Leu Ser Lys Ala Ser Asp Pro Ser Ser Leu Gln Asp Phe Cys
            20                  25                  30

Val Gly Val Asn Thr Pro Ala Asp Gly Val Phe Val Asn Gly Lys Phe
        35                  40                  45

Cys Lys Asp Pro Lys Leu Val Thr Val Glu Asp Phe Phe Phe Thr Gly
    50                  55                  60

Leu His Glu Ala Arg Pro Pro Asn Pro Lys Thr Gly Ser Asn Val Thr
65                  70                  75                  80

Ala Val Asn Val Asn Asn Leu Pro Gly Leu Asn Thr Leu Gly Ile Ser
                85                  90                  95
```

Leu Val Arg Ile Asp Tyr Gly Val Tyr Gly Gln Asn Pro Pro His Thr
100 105 110

His Pro Arg Ala Ser Glu Val Leu Tyr Val Ala Val Gly Thr Leu Phe
115 120 125

Val Gly Phe Val Thr Ser Asn Pro Glu Asn Arg Leu Phe Ser Lys Thr
130 135 140

Leu Tyr Glu Gly Asp Val Phe Val Phe Pro Gln Gly Leu Ile His Phe
145 150 155 160

Gln Val Asn Val Gly Lys Tyr Pro Ala Val Ala Phe Ala Gly Leu Ser
165 170 175

Ser Gln Asn Pro Gly Val Ile Thr Ile Ala Asp Thr Val Phe Gly Ser
180 185 190

Asn Pro Gln Ile Asp Pro Ser Phe Leu Ala Ser Ala Phe Gln Val Asp
195 200 205

Pro Lys Ile Val Met Asp Leu Gln Thr Lys Phe Ile Lys Pro
210 215 220

<210> SEQ ID NO 55
<211> LENGTH: 525
<212> TYPE: DNA
<213> ORGANISM: Arabidopsis thaliana

<400> SEQUENCE: 55
atgaagttct tggtttcatt ggttatcttc tctcttttct taaacggttt cgcaaccgct 60
caaactctca ttcaagattc ttgcaagaaa gcttttgcga aagacccgca attgtcatac 120
gatttctgcg tcaattctct tacacaagat ccacaaagca aagccgcgac tactctcgaa 180
agtttggtcc tagcatcgac gaagaccgct gcggcaaaaa tcacgaactt gaaaggaatc 240
gttgcacagg atctcaaaga ccagagatat caggatattg tggaagactt aaaactttgc 300
ctcggatttt ataacgatgc taatgatgat ttaacaactg ctttagcgaa cattaaatcg 360
cgtgattatc aaggcgctaa cattaatctg agtgctgctt tggatgtacc aggcaattgc 420
gaggatgatt tcaaggaagc aaaaaagacg tctccgatta ccaacgagaa cagtattttg 480
tttaagacga ttttgattcc tttggctttt actaatatgt tgtaa 525

<210> SEQ ID NO 56
<211> LENGTH: 174
<212> TYPE: PRT
<213> ORGANISM: Arabidopsis thaliana

<400> SEQUENCE: 56

Met Lys Phe Leu Val Ser Leu Val Ile Phe Ser Leu Phe Leu Asn Gly
1 5 10 15

Phe Ala Thr Ala Gln Thr Leu Ile Gln Asp Ser Cys Lys Lys Ala Phe
20 25 30

Ala Lys Asp Pro Gln Leu Ser Tyr Asp Phe Cys Val Asn Ser Leu Thr
35 40 45

Gln Asp Pro Gln Ser Lys Ala Ala Thr Thr Leu Glu Ser Leu Val Leu
50 55 60

Ala Ser Thr Lys Thr Ala Ala Ala Lys Ile Thr Asn Leu Lys Gly Ile
65 70 75 80

Val Ala Gln Asp Leu Lys Asp Gln Arg Tyr Gln Asp Ile Val Glu Asp
85 90 95

Leu Lys Leu Cys Leu Gly Phe Tyr Asn Asp Ala Asn Asp Asp Leu Thr
100 105 110

```
Thr Ala Leu Ala Asn Ile Lys Ser Arg Asp Tyr Gln Gly Ala Asn Ile
        115                 120                 125

Asn Leu Ser Ala Ala Leu Asp Val Pro Gly Asn Cys Glu Asp Asp Phe
    130                 135                 140

Lys Glu Ala Lys Lys Thr Ser Pro Ile Thr Asn Glu Asn Ser Ile Leu
145                 150                 155                 160

Phe Lys Thr Ile Leu Ile Pro Leu Ala Phe Thr Asn Met Leu
                165                 170


<210> SEQ ID NO 57
<211> LENGTH: 1839
<212> TYPE: DNA
<213> ORGANISM: Arabidopsis thaliana

<400> SEQUENCE: 57

atgcctgagg caccaaagat cgcagctttg gaggtttctg atgagagcct cgctgagaag      60

aacaagaaca aactccaatt catcgaagac gtgaccacga acgcagatga tgttcagaga     120

cgagttcttg aagagatcct ttcacgtaat gctgatgtgg agtatcttaa acgacacggg     180

ctcgaaggac gaaccgatcg tgagactttc aaacatatca tgcctgtcgt aacttacgaa     240

gatattcaac ctgagatcaa cagaatcgcc aatggtgata agtctcaagt cctctgttct     300

aaccccatct ctgagttcct cacaagttct gggacttctg gtggagagag gaaactgatg     360

ccaacaatcg aagaggaact agacagaaga tcacttctct acagtctctt gatgcctgtg     420

atggaccagt ttgttcctgg tcttgacaaa ggcaaaggga tgtattttct gtttatcaaa     480

tcagaatcca agacaccagg tggtctccct gctcgtcctg ttttaaccag ttactacaaa     540

tcctctcact tcaaaaacag accttatgat ccttacacca actacacaag tcccaaccaa     600

accatccttt gttctgactc ttaccagagc atgtactctc aaatgctttg tggtttatgc     660

caacacaaag aggttcttcg tgttggtgct gtttttgcct ctggtttcat tagagccatc     720

aagtttcttg agaaacattg gcctgagcta gctcgtgaca ttagaaccgg tactctcagt     780

tccgagataa ccgattcttc ggttcgtgag gcggtcgggg agattcttaa accggatcct     840

aagcttgctg atttcgtcga atctgaatgc aggaagactt cttggcaagg gatcatcact     900

aggctttggc caaacactaa gtatgtggat gtgattgtga ctggaacaat gtcacagtat     960

attccaactc tggattatta cagcaatggt ttgcctcttg tctgcacaat gtatgcttct    1020

tcggagtgtt acttcggtgt gaatctcagg ccactctgca aaccaagtga agtctcttac    1080

actctcatac cgaacatggc gtatttcgag ttcttgcctg ttcataggaa cagtggagtt    1140

actagctcta tcagtcttcc aaaagcactc actgagaaag aacaacaaga gcttgttgat    1200

ctcgtcgatg tcaagcttgg tcaggagtac gagcttgttg tcaccaccta tgctgggctt    1260

tacaggtaca gagtgggtga tgtcctaagc gtggctggtt tcaagaacaa tgcgcctcag    1320

ttcagcttca tatgccgcaa gaacgtggtc ttaagcattg actcggacaa aaccgatgag    1380

gttgagcttc aaaacgcagt taaaaacgcg gtaacacacc ttgttccgtt tgatgcttca    1440

ctctccgagt acactagcta tgcggacaca tcatctatcc cgggccacta tgtcttattc    1500

tgggagctct gcttgaacgg taacacgcca attcctccct cggtcttcga ggattgctgt    1560

ttaaccatag aggaatcact taacagtgtg tatagacaag gaagggtcag tgataagtcc    1620

attggaccat tggagatcaa gatggtcgag tcagggactt tcgataagct catggattat    1680

gcgataagct tgggtgcatc gatcaatcag tacaagacac caaggtgtgt gaagtttgct    1740
```

-continued ccgatcattg agcttttaaa ctctagggtt gttgatagtt acttcagccc caagtgtcct 1800
aaatggtccc ctggtcacaa gcaatggggg agtaactaa 1839

<210> SEQ ID NO 58
<211> LENGTH: 612
<212> TYPE: PRT
<213> ORGANISM: Arabidopsis thaliana

<400> SEQUENCE: 58

Met Pro Glu Ala Pro Lys Ile Ala Ala Leu Glu Val Ser Asp Glu Ser
1 5 10 15

Leu Ala Glu Lys Asn Lys Asn Lys Leu Gln Phe Ile Glu Asp Val Thr
20 25 30

Thr Asn Ala Asp Asp Val Gln Arg Arg Val Leu Glu Glu Ile Leu Ser
35 40 45

Arg Asn Ala Asp Val Glu Tyr Leu Lys Arg His Gly Leu Glu Gly Arg
50 55 60

Thr Asp Arg Glu Thr Phe Lys His Ile Met Pro Val Val Thr Tyr Glu
65 70 75 80

Asp Ile Gln Pro Glu Ile Asn Arg Ile Ala Asn Gly Asp Lys Ser Gln
85 90 95

Val Leu Cys Ser Asn Pro Ile Ser Glu Phe Leu Thr Ser Ser Gly Thr
100 105 110

Ser Gly Gly Glu Arg Lys Leu Met Pro Thr Ile Glu Glu Glu Leu Asp
115 120 125

Arg Arg Ser Leu Leu Tyr Ser Leu Leu Met Pro Val Met Asp Gln Phe
130 135 140

Val Pro Gly Leu Asp Lys Gly Lys Gly Met Tyr Phe Leu Phe Ile Lys
145 150 155 160

Ser Glu Ser Lys Thr Pro Gly Gly Leu Pro Ala Arg Pro Val Leu Thr
165 170 175

Ser Tyr Tyr Lys Ser Ser His Phe Lys Asn Arg Pro Tyr Asp Pro Tyr
180 185 190

Thr Asn Tyr Thr Ser Pro Asn Gln Thr Ile Leu Cys Ser Asp Ser Tyr
195 200 205

Gln Ser Met Tyr Ser Gln Met Leu Cys Gly Leu Cys Gln His Lys Glu
210 215 220

Val Leu Arg Val Gly Ala Val Phe Ala Ser Gly Phe Ile Arg Ala Ile
225 230 235 240

Lys Phe Leu Glu Lys His Trp Pro Glu Leu Ala Arg Asp Ile Arg Thr
245 250 255

Gly Thr Leu Ser Ser Glu Ile Thr Asp Ser Ser Val Arg Glu Ala Val
260 265 270

Gly Glu Ile Leu Lys Pro Asp Pro Lys Leu Ala Asp Phe Val Glu Ser
275 280 285

Glu Cys Arg Lys Thr Ser Trp Gln Gly Ile Ile Thr Arg Leu Trp Pro
290 295 300

Asn Thr Lys Tyr Val Asp Val Ile Val Thr Gly Thr Met Ser Gln Tyr
305 310 315 320

Ile Pro Thr Leu Asp Tyr Tyr Ser Asn Gly Leu Pro Leu Val Cys Thr
325 330 335

Met Tyr Ala Ser Ser Glu Cys Tyr Phe Gly Val Asn Leu Arg Pro Leu
340 345 350

Cys Lys Pro Ser Glu Val Ser Tyr Thr Leu Ile Pro Asn Met Ala Tyr

-continued

```
        355                 360                 365

Phe Glu Phe Leu Pro Val His Arg Asn Ser Gly Val Thr Ser Ser Ile
    370                 375                 380

Ser Leu Pro Lys Ala Leu Thr Glu Lys Glu Gln Gln Glu Leu Val Asp
385                 390                 395                 400

Leu Val Asp Val Lys Leu Gly Gln Glu Tyr Glu Leu Val Val Thr Thr
            405                 410                 415

Tyr Ala Gly Leu Tyr Arg Tyr Arg Val Gly Asp Val Leu Ser Val Ala
            420                 425                 430

Gly Phe Lys Asn Asn Ala Pro Gln Phe Ser Phe Ile Cys Arg Lys Asn
        435                 440                 445

Val Val Leu Ser Ile Asp Ser Asp Lys Thr Asp Glu Val Glu Leu Gln
    450                 455                 460

Asn Ala Val Lys Asn Ala Val Thr His Leu Val Pro Phe Asp Ala Ser
465                 470                 475                 480

Leu Ser Glu Tyr Thr Ser Tyr Ala Asp Thr Ser Ser Ile Pro Gly His
            485                 490                 495

Tyr Val Leu Phe Trp Glu Leu Cys Leu Asn Gly Asn Thr Pro Ile Pro
            500                 505                 510

Pro Ser Val Phe Glu Asp Cys Cys Leu Thr Ile Glu Glu Ser Leu Asn
        515                 520                 525

Ser Val Tyr Arg Gln Gly Arg Val Ser Asp Lys Ser Ile Gly Pro Leu
    530                 535                 540

Glu Ile Lys Met Val Glu Ser Gly Thr Phe Asp Lys Leu Met Asp Tyr
545                 550                 555                 560

Ala Ile Ser Leu Gly Ala Ser Ile Asn Gln Tyr Lys Thr Pro Arg Cys
            565                 570                 575

Val Lys Phe Ala Pro Ile Ile Glu Leu Leu Asn Ser Arg Val Val Asp
            580                 585                 590

Ser Tyr Phe Ser Pro Lys Cys Pro Lys Trp Ser Pro Gly His Lys Gln
        595                 600                 605

Trp Gly Ser Asn
    610
```

<210> SEQ ID NO 59
<211> LENGTH: 669
<212> TYPE: DNA
<213> ORGANISM: Arabidopsis thaliana

<400> SEQUENCE: 59

```
atgacgataa aaagtctctc ttttcttgcg gctctatctc tctttgcttt gacacttcca     60

ttagtaattg cttccgatcc aagccccctt caagactttt gtgttggtgt caacacacca    120

gcagatggcg tgtttgtgaa tggaaagttt tgcaaggatc caaggatagt tttcgcggat    180

gatttctttt tctcgagcct caacagacct ggaaatacaa ataacgcggt tgggtccaac    240

gtgacaaccg tcaatgttaa caaccttgga ggactaaaca ctcttggtat ctcacttgtt    300

cgtatagact atgcacccaa cggtcagaac ccacctcaca cccacccacg tgccaccgag    360

atcttggttg ttcaacaagg aactctactt gtagggttta tctcatcaaa ccaagacgga    420

aaccgtcttt tcgccaaaac actcaacgtg ggtgacgtat ttgtgtttcc agaaggactc    480

atccatttcc agttcaacct aggaggaact ccagcagttg caatcgctgc tttgagcagc    540

caaaacgcag gtgttatcac aattgctaac acaatatttg ggtctaaacc agatgtagac    600

ccgaatgttc ttgcaagagc attccaaatg gatgttaatg cggtcaggaa tttacaagcc    660
```

```
aggttctaa                                                              669


<210> SEQ ID NO 60
<211> LENGTH: 222
<212> TYPE: PRT
<213> ORGANISM: Arabidopsis thaliana

<400> SEQUENCE: 60

Met Thr Ile Lys Ser Leu Ser Phe Leu Ala Ala Leu Ser Leu Phe Ala
1               5                   10                  15

Leu Thr Leu Pro Leu Val Ile Ala Ser Asp Pro Ser Pro Leu Gln Asp
            20                  25                  30

Phe Cys Val Gly Val Asn Thr Pro Ala Asp Gly Val Phe Val Asn Gly
        35                  40                  45

Lys Phe Cys Lys Asp Pro Arg Ile Val Phe Ala Asp Asp Phe Phe Phe
    50                  55                  60

Ser Ser Leu Asn Arg Pro Gly Asn Thr Asn Asn Ala Val Gly Ser Asn
65                  70                  75                  80

Val Thr Thr Val Asn Val Asn Asn Leu Gly Gly Leu Asn Thr Leu Gly
                85                  90                  95

Ile Ser Leu Val Arg Ile Asp Tyr Ala Pro Asn Gly Gln Asn Pro Pro
            100                 105                 110

His Thr His Pro Arg Ala Thr Glu Ile Leu Val Val Gln Gln Gly Thr
        115                 120                 125

Leu Leu Val Gly Phe Ile Ser Ser Asn Gln Asp Gly Asn Arg Leu Phe
    130                 135                 140

Ala Lys Thr Leu Asn Val Gly Asp Val Phe Val Phe Pro Glu Gly Leu
145                 150                 155                 160

Ile His Phe Gln Phe Asn Leu Gly Gly Thr Pro Ala Val Ala Ile Ala
                165                 170                 175

Ala Leu Ser Ser Gln Asn Ala Gly Val Ile Thr Ile Ala Asn Thr Ile
            180                 185                 190

Phe Gly Ser Lys Pro Asp Val Asp Pro Asn Val Leu Ala Arg Ala Phe
        195                 200                 205

Gln Met Asp Val Asn Ala Val Arg Asn Leu Gln Ala Arg Phe
    210                 215                 220


<210> SEQ ID NO 61
<211> LENGTH: 51
<212> TYPE: DNA
<213> ORGANISM: Arabidopsis thaliana

<400> SEQUENCE: 61

ggggacaagt ttgtacaaaa aagcaggctt aagcagagca agtccataag c               51


<210> SEQ ID NO 62
<211> LENGTH: 49
<212> TYPE: DNA
<213> ORGANISM: Arabidopsis thaliana

<400> SEQUENCE: 62

ggggaccact ttgtacaaga aagctgggta tggagtaatt ggcggcaac                  49


<210> SEQ ID NO 63
<211> LENGTH: 53
<212> TYPE: DNA
<213> ORGANISM: Arabidopsis thaliana
```

<400> SEQUENCE: 63
ggggacaagt ttgtacaaaa aagcaggctt aaaaccctcc acggagttaa agc 53

<210> SEQ ID NO 64
<211> LENGTH: 52
<212> TYPE: DNA
<213> ORGANISM: Arabidopsis thaliana

<400> SEQUENCE: 64
ggggaccact ttgtacaaga aagctgggta gcgaatgtgt cgatagcaac ag 52

<210> SEQ ID NO 65
<211> LENGTH: 49
<212> TYPE: DNA
<213> ORGANISM: Arabidopsis thaliana

<400> SEQUENCE: 65
ggggacaagt ttgtacaaaa aagcaggctt atgtgggttg gtgcctaag 49

<210> SEQ ID NO 66
<211> LENGTH: 48
<212> TYPE: DNA
<213> ORGANISM: Arabidopsis thaliana

<400> SEQUENCE: 66
ggggaccact ttgtacaaga aagctgggta gccgtgaggt tgacattg 48

<210> SEQ ID NO 67
<211> LENGTH: 52
<212> TYPE: DNA
<213> ORGANISM: Arabidopsis thaliana

<400> SEQUENCE: 67
ggggacaagt ttgtacaaaa aagcaggctt attctcctcc agcccatcta cc 52

<210> SEQ ID NO 68
<211> LENGTH: 49
<212> TYPE: DNA
<213> ORGANISM: Arabidopsis thaliana

<400> SEQUENCE: 68
ggggaccact ttgtacaaga aagctgggta gaaacaagcc agcgcagac 49

<210> SEQ ID NO 69
<211> LENGTH: 49
<212> TYPE: DNA
<213> ORGANISM: Arabidopsis thaliana

<400> SEQUENCE: 69
ggggacaagt ttgtacaaaa aagcaggctt aagctcagct ctcgtcatc 49

<210> SEQ ID NO 70
<211> LENGTH: 48
<212> TYPE: DNA
<213> ORGANISM: Arabidopsis thaliana

<400> SEQUENCE: 70
ggggaccact ttgtacaaga aagctgggta atctttcccg cccatctc 48

<210> SEQ ID NO 71
<211> LENGTH: 49
<212> TYPE: DNA
<213> ORGANISM: Arabidopsis thaliana

<400> SEQUENCE: 71
ggggacaagt ttgtacaaaa aagcaggctt acgtgcgtat atggaaagc 49

<210> SEQ ID NO 72
<211> LENGTH: 48
<212> TYPE: DNA
<213> ORGANISM: Arabidopsis thaliana

<400> SEQUENCE: 72
ggggaccact ttgtacaaga aagctgggta acaattgcgg gtctttcg 48

<210> SEQ ID NO 73
<211> LENGTH: 51
<212> TYPE: DNA
<213> ORGANISM: Arabidopsis thaliana

<400> SEQUENCE: 73
ggggacaagt ttgtacaaaa aagcaggctt agttggctct gatgtgtttc g 51

<210> SEQ ID NO 74
<211> LENGTH: 52
<212> TYPE: DNA
<213> ORGANISM: Arabidopsis thaliana

<400> SEQUENCE: 74
ggggaccact ttgtacaaga aagctgggta cctcttcttc cctccttctt tc 52

<210> SEQ ID NO 75
<211> LENGTH: 49
<212> TYPE: DNA
<213> ORGANISM: Arabidopsis thaliana

<400> SEQUENCE: 75
ggggacaagt ttgtacaaaa aagcaggctt agcctgtcaa gtcaacaag 49

<210> SEQ ID NO 76
<211> LENGTH: 48
<212> TYPE: DNA
<213> ORGANISM: Arabidopsis thaliana

<400> SEQUENCE: 76
ggggaccact ttgtacaaga aagctgggta gttgcgtatg catgagag 48

<210> SEQ ID NO 77
<211> LENGTH: 49
<212> TYPE: DNA
<213> ORGANISM: Arabidopsis thaliana

<400> SEQUENCE: 77
ggggacaagt ttgtacaaaa aagcaggctt atgggttatg acgctcttg 49

<210> SEQ ID NO 78
<211> LENGTH: 48
<212> TYPE: DNA
<213> ORGANISM: Arabidopsis thaliana

<400> SEQUENCE: 78
ggggaccact ttgtacaaga aagctgggta agtgtgaagc catccatc 48

<210> SEQ ID NO 79
<211> LENGTH: 51
<212> TYPE: DNA

<213> ORGANISM: Arabidopsis thaliana

<400> SEQUENCE: 79
ggggacaagt ttgtacaaaa aagcaggctt acaaagatcg cagctttgga g 51

<210> SEQ ID NO 80
<211> LENGTH: 50
<212> TYPE: DNA
<213> ORGANISM: Arabidopsis thaliana

<400> SEQUENCE: 80
ggggaccact ttgtacaaga aagctgggta caccattggc gattctgttg 50

<210> SEQ ID NO 81
<211> LENGTH: 49
<212> TYPE: DNA
<213> ORGANISM: Arabidopsis thaliana

<400> SEQUENCE: 81
ggggacaagt ttgtacaaaa aagcaggctt aaagctaaga ccggaatgg 49

<210> SEQ ID NO 82
<211> LENGTH: 48
<212> TYPE: DNA
<213> ORGANISM: Arabidopsis thaliana

<400> SEQUENCE: 82
ggggaccact ttgtacaaga aagctgggta tgagagtggc gttacaag 48

<210> SEQ ID NO 83
<211> LENGTH: 50
<212> TYPE: DNA
<213> ORGANISM: Arabidopsis thaliana

<400> SEQUENCE: 83
ggggacaagt ttgtacaaaa aagcaggctt agagaggcat ggtcgatttc 50

<210> SEQ ID NO 84
<211> LENGTH: 51
<212> TYPE: DNA
<213> ORGANISM: Arabidopsis thaliana

<400> SEQUENCE: 84
ggggaccact ttgtacaaga aagctgggta aactccggta gactccacaa c 51

<210> SEQ ID NO 85
<211> LENGTH: 51
<212> TYPE: DNA
<213> ORGANISM: Arabidopsis thaliana

<400> SEQUENCE: 85
ggggacaagt ttgtacaaaa aagcaggctt acgatctgag cacacctgat g 51

<210> SEQ ID NO 86
<211> LENGTH: 50
<212> TYPE: DNA
<213> ORGANISM: Arabidopsis thaliana

<400> SEQUENCE: 86
ggggaccact ttgtacaaga aagctgggta ctgcttcagt ggctgatgac 50

<210> SEQ ID NO 87
<211> LENGTH: 54

<212> TYPE: DNA
<213> ORGANISM: Arabidopsis thaliana

<400> SEQUENCE: 87
ggggacaagt ttgtacaaaa aagcaggctt aatgtttttc tctaaggatc ttcc 54

<210> SEQ ID NO 88
<211> LENGTH: 52
<212> TYPE: DNA
<213> ORGANISM: Arabidopsis thaliana

<400> SEQUENCE: 88
ggggaccact ttgtacaaga aagctgggta ttatgtccaa aacaatacaa gc 52

<210> SEQ ID NO 89
<211> LENGTH: 56
<212> TYPE: DNA
<213> ORGANISM: Arabidopsis thaliana

<400> SEQUENCE: 89
ggggacaagt ttgtacaaaa aagcaggctt aatgaaaagt ttctcatttc ttgcag 56

<210> SEQ ID NO 90
<211> LENGTH: 55
<212> TYPE: DNA
<213> ORGANISM: Arabidopsis thaliana

<400> SEQUENCE: 90
ggggaccact ttgtacaaga aagctgggta ttatggtttt atgaacttgg tctgt 55

<210> SEQ ID NO 91
<211> LENGTH: 49
<212> TYPE: DNA
<213> ORGANISM: Arabidopsis thaliana

<400> SEQUENCE: 91
ggggacaagt ttgtacaaaa aagcaggctt aatgatgacc caaaaacca 49

<210> SEQ ID NO 92
<211> LENGTH: 53
<212> TYPE: DNA
<213> ORGANISM: Arabidopsis thaliana

<400> SEQUENCE: 92
ggggaccact ttgtacaaga aagctgggta ttaattggaa aaattatcgg tgt 53

<210> SEQ ID NO 93
<211> LENGTH: 56
<212> TYPE: DNA
<213> ORGANISM: Arabidopsis thaliana

<400> SEQUENCE: 93
ggggacaagt ttgtacaaaa aagcaggctt aatggagatc accactatca tattcc 56

<210> SEQ ID NO 94
<211> LENGTH: 57
<212> TYPE: DNA
<213> ORGANISM: Arabidopsis thaliana

<400> SEQUENCE: 94
ggggaccact ttgtacaaga aagctgggta tcactttctc cttggataaa tatttgc 57

<210> SEQ ID NO 95

-continued

```
<211> LENGTH: 51
<212> TYPE: DNA
<213> ORGANISM: Arabidopsis thaliana

<400> SEQUENCE: 95

ggggacaagt ttgtacaaaa aagcaggctt aatggacctc ctcttgctgg a              51


<210> SEQ ID NO 96
<211> LENGTH: 55
<212> TYPE: DNA
<213> ORGANISM: Arabidopsis thaliana

<400> SEQUENCE: 96

ggggaccact ttgtacaaga aagctgggta ttaacagttc cttggtttca taacg          55
```

GENES TO ENHANCE DISEASE RESISTANCE IN CROPS

This application is a National Stage application of International Application No. PCT/IB2012/057313, filed Dec. 14, 2012, which claims the benefit of U.S. Provisional Application No. 61/579,700, filed Dec. 23, 2011. This application also claims priority under 35 U.S.C. § 119 to European Patent Application No. 11195696.7, filed Dec. 23, 2011.

REFERENCE TO SEQUENCE LISTING SUBMITTED VIA EFS-WEB

This application is being filed electronically via EFS-Web and includes an electronically submitted sequence listing in .txt format. The .txt file contains a sequence listing entitled "Seq_List.txt" created on Mar. 19, 2014, and is 192,512 bytes in size. The sequence listing contained in this .txt file is part of the specification and is hereby incorporated by reference herein in its entirety.

SUMMARY OF THE INVENTION

The present invention relates to a method of increasing resistance against fungal pathogens in transgenic plants and/or plant cells. In these plants, specific genes are overexpressed or silenced, which show differential expression pattern in *Arabidopsis* and soybean after inoculation with soybean rust. Depending on the activating or inhibitory function of a particular signaling compound overexpression or knock-down of the cognate gene might be used.

Furthermore, the invention relates to transgenic plants and/or plant cells having an increased resistance against fungal pathogens, for example soybean rust and to recombinant expression vectors comprising a sequence that is identical or homologous to a sequence encoding a functional ethylene signaling compound or fragments thereof.

BACKGROUND OF THE INVENTION

The cultivation of agricultural crop plants serves mainly for the production of foodstuffs for humans and animals. Monocultures in particular, which are the rule nowadays, are highly susceptible to an epidemic-like spreading of diseases. The result is markedly reduced yields. To date, the pathogenic organisms have been controlled mainly by using pesticides. Nowadays, the possibility of directly modifying the genetic disposition of a plant or pathogen is also open to man.

Resistance generally means the ability of a plant to prevent, or at least curtail the infestation and colonization by a harmful pathogen. Different mechanisms can be discerned in the naturally occurring resistance, with which the plants fend off colonization by phytopathogenic organisms. These specific interactions between the pathogen and the host determine the course of infection (Schopfer and Brennicke (1999) Pflanzenphysiologie, Springer Verlag, Berlin-Heidelberg, Germany).

With regard to the race specific resistance, also called host resistance, a differentiation is made between compatible and incompatible interactions. In the compatible interaction, an interaction occurs between a virulent pathogen and a susceptible plant. The pathogen survives, and may build up reproduction structures, while the host mostly dies off. An incompatible interaction occurs on the other hand when the pathogen infects the plant but is inhibited in its growth before or after weak development of symptoms. In the latter case, the plant is resistant to the respective pathogen (Schopfer and Brennicke, vide supra). However, this type of resistance is specific for a certain strain or pathogen.

In both compatible and incompatible interactions a defensive and specific reaction of the host to the pathogen occurs. In nature, however, this resistance is often overcome because of the rapid evolutionary development of new virulent races of the pathogens (Neu et al. (2003) American Cytopathol. Society, MPMI 16 No. 7: 626-633).

Most pathogens are plant-species specific. This means that a pathogen can induce a disease in a certain plant species, but not in other plant species (Heath (2002) Can. J. Plant Pathol. 24: 259-264). The resistance against a pathogen in certain plant species is called non-host resistance. The non-host resistance offers strong, broad, and permanent protection from phytopathogens. Genes providing non-host resistance provide the opportunity of a strong, broad and permanent protection against certain diseases in non-host plants. In particular such a resistance works for different strains of the pathogen.

Fungi are distributed worldwide. Approximately 100 000 different fungal species are known to date. The rusts are of great importance. They can have a complicated development cycle with up to five different spore stages (spermatium, aecidiospore, uredospore, teleutospore and basidiospore).

During the infection of plants by pathogenic fungi, different phases are usually observed. The first phases of the interaction between phytopathogenic fungi and their potential host plants are decisive for the colonization of the plant by the fungus. During the first stage of the infection, the spores become attached to the surface of the plants, germinate, and the fungus penetrates the plant. Fungi may penetrate the plant via existing ports such as stomata, lenticels, hydatodes and wounds, or else they penetrate the plant epidermis directly as the result of the mechanical force and with the aid of cell-wall-digesting enzymes. Specific infection structures are developed for penetration of the plant. The soybean rust *Phakopsora pachyrhizi* directly penetrates the plant epidermis. After crossing the epidermal cell, the fungus reaches the intercellular space of the mesophyll, where the fungus starts to spread through the leaves. To acquire nutrients the fungus penetrates mesophyll cells and develops haustoria inside the mesophyl cell. During the penetration process the plasma membrane of the penetrated mesophyll cell stays intact. Therefore the soybean rust fungus establishes a biotrophic interaction with soybean.

Immediately after the attachment of the spore to the plant cell, the plants sense the presence of the pathogen. Mostly the presence of the pathogen is sensed via so called PAMP receptors, a class of trans-membrane receptor like kinases recognizing conserved pathogen associated molecules (e.g. flagellin or chitin). Downstream of the PAMP receptors, a signaling cascade is initiated leading to the elicitation of defense reactions. On the other hand the pathogen is counteracting the defense related signaling pathway by injecting so-called effector proteins into the host cell. The effectors lead to the inhibition, weakening or deregulation of the defense regulation, in a way that the pathogen can further colonize the plant. But these effectors might also be recognized by the plant by major R- (resistance) genes of the NBS-LRR class, leading to a strong defense response.

During million years of evolution, every pathogen shaped its effector set in a way to block exactly those defense reactions that are most effective against the particular pathogen. So, the most interesting genes, in terms of creating a disease resistant plant, are those genes that are suppressed by the pathogen in their respective host plant.

Immediately after recognition of a potential pathogen the plant starts to elicit defense reactions.

Soybean rust has become increasingly important in recent times. The disease may be caused by the biotrophic rusts *Phakopsora pachyrhizi* (Sydow) and *Phakopsora meibomiae* (Arthur). They belong to the class Basidiomycota, order Uredinales, family Phakopsoraceae. Both rusts infect a wide spectrum of leguminosic host plants. *P. pachyrhizi*, also referred to as Asian rust, is an aggressive pathogen on soy (*Glycine max, Soja hispida* or *Soja max*), and is therefore, at least currently, of great importance for agriculture. *P. pachyrhizi* can be found in nearly all tropical and subtropical soy growing regions of the world. *P. pachyrhizi* is capable of infecting 31 species from 17 families of the Leguminosae under natural conditions and is capable of growing on further 60 species under controlled conditions (Sinclair et al. (eds.), Proceedings of the rust workshop (1995), National SoyaResearch Laboratory, Publication No. 1 (1996); Rytter J. L. et al., Plant Dis. 87, 818 (1984)). *P. meibomiae* has been found in the Caribbean Basin and in Puerto Rico, and has not caused substantial damage as yet.

*P. pachyrhizi* can currently be controlled in the field only by means of fungicides. Soy plants with resistance to the entire spectrum of the isolates are not available. When searching for resistant plants, four dominant genes Rpp1-4, which mediate resistance of soy to *P. pachyrhizi*, were discovered. The resistance was lost rapidly, as *P. pychyrhizi* develops new virulent races.

In recent years, fungal diseases, e.g. soybean rust, has gained in importance as pest in agricultural production. There was therefore a demand in the prior art for developing methods to control fungi and to provide fungal resistant plants.

Much research has been performed on the field of powdery and downy mildew infecting the epidermal layer of plants. However, the problem to cope with soybean rust which infects the mesophyll remains unsolved. This problem is worsened by the fact that prior to the present invention no prediction could be made regarding plant genes involved in resistance against soybean rust. Thus, constructing resistant plants by means of genetic modification and/or breeding was a matter of try and error, severely reducing the chances of obtaining resistant plants. Also, as no prediction could be made regarding plant genes involved in resistance against soybean rust, it was also not possible to screen in any technically meaningful way for chemical agents increasing expression of genes involved in soybean rust resistance.

BRIEF SUMMARY OF THE INVENTION

The object of the present invention is thus to provide means for conferring, improving or modifying resistance of plant cells and plants against infections by a fungal pathogen, preferably against infections by a pathogen of the class Basidiomycota, preferably of the order Uredinales, more preferably of the family Phakopsoraceae, even more preferably against soybean rust, even more preferably of the genus *Phacopsora*, most preferably of the species *Phakopsora pachyrhizi* (Sydow) and/or *Phakopsora meibomiae* (Arthur). The invention further provides corresponding nucleic acids, proteins, vectors, host cells, plant cells and plants. Also, it was an object of the present invention to provide means and methods for identification of agents for conferring, increasing or modifying resistance against the fungal infections of a plant as compared to a corresponding wild type plant.

Surprisingly the inventors found new genes mediating resistance of soybean against soybean rust by comparing gene expression in mutants of a non-host species for soybean rust, i.e. *Arabidopsis thaliana*. Microscopically ~90% of the fungi were stopped by the plant defense already in the epidermal cell layer. However, the *Arabidopsis* pen2 mutant (Lipka et al. 2005 Science 310: 1180-1183) allows the penetration of soybean rust into the mesophyll cell layers, but nearly no haustoria could be built by soybean rust in the *Arabidopsis* pen2 mutant. A third mutant *Arabidopsis* pen2 pad4 sag101 (Lipka et al. 2005 Science 310: 1180-1183) allows beside the efficient penetration of ASR into the mesophyll, the formation haustoria (~30% of interactions). By comparing genes up-regulated during the time of mesophyll based defense reactions (48 hpi) in the wild-type and the different mutants the inventors isolated the genes responsible for the mesophyll based resistance reactions in *Arabidopsis*, which is normally obscured by the strong epidermal defense in *Arabidopsis* wild type. Using the described method to select candidate genes, the inventors were able to identify new candidates providing resistance in *Arabidopsis* and transferred their function to soybean (and named them CL-genes).

BRIEF DESCRIPTION OF THE TABLES AND SEVERAL VIEWS OF THE DRAWINGS

Table 1 shows the list of the candidates selected by the method described in Example 1-3.

Table 2 lists primer sequences for cloning of silencing constructs for *Arabidopsis* transformation.

Table 3 shows a compilation of nucleic acids and amino acids for the respective CL genes together with the corresponding sequence identifier.

FIG. 1 shows the results of the expression analysis of the CL-gene induction after inoculation with soybean rust as described in Example 4. FIG. 1*a* shows the result of confirmation of CL-gene induction in *Arabidopsis* pen2 mutant inoculated with soybean rust 2 days past inoculation (dpi). FIG. 1*b* shows the similar induction pattern of CL7 and GLP9 gene expression in *Arabidopsis, Arabidopsis* pen2 and the triple mutant pen2 pad4 sag101 (p2p4s101) inoculated with soybean rust 2 days past inoculation (dpi). Relative transcript abundance was analyzed by RT-qPCR. Actin2 (ACT2) was used for normalization of candidate gene expression. Mean values of three independent inoculations are shown. Similar to FIG. 1*b* the FIG. 1*c* shows the induction of gene expression of CL4, CL7 and CL22 in leaves of *Arabidopsis* wild type, pen2, and the triple mutant pen2 pad4 sag101 plants at two days after inoculation with *P. pachyrhizi*. RNA was extracted from treated leaves after 48 h and relative transcript abundance of A: CL4, B: CL7 and C: CL22 was analyzed by RT-qPCR. Actin2 (ACT2) was used for normalization of candidate gene expression. Mean values of three independent inoculations are shown.

Figure 2:
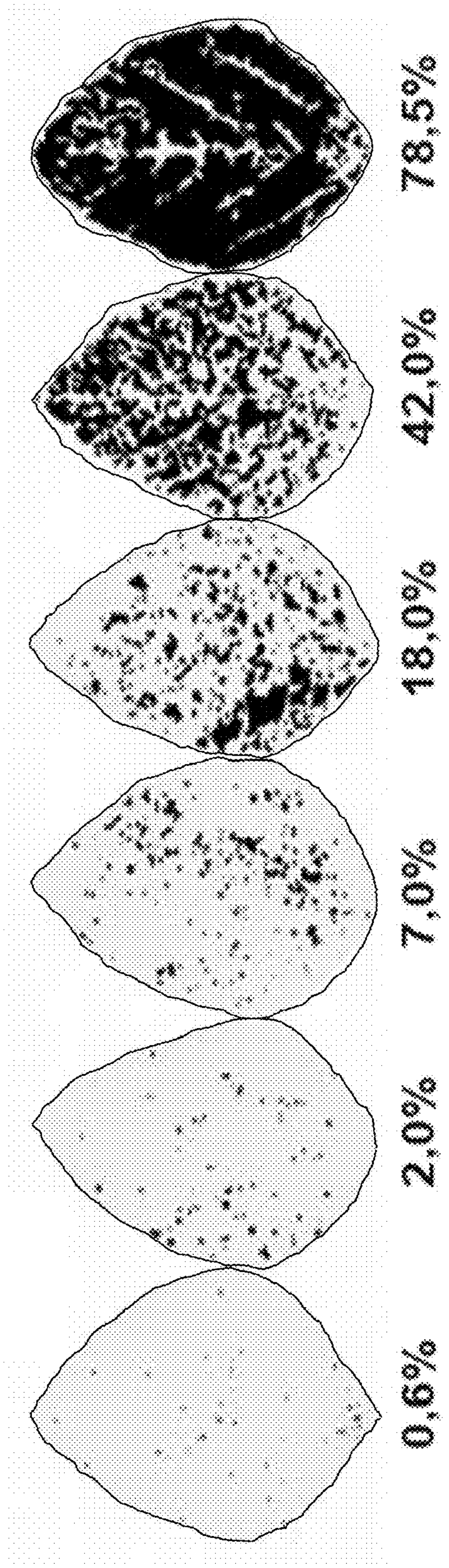

FIG. 2 shows the scoring system used to determine the level of diseased leaf area of wildtype and transgenic soy plants against the rust fungus *P. pachyrhizi.*

Figure 3:
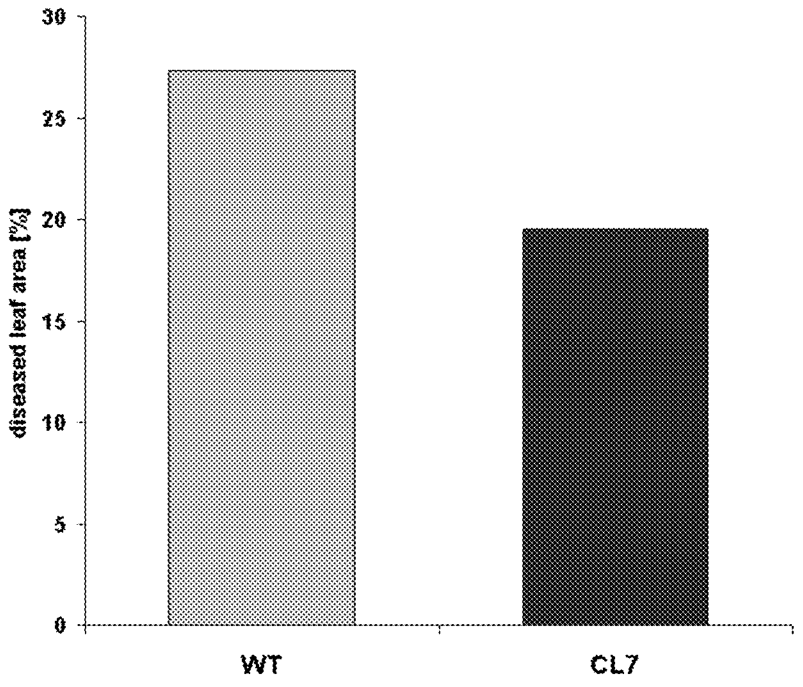

FIG. 3 shows the result of the scoring of 23 transgenic soy plants expressing the CL7 overexpression vector construct. T0 soybean plants expressing CL7 protein were inoculated with spores of *Phakopsora pachyrhizi*. The evaluation of the diseased leaf area on all leaves was performed 14 days after inoculation. The average of the percentage of the leaf area showing fungal colonies or strong yellowing/browning on all leaves was considered as diseased leaf area. At all 23 soybean T0 plants expressing CL7 (expression checked by RT-PCR) were evaluated in parallel to non-transgenic control plants. The average of the diseased leaf area is shown in FIG. 3. Overexpression of CL7 significantly ($p<0.01$) reduces the diseased leaf area in comparison to non-transgenic control plants by 28%.

Figure 4:
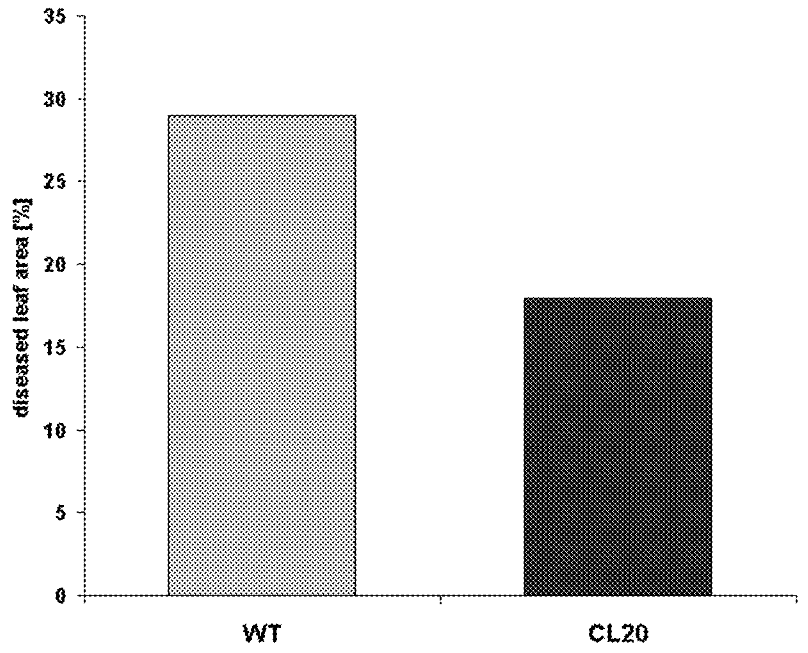

FIG. 4 shows the result of the scoring of 25 transgenic soy plants expressing the CL20 overexpression vector construct. T0 soybean plants expressing CL20 protein were inoculated with spores of *Phakopsora pachyrhizi*. The evaluation of the diseased leaf area on all leaves was performed 14 days after inoculation. The average of the percentage of the leaf area showing fungal colonies or strong yellowing/browning on all leaves was considered as diseased leaf area. At all 25 soybean T0 plants expressing CL20 (expression checked by RT-PCR) were evaluated in parallel to non-transgenic control plants. The median of the diseased leaf area is shown in FIG. 4. Overexpression of CL20 significantly ($p<0.01$) reduces the diseased leaf area in comparison to non-transgenic control plants by 38%.

Figure 5:
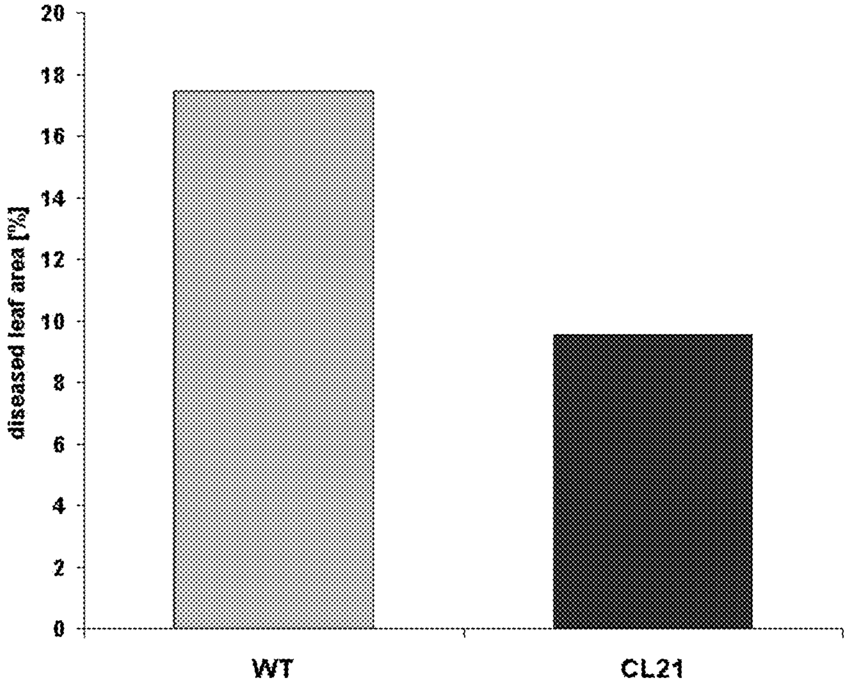

FIG. 5 shows the result of the scoring of 29 transgenic soy plants expressing the CL21 overexpression vector construct. T0 soybean plants expressing CL21 protein were inoculated with spores of *Phakopsora pachyrhizi*. The evaluation of the diseased leaf area on all leaves was performed 14 days after inoculation. The average of the percentage of the leaf area showing fungal colonies or strong yellowing/browning on all leaves was considered as diseased leaf area. At all 29 soybean T0 plants expressing CL21 (expression checked by RT-PCR) were evaluated in parallel to non-transgenic control plants. The median of the diseased leaf area is shown in FIG. 5. Overexpression of CL21 significantly ($p<0.05$) reduces the diseased leaf area in comparison to non-transgenic control plants by 45%.

Figure 6:
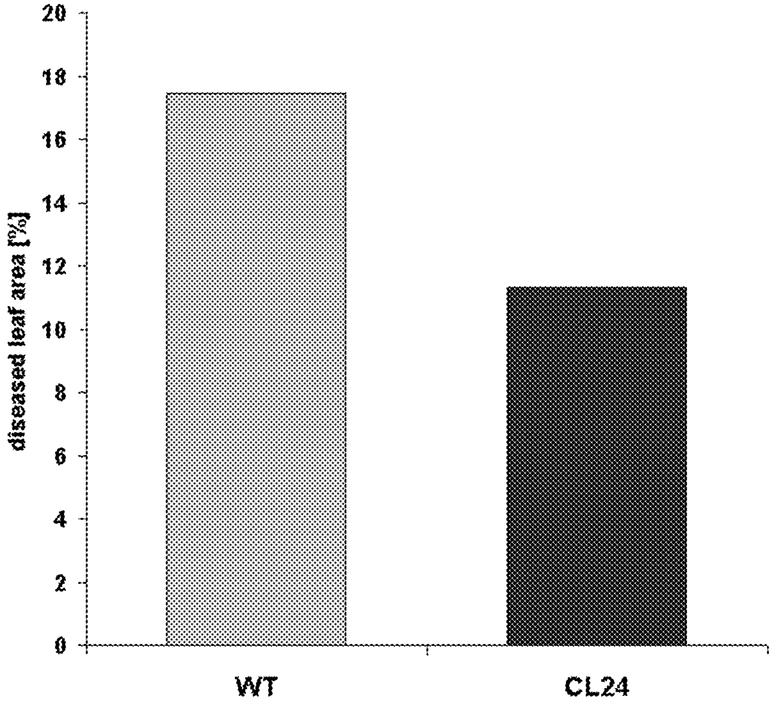

FIG. 6 shows the result of the scoring of 17 transgenic soy plants expressing the CL24 overexpression vector construct. T0 soybean plants expressing CL24 protein were inoculated with spores of *Phakopsora pachyrhizi*. The evaluation of the diseased leaf area on all leaves was performed 14 days after inoculation. The average of the percentage of the leaf area showing fungal colonies or strong yellowing/browning on all leaves was considered as diseased leaf area. At all 17 soybean T0 plants expressing CL24 (expression checked by RT-PCR) were evaluated in parallel to non-transgenic control plants. The median of the diseased leaf area is shown in FIG. 6. Overexpression of CL24 significantly ($p<0.05$) reduces the diseased leaf area in comparison to non-transgenic control plants by 35%.

Figure 7:
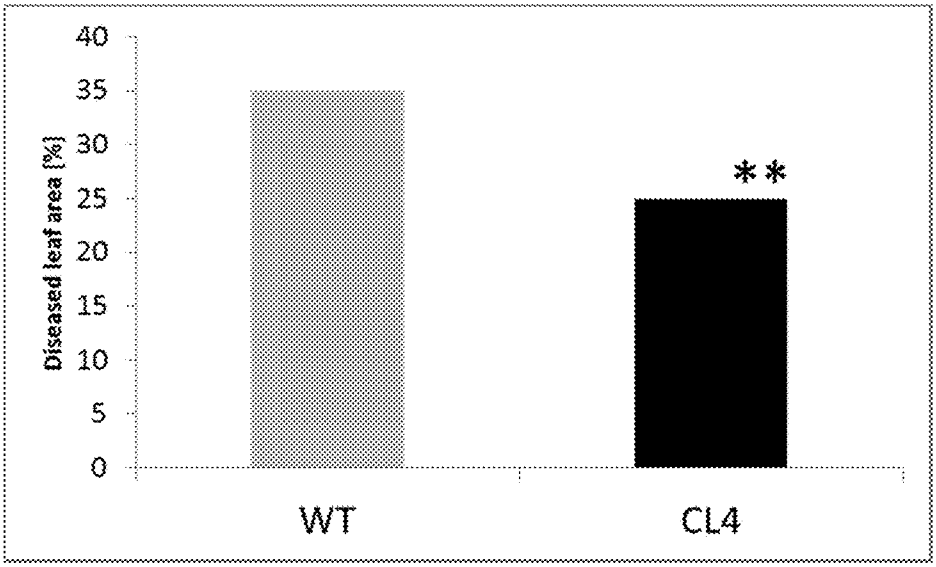

FIG. 7 shows the result of the scoring of 44 transgenic soy plants from 5 independent transgenic events expressing the CL4 overexpression vector construct. T1 soybean plants expressing CL4 protein were inoculated with spores of *Phakopsora pachyrhizi*. The evaluation of the diseased leaf area on all leaves was performed 14 days after inoculation. The average of the percentage of the leaf area showing fungal colonies or strong yellowing/browning on all leaves was considered as diseased leaf area. At all 44 soybean T1 plants from 5 independent events expressing CL4 (expression checked by RT-PCR) were evaluated in parallel to non-transgenic control plants. The median of the diseased leaf area is shown in FIG. 7. Overexpression of CL4 significantly ($p<0.01$) reduces the diseased leaf area in comparison to non-transgenic control plants by 28.5%.

Figure 8:
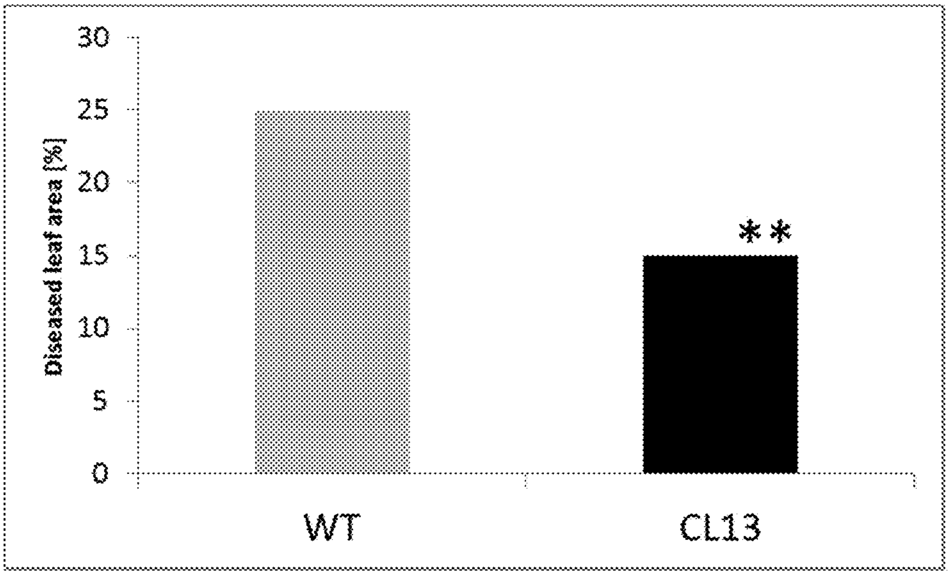

FIG. 8 shows the result of the scoring of 24 transgenic soy T0 plants expressing the CL13 overexpression vector construct. T0 soybean plants expressing CL13 protein were inoculated with spores of *Phakopsora pachyrhizi*. The evaluation of the diseased leaf area on all leaves was performed 14 days after inoculation. The average of the percentage of the leaf area showing fungal colonies or strong yellowing/browning on all leaves was considered as diseased leaf area. At all 24 soybean T0 plants expressing CL13 (expression checked by RT-PCR) were evaluated in parallel to non-transgenic control plants. The median of the diseased leaf area is shown in FIG. 8. Overexpression of CL13 significantly ($p<0.01$) reduces the diseased leaf area in comparison to non-transgenic control plants by 40%.

Figure 9:
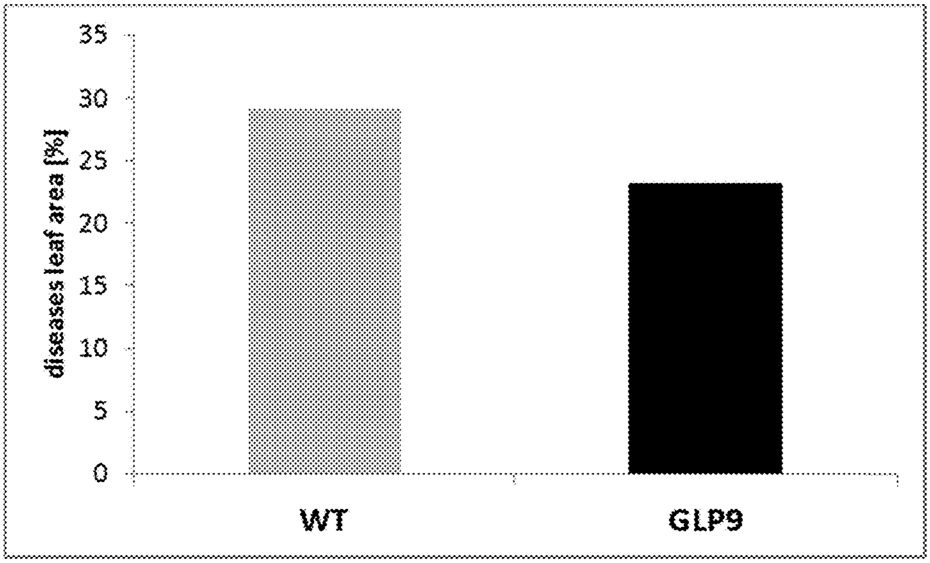

FIG. 9 shows the result of the scoring of 28 transgenic soy T0 plants from 11 independent transgenic events expressing the GLP9 overexpression vector construct. T0 soybean plants expressing GLP9 protein were inoculated with spores of *Phakopsora pachyrhizi*. The evaluation of the diseased leaf area on all leaves was performed 14 days after inoculation. The average of the percentage of the leaf area showing fungal colonies or strong yellowing/browning on all leaves was considered as diseased leaf area. At all 28 soybean T0 plants from 11 independent events expressing GLP9 (expression checked by RT-PCR) were evaluated in parallel to non-transgenic control plants. The median of the diseased leaf area of 11 independent events is shown in FIG. 9. Overexpression of GLP9 reduces the median of the diseased leaf area in comparison to non-transgenic control plants by 20.2%.

Figure 10:
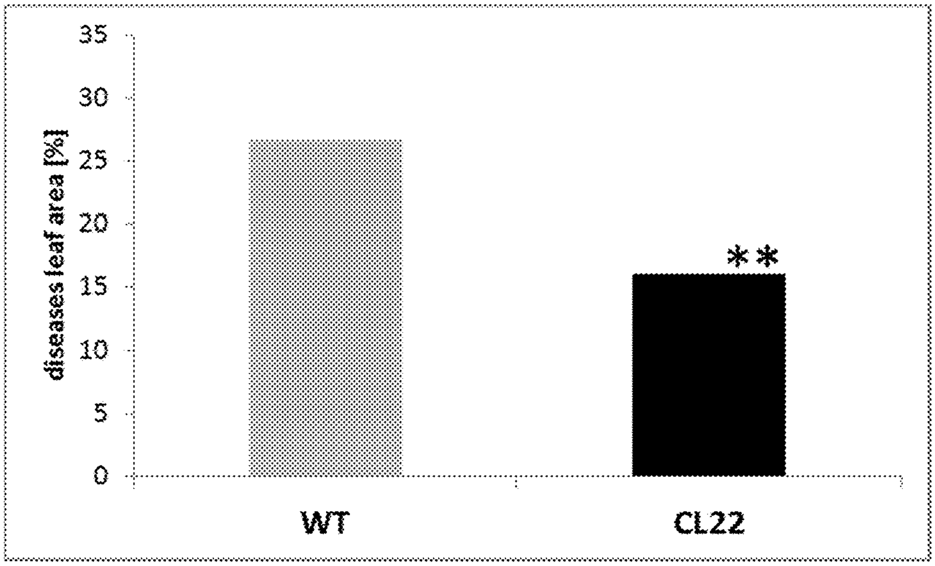

FIG. 10 shows the result of the scoring of 26 transgenic soy T0 plants, derived from 10 independent events expressing the CL22 overexpression vector construct. T0 soybean plants expressing CL22 protein were inoculated with spores of *Phakopsora pachyrhizi*. The evaluation of the diseased leaf area on all leaves was performed 14 days after inoculation. The average of the percentage of the leaf area showing fungal colonies or strong yellowing/browning on all leaves was considered as diseased leaf area. At all 26 soybean T0 plants expressing CL22 (expression checked by RT-PCR) were evaluated in parallel to non-transgenic control plants. The median of the diseased leaf area is shown in FIG. 10. Overexpression of CL22 significantly ($p<0.01$) reduces the diseased leaf area in comparison to non-transgenic control plants by 40%.

Figure 11:
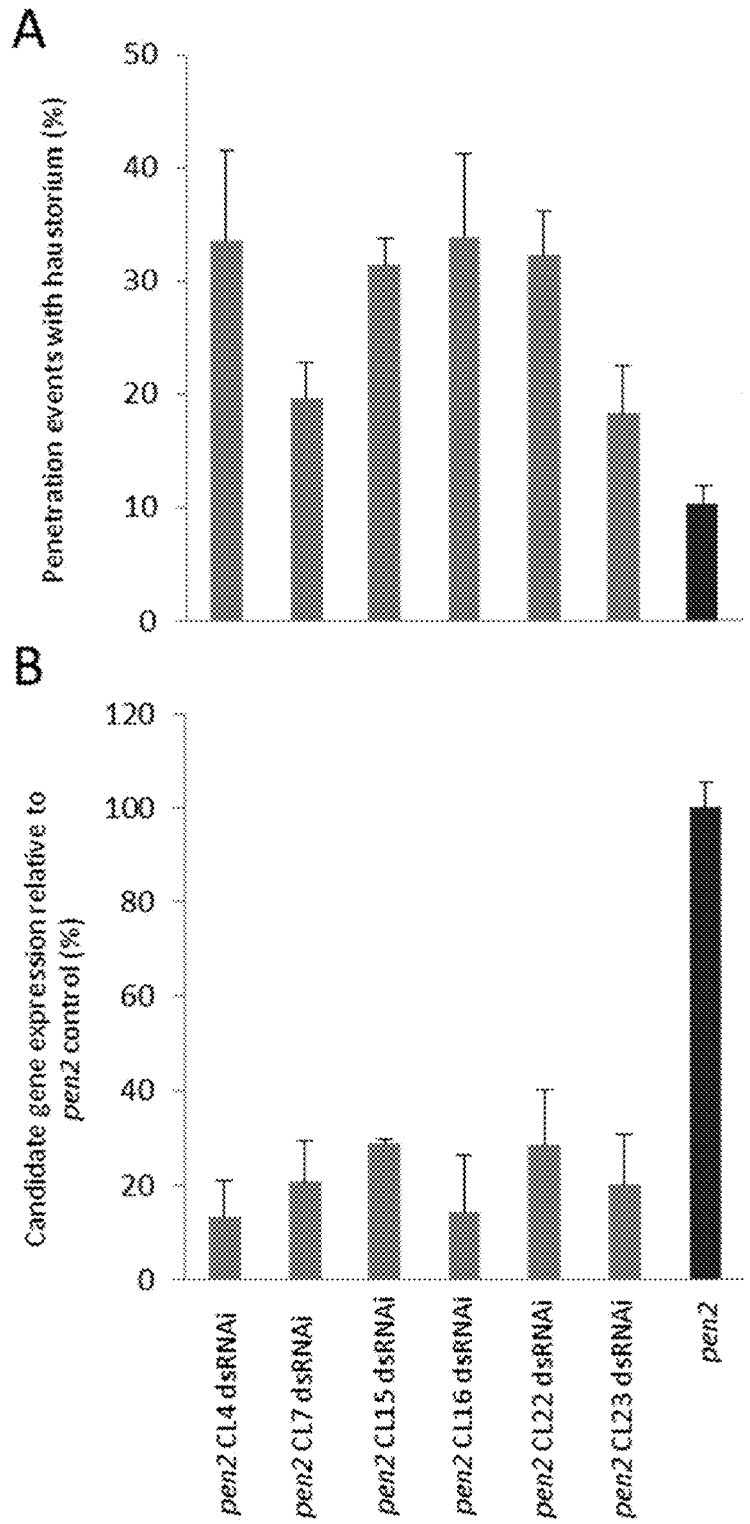

FIG. 11 shows the reduction of resistance by candidate gene inactivation in selected *Arabidopsis* dsRNAi lines. Leaves of *Arabidopsis* pen2 (control) and CL gene dsRNAi transgenic lines (all in gl1 mutant background) were inoculated with *Phakopsora pachyrhizi* and harvested at 2 dpi for determination of candidate gene expression and microscopic analysis of resistance. Average frequency of haustoria formation (A) and average expression of candidate gene (B) in inoculated leaves is shown for several dsRNAi lines relative to pen2 control plants. Mean values were calculated only from those dsRNAi lines that showed a severe reduction (more than 50%) in candidate gene abundance. Knock-down of CL4, CL7, CL15, CL16, CL22 and CL23 lead to an increased susceptibility in *Arabidopsis* pen2, indicating for an involvement of these genes in resistance against soybean rust.

FIG. 12 shows the description of the sequence listing.

DETAILED DESCRIPTION OF THE INVENTION

As described above and further explained by the examples hereinafter, it has now been found that proteins encoded by the nucleic acids of the invention are able to confer improved resistance to plant cells and plants against infections by a fungal pathogen, preferably against infections by a pathogen of the class Basidiomycota, preferably of order Uredinales, more preferably of family Phakopsoraceae, even more preferably against soybean rust, even more preferably of genus *Phacopsora*, most preferably of species *Phakopsora pachyrhizi* (Sydow) and/or *Phakopsora meibomiae* (Arthur).

The nucleic acids of the present invention can confer such resistance to plant cells and plants that are, in their corresponding wild type, prone to or not resistant to such infections. Susceptibility of infection is determined by exposing a plant to the respective fungal pathogen, allowing time for the pathogen to infect the plant, and determine if the plant leaves show signs of infection, e.g. discoloured or wrinkled areas.

The present invention is thus directed to CL nucleic acids and the use of a CL nucleic acid for enhancing fungal resistance in a plant. Preferably the CL nucleic acid is an isolated nucleic acid molecule consisting of or comprising a nucleic acid selected from the group consisting of:

(i) a nucleic acid having in increasing order of preference at least 40%, at least 50%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 3, 4, 35, 33, 7, 49, 50, 47, 53, 25, 41, 29, 23, 55, 1, 21, 31, 27, 9, 57, 17, 19, 37, 11, 12, 13, 39, 43, 45 or 59, preferably SEQ ID NO: 1, 7, 11, 12, 13, or 59, or a functional fragment, derivative, orthologue, or paralogue thereof;

(ii) a nucleic acid encoding a CL protein having in increasing order of preference at least 40%, at least 50%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence represented by SEQ ID NO: 5, 6, 36, 34, 8, 51, 52, 48, 54, 26, 42, 30, 24, 56, 2, 22, 32, 28, 10, 58, 18, 20, 38, 14, 15, 16, 40, 44, 46 or 60, preferably SEQ ID NO: 2, 8, 14, 15, 16, or 60, or a functional fragment, derivative, orthologue, or paralogue thereof; preferably the CL protein has essentially the same biological activity as a CL protein encoded by SEQ ID NO: 3, 4, 35, 33, 7, 49, 50, 47, 53, 25, 41, 29, 23, 55, 1, 21, 31, 27, 9, 57, 17, 19, 37, 11, 12, 13, 39, 43, 45 or 59, preferably the CL protein confers enhanced fungal resistance relative to control plants;

(iii) a nucleic acid encoding the same CL protein as the CL nucleic acids of (i) or (ii) above, but differing from the CL nucleic acids of (i) or (ii) above due to the degeneracy of the genetic code.

Percentages of identity of a nucleic acid are indicated with reference to the entire nucleotide region given in a sequence specifically disclosed herein.

The CL nucleic acids described herein are useful in the constructs, methods, plants, harvestable parts and products of the invention.

Another embodiment of the present invention are CL polypeptides. Preferably, the CL polypeptide is a polypeptide consisting of or comprising an amino acid sequence selected from the group consisting of:

(i) an amino acid sequence having in increasing order of preference at least 40%, at least 50%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence represented by SEQ ID NO: 5, 6, 36, 34, 8, 51, 52, 48, 54, 26, 42, 30, 24, 56, 2, 22, 32, 28, 10, 58, 18, 20, 38, 14, 15, 16, 40, 44, 46 or 60, preferably SEQ ID NO: 2, 8, 14, 15, 16, or 60; or a functional fragment, derivative, orthologue, or paralogue thereof; preferably the CL protein has essentially the same biological activity as a CL protein encoded by SEQ ID NO: 3, 4, 35, 33, 7, 49, 50, 47, 53, 25, 41, 29, 23, 55, 1, 21, 31, 27, 9, 57, 17, 19, 37, 11, 12, 13, 39, 43, 45 or 59; preferably the CL protein confers enhanced fungal resistance relative to control plants; or (ii) an amino acid sequence encoded by a nucleic acid having in increasing order of preference at least 40%, at least 50%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 3, 4, 35, 33, 7, 49, 50, 47, 53, 25, 41, 29, 23, 55, 1, 21, 31, 27, 9, 57, 17, 19, 37, 11, 12, 13, 39, 43, 45 or 59, preferably SEQ ID NO: 1, 7, 11, 12, 13, or 59, or a functional fragment, derivative, orthologue, or paralogue thereof; preferably the CL protein confers enhanced fungal resistance relative to control plants.

Preferably, the CL protein consists of or comprises an amino acid sequence represented by SEQ ID NO: 5, 6, 36, 34, 8, 51, 52, 48, 54, 26, 42, 30, 24, 56, 2, 22, 32, 28, 10, 58, 18, 20, 38, 14, 15, 16, 40, 44, 46 or 60 with one or more conservative amino acid substitutions of the corresponding amino acid residues of SEQ ID NO: 5, 6, 36, 34, 8, 51, 52, 48, 54, 26, 42, 30, 24, 56, 2, 22, 32, 28, 10, 58, 18, 20, 38, 14, 15, 16, 40, 44, 46 or 60. Preferably 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 1-10, 10-20, 20-30, 40-50, 50-60, 60-70, 70-80, 80-90, 90-100, 100-110, 110-120, or 120-130 amino acid residues of SEQ ID NO: 5, 6, 36, 34, 8, 51, 52, 48, 54, 26, 42, 30, 24, 56, 2, 22, 32, 28, 10, 58, 18, 20, 38, 14, 15, 16, 40, 44, 46 or 60 are conservative amino acid substitutions of the corresponding amino acid residue of SEQ ID NO: 5, 6, 36, 34, 8, 51, 52, 48, 54, 26, 42, 30, 24, 56, 2, 22, 32, 28, 10, 58, 18, 20, 38, 14, 15, 16, 40, 44, 46 or 60.

More preferably, the CL protein consists of or comprises an amino acid sequence having at least 40%, at least 50%, at least 60%, at least 65%, at least 70%, at least 75%, at least 80%, at least 85%, at least 90%, at least 95%, at least 98% or at least 99% sequence identity with an amino acid sequence as represented by SEQ ID NO: 5, 6, 36, 34, 8, 51, 52, 48, 54, 26, 42, 30, 24, 56, 2, 22, 32, 28, 10, 58, 18, 20, 38, 14, 15, 16, 40, 44, 46 or 60, wherein at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, or at least 30 of the non-identical amino acid residues, or wherein 1-10, 10-20, 20-30, 40-50, 50-60, 60-70, 70-80, 80-90 or 90-100 or even all of the non-identical amino acid residues are conservative amino acid substitutions of the corresponding amino acid residue of SEQ ID NO: 5, 6, 36, 34, 8, 51, 52, 48, 54, 26, 42, 30, 24, 56, 2, 22, 32, 28, 10, 58, 18, 20, 38, 14, 15, 16, 40, 44, 46 or 60.

Percentages of identity of a polypeptide or protein are indicated with reference to the entire amino acid sequence specifically disclosed herein.

The terms “protein” and “polypeptide” are used herein interchangeably.

The CL proteins described herein are useful in the constructs, methods, plants, harvestable parts and products of the invention.

According to the invention there is thus provided a plant cell comprising, as a heterologous nucleic acid, a nucleic acid selected from the group consisting of a) nucleic acids comprising any of the nucleic acid sequences SEQ ID NO: 3, 4, 35, 33, 7, 49, 50, 47, 53, 25, 41, 29, 23, 55, 1, 21, 31, 27, 9, 57, 17, 19, 37, 11, 12, 13, 39, 43, 45 or 59,
b) nucleic acids coding for a polypeptide comprising any of the amino acid sequences SEQ ID NO: 5, 6, 36, 34, 8, 51, 52, 48, 54, 26, 42, 30, 24, 56, 2, 22, 32, 28, 10, 58, 18, 20, 38, 14, 15, 16, 40, 44, 46 or 60, and
c) nucleic acids coding for a polypeptide having an amino acid sequence identity of at least 40% to any of the amino acid sequences SEQ ID NO: 5, 6, 36, 34, 8, 51, 52, 48, 54, 26, 42, 30, 24, 56, 2, 22, 32, 28, 10, 58, 18, 20, 38, 14, 15, 16, 40, 44, 46 or 60.

According to the invention, the plant cells comprise the above nucleic acids as heterologous nucleic acids. That is to say that any of the following criteria are met:

a) The nucleic acids are not part of the genome of the corresponding wild type plant, or
b) the nucleic acids are not expressed in the genome of the corresponding wild type plant, e.g. susceptibility of the wild type plant to fungal infections does not differ from the susceptibility of a corresponding knockout plant, or
c) the copy number of the nucleic acids in functional form, i.e. that can be expressed by the plant cell, is higher in the plant cells according to the present invention compared to the corresponding wild type plant, or
d) the nucleic acid is under the control of a transcription regulating element which allows to increase transcription of the nucleic acid.

Preferably, the criteria a) and/or b) apply; most preferably criterium a) applies. For the purposes of the present invention, the term “wild type plant” refers to the plant community to which the plant transformed according to the present invention originally belonged to.

The nucleic acids of subgroup c) preferably are similar to the nucleic acids of subgroup a) and/or b). That is, they code for a polypeptide the amino acid sequence of which has a degree of identity of at least 40% to one or more of the amino acid sequences SEQ ID NO: 5, 6, 36, 34, 8, 51, 52, 48, 54, 26, 42, 30, 24, 56, 2, 22, 32, 28, 10, 58, 18, 20, 38, 14, 15, 16, 40, 44, 46 or 60.

Such sequences can differ from the sequences of SEQ ID NO: 3, 4, 35, 33, 7, 49, 50, 47, 53, 25, 41, 29, 23, 55, 1, 21, 31, 27, 9, 57, 17, 19, 37, 11, 12, 13, 39, 43, 45 or 59. For example, the nucleic acids may code for a protein consisting of any of the amino acid sequences SEQ ID NO: 5, 6, 36, 34, 8, 51, 52, 48, 54, 26, 42, 30, 24, 56, 2, 22, 32, 28, 10, 58, 18, 20, 38, 14, 15, 16, 40, 44, 46 or 60 but differ from the corresponding nucleic acid sequence of SEQ ID NO: 3, 4, 35, 33, 7, 49, 50, 47, 53, 25, 41, 29, 23, 55, 1, 21, 31, 27, 9, 57, 17, 19, 37, 11, 12, 13, 39, 43, 45 or 59 due to the degeneration of the genetic code, i.e. by exchanging a codon for another codon coding for the same amino acid. Such exchange may for example allow to optimize the nucleic acid according to the codon preference of the respective plant cell or plant, thereby allowing an improvement of expression of the respective gene.

For *Glycine max*, the codon preference inherent in the plant cells is as follows (the most preferred codon per amino acid is marked by an asterisk):

| Codon | Frequency [per thousand] | [number] | Codon | Frequency [per thousand] | [number] | Codon | Frequency [per thousand] | [number] | Codon | Frequency [per thousand] | [number] |
|---|---|---|---|---|---|---|---|---|---|---|---|
| UUU | 21.2* | (10493) | UCU | 18.4* | (9107) | UAU | 15.7* | (7779) | UGU | 8.1* | (3995) |
| UUC | 21.2 | (10487) | UCC | 12.9 | (6409) | UAC | 14.9 | (7367) | UGC | 8.0 | (3980) |
| UUA | 9.2 | (4545) | UCA | 15.6 | (7712) | UAA | 0.9 | (463) | UGA | 1.0 | (480) |
| UUG | 22.9 | (11340) | UCG | 4.8 | (2397) | UAG | 0.5 | (263) | UGG | 13.0* | (6412) |
| CUU | 23.9* | (11829) | CCU | 18.9 | (9358) | CAU | 14.0* | (6930) | CGU | 6.6 | (3291) |
| CUC | 17.1 | (8479) | CCC | 10.1 | (5010) | CAC | 11.6 | (5759) | CGC | 6.2 | (3093) |
| CUA | 8.5 | (4216) | CCA | 19.1* | (9461) | CAA | 20.5* | (10162) | CGA | 4.1 | (2018) |
| CUG | 12.7 | (6304) | CCG | 4.7 | (2312) | CAG | 16.2 | (8038) | CGG | 3.1 | (1510) |
| AUU | 25.1* | (12411) | ACU | 17.1* | (8490) | AAU | 22.4 | (11088) | AGU | 12.6 | (6237) |
| AUC | 16.3 | (8071) | ACC | 14.3 | (7100) | AAC | 22.8* | (11284) | AGC | 11.3 | (5594) |
| AUA | 12.9 | (6386) | ACA | 14.9 | (7391) | AAA | 26.9 | (13334) | AGA | 14.8* | (7337) |
| AUG | 22.7* | (11218) | ACG | 4.3 | (2147) | AAG | 35.9* | (17797) | AGG | 13.3 | (6574) |
| GUU | 26.1* | (12911) | GCU | 26.7* | (13201) | GAU | 32.4* | (16040) | GGU | 20.9 | (10353) |
| GUC | 11.9 | (5894) | GCC | 16.2 | (8026) | GAC | 20.4 | (10097) | GGC | 13.4 | (6650) |
| GUA | 7.7 | (3803) | GCA | 21.4 | (10577) | GAA | 33.2* | (16438) | GGA | 22.3* | (11022) |
| GUG | 21.4 | (10610) | GCG | 6.3 | (3123) | GAG | 33.2 | (16426) | GGG | 13.0 | (6431) |

Sequences of the present invention can also differ from the corresponding wildtype sequences (preferably, sequences of sub-group c) can also differ from the sequences of sub-groups a) and b)) by coding for a protein mutated by one or more acceptable point mutations. For example, the following amino acid substitutions (indicated by an asterisk) are considered acceptable point mutations according to the present invention:

| | A | R | N | D | C | Q | E | G | H | I | L | K | M | F | P | S | T | W | Y |
|---|---|---|---|---|---|---|---|---|---|---|---|---|---|---|---|---|---|---|---|
| A | | | | | | | | | | | | | | | | | | | |
| R | — | | | | | | | | | | | | | | | | | | |
| N | — | — | | | | | | | | | | | | | | | | | |
| D | — | — | * | | | | | | | | | | | | | | | | |
| C | — | — | — | — | | | | | | | | | | | | | | | |
| Q | — | * | * | * | — | | | | | | | | | | | | | | |
| E | — | — | * | * | — | * | | | | | | | | | | | | | |
| G | * | — | — | * | — | — | — | | | | | | | | | | | | |
| H | — | * | * | * | — | * | * | — | | | | | | | | | | | |
| I | — | — | — | — | — | — | — | — | — | | | | | | | | | | |
| L | — | — | — | — | — | — | — | — | — | * | | | | | | | | | |
| K | — | * | * | — | — | * | — | — | — | — | — | | | | | | | | |
| M | — | — | — | — | — | — | — | — | — | * | * | — | | | | | | | |
| F | — | — | — | — | — | — | — | — | — | * | * | — | — | | | | | | |
| P | * | — | — | — | — | — | — | — | — | — | — | — | — | — | | | | | |
| S | * | — | * | — | — | — | — | * | — | — | — | — | — | — | * | | | | |
| T | * | — | — | — | — | — | — | — | — | — | — | — | — | — | — | * | | | |
| W | — | * | — | — | — | — | — | — | — | — | — | — | — | — | — | — | — | | |
| Y | — | — | — | — | — | — | — | — | — | — | — | — | — | * | — | — | — | — | |
| V | — | — | — | — | — | — | — | — | — | * | * | — | * | — | — | — | — | — | — |

Preferably, the degree of identity is even higher, e.g. 48%, 58%, 68%, 74%, 78%, 84%, 88%, 90%, 94%, 95%, 96%, 97%, 98% or 99%. Good protection against infection by fungal pathogens can be achieved when the nucleic acid codes for a protein the amino acid of which is any of the amino acid sequences SEQ ID NO: 5, 6, 36, 34, 8, 51, 52, 48, 54, 26, 42, 30, 24, 56, 2, 22, 32, 28, 10, 58, 18, 20, 38, 14, 15, 16, 40, 44, 46 or 60.

According to the invention, identity of amino acid sequences and nucleic acid sequences, respectively, is determined using a global alignment algorithm, such as the Needleman Wunsch algorithm in the program GAP (GCG Wisconsin Package, Accelrys), preferably with default parameters and preferably with sequences of mature proteins (i.e. without taking into account secretion signals or transit peptides).

The nucleic acids advantageously are expressed in the plant cell of the present invention. The term "expression" or "gene expression" means the transcription of a specific gene or specific genes or specific genetic construct, particularly of any of the sequences of SEQ ID NO: 3, 4, 35, 33, 7, 49, 50, 47, 53, 25, 41, 29, 23, 55, 1, 21, 31, 27, 9, 57, 17, 19, 37, 11, 12, 13, 39, 43, 45 or 59. The term "expression" or "gene expression" in particular means the transcription of a gene or genes or genetic construct into structural RNA (rRNA, tRNA) or mRNA with or without subsequent translation of the latter into a protein. The process includes transcription of DNA and processing of the resulting mRNA product. The term "increased expression" or "overexpression" as used herein means any form of expression that is additional to the original wild-type expression level. For the purposes of this invention, the original wild-type expression level might also be zero, i.e. absence of expression or immeasurable expression.

To allow for expression of the nucleic acid of the present invention, the nucleic acid preferably is under the control of a transcription modifying element.

The invention correspondingly provides a plant cell comprising, as a heterologous polypeptide, a polypeptide selected from the group consisting of a) polypeptides having any of the amino acid sequences SEQ ID NO: 5, 6, 36, 34, 8, 51, 52, 48, 54, 26, 42, 30, 24, 56, 2, 22, 32, 28, 10, 58, 18, 20, 38, 14, 15, 16, 40, 44, 46 or 60, and b) polypeptides having an amino acid sequence identity of at least 40% to any of the amino acid sequences SEQ ID NO: 5, 6, 36, 34, 8, 51, 52, 48, 54, 26, 42, 30, 24, 56, 2, 22, 32, 28, 10, 58, 18, 20, 38, 14, 15, 16, 40, 44, 46 or 60.

Again, a protein or polypeptide is considered heterologous if any of the following criteria apply:

a) The protein is not part of the proteome of the corresponding wild type plant, or b) the protein is not expressed in the corresponding wild type plant, or c) the protein expression in the plant cell according to the present invention is higher than compared to the corresponding wild type plant.

Preferably, the criteria a) and/or b) apply; most preferably criterium a) applies.

The polypeptides allow to confer, modify or increase resistance of the plant cell against infection by fungal pathogens, preferably against infections by a pathogen of the class Basidiomycota, preferably of order Uredinales, more preferably of family Phakopsoraceae, even more preferably against soybean rust, even more preferably of genus *Phacopsora*, most preferably of species *Phakopsora pachyrhizi* (Sydow) and/or *Phakopsora meibomiae* (Arthur).

As described above for nucleic acids, the amino acid sequence of the polypeptide in the plant cell of the present invention may differ from the amino acid given for sub-group a). That is to say, the plant cell of the present invention can according to sub-group b) comprise a polypeptide having an amino acid sequence identity of at least 40% to any of the amino acid sequences SEQ ID NO: 5, 6, 36, 34, 8, 51, 52, 48, 54, 26, 42, 30, 24, 56, 2, 22, 32, 28, 10, 58, 18, 20, 38, 14, 15, 16, 40, 44, 46 or 60. Also as described above, the amino acid sequence of the polypeptide may differ from any of the amino acid sequences SEQ ID NO: 5, 6, 36, 34, 8, 51, 52, 48, 54, 26, 42, 30, 24, 56, 2, 22, 32, 28, 10, 58, 18, 20, 38, 14, 15, 16, 40, 44, 46 or 60 by one or more acceptable point mutations.

Preferably, the degree of identity is higher than 40%, e.g. 48%, 58%, 68%, 74%, 78%, 84%, 88%, 90%, 94%, 95%, 96%, 97%, 98% or 99%.

The invention also provides a vector, preferably an expression vector, comprising a nucleic acid selected from the group consisting of a) nucleic acids comprising any of the nucleic acid sequences SEQ ID NO: 3, 4, 35, 33, 7, 49, 50, 47, 53, 25, 41, 29, 23, 55, 1, 21, 31, 27, 9, 57, 17, 19, 37, 11, 12, 13, 39, 43, 45 or 59, b) nucleic acids coding for a polypeptide comprising any of the amino acid sequences SEQ ID NO: 5, 6, 36, 34, 8, 51, 52, 48, 54, 26, 42, 30, 24, 56, 2, 22, 32, 28, 10, 58, 18, 20, 38, 14, 15, 16, 40, 44, 46 or 60, and c) nucleic acids coding for a polypeptide having an amino acid sequence identity of at least 40% to any of the amino acid sequences SEQ ID NO: 5, 6, 36, 34, 8, 51, 52, 48, 54, 26, 42, 30, 24, 56, 2, 22, 32, 28, 10, 58, 18, 20, 38, 14, 15, 16, 40, 44, 46 or 60.

Such vectors allow to transfer easily the nucleic acid into a plant of interest. Useful methods of plant transformations are known to the skilled person, e.g. transformation by *Agrobacterium tumefaciens.*

The term "introduction" or "transformation" as referred to herein encompasses the transfer of an exogenous polynucleotide into a host cell, irrespective of the method used for transfer. Plant tissue capable of subsequent clonal propagation, whether by organogenesis or embryogenesis, may be transformed with a genetic construct of the present invention and a whole plant regenerated there from. The particular tissue chosen will vary depending on the clonal propagation systems available for, and best suited to, the particular species being transformed. Exemplary tissue targets include leaf disks, pollen, embryos, cotyledons, by pocotyls, megagametophytes, callus tissue, existing meristematic tissue (e.g., apical meristem, axillary buds, and root meristems), and induced meristem tissue (e.g., cotyledon meristem and hypocotyl meristem). The polynucleotide may be transiently or stably introduced into a host cell and may be maintained non-integrated, for example, as a plasmid. Alternatively, it may be integrated into the host genome. The resulting transformed plant cell may then be used to regenerate a transformed plant in a manner known to persons skilled in the art.

The transfer of foreign genes into the genome of a plant is called transformation. Transformation of plant species is now a fairly routine technique. Advantageously, any of several transformation methods may be used to introduce the gene of interest into a suitable ancestor cell. The methods described for the transformation and regeneration of plants from plant tissues or plant cells may be utilized for transient or for stable transformation. Transformation methods include the use of liposomes, electroporation, chemicals that increase free DNA uptake, injection of the DNA directly into the plant, particle gun bombardment, transformation using viruses or pollen and microprojection. Methods may be selected from the calcium/polyethylene glycol method for protoplasts (Krens, F. A. et al., (1982) Nature 296, 72-74; Negrutiu I et al. (1987) Plant Mol Biol 8: 363-373); electroporation of protoplasts (Shillito R. D. et al. (1985) Bio/Technol 3, 1099-1102); microinjection into plant material (Crossway A et al., (1986) Mol. Gen Genet 202: 179-185); DNA or RNA-coated particle bombardment (Klein T M et al., (1987) Nature 327: 70) infection with (non-integrative) viruses and the like. Transgenic plants, including transgenic crop plants, are preferably produced via *Agrobacterium*-mediated transformation. An advantageous transformation method is the transformation in planta. To this end, it is possible, for example, to allow the agrobacteria to act on plant seeds or to inoculate the plant meristem with agrobacteria. It has proved particularly expedient in accordance with the invention to allow a suspension of transformed agrobacteria to act on the intact plant or at least on the flower primordia. The plant is subsequently grown on until the seeds of the treated plant are obtained (Clough and Bent, Plant J. (1998) 16, 735-743). Methods for *Agrobacterium*-mediated transformation of rice include well known methods for rice transformation, such as those described in any of the following: European patent application EP 1198985 A1, Aldemita and Hodges (Planta 199: 612-617, 1996); Chan et al. (Plant Mol Biol 22 (3): 491-506, 1993), Hiei et al. (Plant J 6 (2): 271-282, 1994), which disclosures are incorporated by reference herein as if fully set forth. In the case of corn transformation, the preferred method is as described in either Ishida et al. (Nat. Biotechnol 14(6): 745-50, 1996) or Frame et al. (Plant Physiol 129(1): 13-22, 2002), which disclosures are incorporated by reference herein as if fully set forth. Said methods are further described by way of example in B. Jenes et al., Techniques for Gene Transfer, in: Transgenic Plants, Vol. 1, Engineering and Utilization, eds. S. D. Kung and R. Wu, Academic Press (1993) 128-143 and in Potrykus Annu. Rev. Plant Physiol. Plant Molec. Biol. 42 (1991) 205-225). The nucleic acids or the construct to be expressed is preferably cloned into a vector, which is suitable for transforming *Agrobacterium tumefaciens*, for example pBin19 (Bevan et al., Nucl. Acids Res. 12 (1984) 8711). Agrobacteria transformed by such a vector can then be used in known manner for the transformation of plants, such as plants used as a model, like *Arabidopsis* (*Arabidopsis thaliana* is within the scope of the present invention not considered as a crop plant), or crop plants such as, by way of example, tobacco plants, for example by immersing bruised leaves or chopped leaves in an agrobacterial solution and then culturing them in suitable media. The transformation of plants by means of *Agrobacterium tumefaciens* is described, for example, by Höfgen and Willmitzer in Nucl. Acid Res. (1988) 16, 9877 or is known inter alia from F. F. White, Vectors for Gene Transfer in Higher Plants; in Transgenic Plants, Vol. 1, Engineering and Utilization, eds. S. D. Kung and R. Wu, Academic Press, 1993, pp. 15-38.

In addition to the transformation of somatic cells, which then have to be regenerated into intact plants, it is also possible to transform the cells of plant meristems and in particular those cells which develop into gametes. In this case, the transformed gametes follow the natural plant development, giving rise to transgenic plants. Thus, for example, seeds of *Arabidopsis* are treated with agrobacteria and seeds are obtained from the developing plants of which a certain proportion is transformed and thus transgenic [Feldman, K A and Marks M D (1987). Mol Gen Genet 208:1-9; Feldmann K (1992). In: C Koncz, N-H Chua and J Shell, eds, Methods in *Arabidopsis* Research. Word Scientific, Singapore, pp. 274-289]. Alternative methods are based on the repeated removal of the inflorescences and incubation of the excision site in the center of the rosette with transformed agrobacteria, whereby transformed seeds can likewise be obtained at a later point in time (Chang (1994). Plant J. 5: 551-558; Katavic (1994). Mol Gen Genet, 245: 363-370). However, an especially effective method is the vacuum infiltration method with its modifications such as the "floral dip" method. In the case of vacuum infiltration of *Arabidopsis*, intact plants under reduced pressure are treated with an agrobacterial suspension [Bechthold, N (1993). C R Acad Sci Paris Life Sci, 316: 1194-1199], while in the case of the “floral dip” method the developing floral tissue is incubated briefly with a surfactant-treated agrobacterial suspension [Clough, S J and Bent A F (1998) The Plant J. 16, 735-743]. A certain proportion of transgenic seeds are harvested in both cases, and these seeds can be distinguished from non-transgenic seeds by growing under the above-described selective conditions. In addition the stable transformation of plastids is of advantages because plastids are inherited maternally is most crops reducing or eliminating the risk of transgene flow through pollen. The transformation of the chloroplast genome is generally achieved by a process which has been schematically displayed in Klaus et al., 2004 [Nature Biotechnology 22 (2), 225-229]. Briefly the sequences to be transformed are cloned together with a selectable marker gene between flanking sequences homologous to the chloroplast genome. These homologous flanking sequences direct site specific integration into the plastome. Plastidal transformation has been described for many different plant species and an overview is given in Bock (2001) Transgenic plastids in basic research and plant biotechnology. J Mol Biol. 2001 Sep. 21; 312 (3):425-38 or Maliga, P (2003) Progress towards commercialization of plastid transformation technology. Trends Biotechnol. 21, 20-28. Further biotechnological progress has recently been reported in form of marker free plastid transformants, which can be produced by a transient co-integrated maker gene (Klaus et al., 2004, Nature Biotechnology 22(2), 225-229). The genetically modified plant cells can be regenerated via all methods with which the skilled worker is familiar. Suitable methods can be found in the abovementioned publications by S. D. Kung and R. Wu, Potrykus or Höfgen and Willmitzer.

With respect to soybean transformation, methods are known which are based on somatic embryogenesis: Embryos are induced from immature soybean cotyledons by placing the explant on high levels of 2,4-D (40 mg/L) and the embryogenic tissues are subsequently proliferated on induction medium (Finer (1988) Plant Cell Rep 7:238-241) or liquid suspension culture (Finer and Nagasawa (1988) Plant Cell Tissue Organ Cult 15:125-136).

Hinchee et al. describes the production of transgenic soybean plants via *Agrobacterium*-mediated transformation. The production of transgenic plants is based on a regeneration protocol in which shoot organogenesis is induced on cotyledons of soybeans (see Hinchee et al. (1988) Nature Biotechnology, 6:915-922).

Also known are methods based on *Agrobacterium*-mediated transformation of zygotic immature cotyledons (Parrott et al. (1989) Plant Cell Rep 7:615-617; Yan et al. (2000) Plant Cell Rep 19:1090-1097; Ko et al. (2003) Theor Appl Genet. 107:439-447). However, in Parrott et al. the three plants produced were chimeric, from a multicellular origin, and did not transmit the transgene to the next generation. Yan et al. (2000) Plant Cell Rep 19:1090-1097 reported a low transformation frequency of 0.03%. The plant produced transmitted the transgene into the next generation, presumably due to the continuous selection of transformed primary embryos for the production of secondary embryos thereby resulting in non-chimeric plants. Recently, Ko et al. (2003) Theor Appl Genet. 107:439-447 has reported the recovery of transgenic plants at 1.7% transformation frequencies, however, the method relies on using a partially disarmed (oncogenic) *Agrobacterium* strain, pKYRT, with a functional TR-DNA sequence in order to stimulate embryogenesis (Ko et al. (2004) Planta 218:536-541). These methods use the immature cotyledons as the target tissue with subsequent proliferation and selection on solid medium.

US2009/0049567 discloses *Agrobacterium*-mediated soybean transformation utilizing meristematic cells of primary or higher leaf nodes as target tissues and subsequent regeneration of the transformed cells into a whole plant.

Further beneficial transformation methods are described in European patent application EP11175038.6 and U.S. patent application 61/510,513, both filed on 22 Jul. 2011 and incorporated herein by reference in their entirety.

Generally after transformation, plant cells or cell groupings are selected for the presence of one or more markers which are encoded by plant-expressible genes co-transferred with the gene of interest, following which the transformed material is regenerated into a whole plant. To select transformed plants, the plant material obtained in the transformation is, as a rule, subjected to selective conditions so that transformed plants can be distinguished from untransformed plants. For example, the seeds obtained in the above-described manner can be planted and, after an initial growing period, subjected to a suitable selection by spraying. A further possibility consists in growing the seeds, if appropriate after sterilization, on agar plates using a suitable selection agent so that only the transformed seeds can grow into plants. Alternatively, the transformed plants are screened for the presence of a selectable marker such as the ones described above.

Following DNA transfer and regeneration, putatively transformed plants may also be evaluated, for instance using Southern analysis, for the presence of the gene of interest, copy number and/or genomic organisation. Alternatively or additionally, expression levels of the newly introduced DNA may be monitored using Northern and/or Western analysis, both techniques being well known to persons having ordinary skill in the art.

The generated transformed plants may be propagated by a variety of means, such as by clonal propagation or classical breeding techniques. For example, a first generation (or T1) transformed plant may be selfed and homozygous second-generation (or T2) transformants selected, and the T2 plants may then further be propagated through classical breeding techniques. The generated transformed organisms may take a variety of forms. For example, they may be chimeras of transformed cells and non-transformed cells; clonal transformants (e.g., all cells transformed to contain the expression cassette); grafts of transformed and untransformed tissues (e.g., in plants, a transformed rootstock grafted to an untransformed scion).

Also provided is a host cell comprising the vector, preferably the expression vector, of the present invention. Such host cell allows to reproduce or multiply the vector of the present invention, and/or to transform a plant or plant cell. Useful host cells according to the present invention preferably are *Escherichia coli* and *Agrobacterium tumefaciens*.

The plant cell according to the present invention preferably is a cell taxonomically belonging to a crop plant species. Particularly preferred are cells of dicotyledon plants, preferably of family Fabaceae, more preferably of tribe Phaseoleae, even more preferably of genus *Glycine*, e.g. *Glycine soja, Soja hispida, Soja max* and *Glycine max*, and most preferably of *Glycine max*. Such plants are agriculturally important and suffer, as described above, from fungal pathogen infections.

The invention also provides a plant comprising, consisting essentially of or consisting of one or more plant cells of the present invention. This way, resistance of the plant as a whole against infections by fungal pathogens, preferably against infections by a pathogen of the class Basidiomycota, preferably of order Uredinales, more preferably of family Phakopsoraceae, even more preferably against soybean rust, even more preferably of genus *Phacopsora*, most preferably of species *Phakopsora pachyrhizi* (Sydow) and/or *Phakopsora meibomiae* (Arthur), can be improved compared to the wild type. As indicated above, the plant preferably is a dicotyledon plant, preferably of the family Fabaceae, more preferably of the tribe Phaseoleae, even more preferably of the genus *Glycine*, e.g. *Glycine soja, Soja hispida, Soja max* and *Glycine max*, and most preferably of *Glycine max*.

The invention thus provides a plant, preferably a crop plant as described above, exhibiting increased or modified resistance as compared to a wild type plant against infections by a fungus of the class Basidiomycota, preferably of the order Uredinales, more preferably of the family Phakopsoraceae, even more preferably of the genus *Phacopsora*, most preferably of the species *Phakopsora pachyrhizi* and/or *Phakopsora meibomiae*, wherein said plant i) comprises, consists essentially of or consists of a plant cell as described above; and/or
ii) comprises a nucleic acid selected from the group consisting of
  a) nucleic acids comprising any of the nucleic acid sequences SEQ ID NO: 3, 4, 35, 33, 7, 49, 50, 47, 53, 25, 41, 29, 23, 55, 1, 21, 31, 27, 9, 57, 17, 19, 37, 11, 12, 13, 39, 43, 45 or 59,
  b) nucleic acids coding for a polypeptide comprising any of the amino acid sequences SEQ ID NO: 5, 6, 36, 34, 8, 51, 52, 48, 54, 26, 42, 30, 24, 56, 2, 22, 32, 28, 10, 58, 18, 20, 38, 14, 15, 16, 40, 44, 46 or 60, and
  c) nucleic acids coding for a polypeptide having an amino acid sequence identity of at least 40%, at least 50%, at least 60%, at least 65%, at least 70%, at least 75%, at least 80%, at least 85%, at least 90%, at least 95%, at least 98% or at least 99% to any of the amino acid sequences SEQ ID NO: 5, 6, 36, 34, 8, 51, 52, 48, 54, 26, 42, 30, 24, 56, 2, 22, 32, 28, 10, 58, 18, 20, 38, 14, 15, 16, 40, 44, 46 or 60; and/or
iii) comprises a polypeptide selected from the group consisting of
  a) polypeptides having any of the amino acid sequences SEQ ID NO: 5, 6, 36, 34, 8, 51, 52, 48, 54, 26, 42, 30, 24, 56, 2, 22, 32, 28, 10, 58, 18, 20, 38, 14, 15, 16, 40, 44, 46 or 60, and
  b) polypeptides having an amino acid sequence identity of at least 40%, at least 50%, at least 60%, at least 65%, at least 70%, at least 75%, at least 80%, at least 85%, at least 90%, at least 95%, at least 98% or at least 99% to any of the amino acid sequences SEQ ID NO: 5, 6, 36, 34, 8, 51, 52, 48, 54, 26, 42, 30, 24, 56, 2, 22, 32, 28, 10, 58, 18, 20, 38, 14, 15, 16, 40, 44, 46 or 60,
  and wherein said polypeptide is heterologous to said plant.

As described herein, the nucleic acid(s) can be constitutively or temporarily expressed to produce the polypeptide(s) in the plant or plant cells. Where the nucleic acid(s) is/are constitutively expressed the respective plant or plant cells permanently comprises a level of the corresponding polypeptide and is thus exhibits permanently increased or modified resistance against infection by the pathogen. However, expression of the nucleic acid or nucleic acids can also be regulated such that expression is induced or repressed in predefined conditions. For example, the nucleic acid(s) can be inducibly expressed after application of an inductor to the plant or plant cells. Such inductor can be an artificial agent like IPTG, or can be a constituent of the infecting fungus. This way, production of the corresponding polypeptide or polypeptides can be started or increased in the plant or plant cell in the imminent danger of fungal infection, thereby saving resources when there is no imminent danger of infection. Also, expression can be limited to defined growth stages or organs of the plant, further saving resources of the plant.

The invention also provides a method for creating a plant, preferably a crop plant, particularly preferably a dicotyledon plant, preferably of the family Fabaceae, more preferably of the tribe Phaseoleae, even more preferably of the genus *Glycine*, e.g. *Glycine soja, Soja hispida, Soja max* and *Glycine max*, and most preferably of *Glycine max*, exhibiting increased or modified resistance as compared to a wild type plant against infections by a fungus of the class Basidiomycota, preferably of the order Uredinales, more preferably of the family Phakopsoraceae, even more preferably of the genus *Phacopsora*, most preferably of the species *Phakopsora pachyrhizi* and/or *Phakopsora meibomiae*, wherein the method comprises the steps of i) introducing a nucleic acid selected from the group consisting of
  a) a nucleic acid comprising any of the nucleic acid sequences SEQ ID NO: 3, 4, 35, 33, 7, 49, 50, 47, 53, 25, 41, 29, 23, 55, 1, 21, 31, 27, 9, 57, 17, 19, 37, 11, 12, 13, 39, 43, 45 or 59,
  b) a nucleic acid coding for a polypeptide comprising any of the amino acid sequences SEQ ID NO: 5, 6, 36, 34, 8, 51, 52, 48, 54, 26, 42, 30, 24, 56, 2, 22, 32, 28, 10, 58, 18, 20, 38, 14, 15, 16, 40, 44, 46 or 60, and
  c) a nucleic acid coding for a polypeptide having an amino acid sequence identity of at least 40%, at least 50%, at least 60%, at least 65%, at least 70%, at least 75%, at least 80%, at least 85%, at least 90%, at least 95%, at least 98% or at least 99% to any of the amino acid sequences SEQ ID NO: 5, 6, 36, 34, 8, 51, 52, 48, 54, 26, 42, 30, 24, 56, 2, 22, 32, 28, 10, 58, 18, 20, 38, 14, 15, 16, 40, 44, 46 or 60 into a plant cell, and
ii) growing a plant from said plant cell.

The method facilitates the production of plants having modified or increased resistance against infection by the above mentioned pathogen.

The invention also provides a method for creating a plant exhibiting increased or modified resistance as compared to a wild type plant against infections by a fungus of the class Basidiomycota, preferably of order Uredinales, more preferably of family Phakopsoraceae, even more preferably of genus *Phacopsora*, most preferably of species *Phakopsora pachyrhizi* and/or *Phakopsora meibomiae*, wherein the method comprises the step of reproducing a plant obtainable or obtained by the method as described above. Reproduction can be by means of seed generation or by artificial reproduction, e.g. using callus cultures.

Thus, the invention also provides a seed of a plant of the present invention. Such seeds beneficially allow to grow plants e.g. on a field having increased or modified resistance as compared to a wild type plant against infections by a fungus of the class Basidiomycota, preferably of order Uredinales, more preferably of family Phakopsoraceae, even more preferably of genus *Phacopsora*, most preferably of species *Phakopsora pachyrhizi* and/or *Phakopsora meibomiae*. Also corresponding to the above description, the seed preferably is a seed of a preferably a crop plant, particularly preferably a dicotyledon plant, preferably of family Fabaceae, more preferably of tribe Phaseoleae, even more preferably of genus *Glycine*, e.g. *Glycine soja, Soja* hispida, *Soja max* and *Glycine max*, and most preferably of *Glycine max*.

The invention also provides a method of conferring, increasing or modifying, in a plant, resistance as compared to a wild type plant against infections by a fungus of the class Basidiomycota, preferably of the order Uredinales, more preferably of the family Phakopsoraceae, even more preferably of the genus *Phacopsora*, most preferably of the species *Phakopsora pachyrhizi* and/or *Phakopsora meibomiae*, wherein the method comprises the step of i) inducing or increasing expression of a polypeptide selected from the group consisting of
  a) polypeptides having any of the amino acid sequences SEQ ID NO: 5, 6, 36, 34, 8, 51, 52, 48, 54, 26, 42, 30, 24, 56, 2, 22, 32, 28, 10, 58, 18, 20, 38, 14, 15, 16, 40, 44, 46 or 60, and
  b) polypeptides having an amino acid sequence identity of at least 40%, at least 50%, at least 60%, at least 65%, at least 70%, at least 75%, at least 80%, at least 85%, at least 90%, at least 95%, at least 98% or at least 99% to any of the amino acid sequences SEQ ID NO: 5, 6, 36, 34, 8, 51, 52, 48, 54, 26, 42, 30, 24, 56, 2, 22, 32, 28, 10, 58, 18, 20, 38, 14, 15, 16, 40, 44, 46 or 60, and
  c) homologs of the polypeptides having any of the amino acid sequences SEQ ID NO: 5, 6, 36, 34, 8, 51, 52, 48, 54, 26, 42, 30, 24, 56, 2, 22, 32, 28, 10, 58, 18, 20, 38, 14, 15, 16, 40, 44, 46 or 60.

By inducing the expression of the polypeptide, preferably by inducing the expression using a nucleic acid as described above, production of the corresponding polypeptide or polypeptides can be started or increased in the plant or plant cell in the imminent danger of fungal infection, thereby saving resources when there is no imminent danger of infection. Also, expression can be limited to defined growth stages or organs of the plant, further saving resources of the plant.

In view of the present invention, "induction" or "inducing" is understood to comprise both the increase of a previously lower level of expression, and the commencement of previously not detectable expression.

In the above method, expression of homologs of the polypeptides having any of the amino acid sequences SEQ ID NO: 5, 6, 36, 34, 8, 51, 52, 48, 54, 26, 42, 30, 24, 56, 2, 22, 32, 28, 10, 58, 18, 20, 38, 14, 15, 16, 40, 44, 46 or 60 can be induced. A polypeptide is considered to be a homolog if its pattern of expression resembles that of one or more of the aforementioned polypeptides. Such expression pattern can be determined as described in the examples. Also, homologs can be found in databases, e.g. in the HomoloGene database maintained at the US National Center for Biotechnology Information (NCBI). The term "homolog" therefor includes orthologs and paralogs.

Harvestable parts of the transgenic plant according to the present invention are part of the invention. Preferably, the harvestable parts comprise the CL nucleic acid or CL protein. The harvestable parts may be seeds, roots, leaves and/or flowers comprising the CL nucleic acid or CL protein or parts thereof. Preferred parts of soy plants are soy beans comprising the CL nucleic acid or CL protein.

Products derived from a transgenic plant according to the present invention, parts thereof or harvestable parts thereof are part of the invention. A preferred product is meal or oil, preferably, soybean meal or soybean oil. Preferably, the soybean meal and/or oil comprises the CL nucleic acid or CL protein.

One embodiment is a method for the production of a product comprises a) growing the plants of the invention or obtainable by the methods of the invention and
b) producing said product from or by the plants of the invention and/or parts, e.g. seeds, of these plants.

In a further embodiment the method comprises the steps a) growing the plants of the invention, b) removing the harvestable parts as defined above from the plants and c) producing said product from or by the harvestable parts of the invention.

The product may be produced at the site where the plant has been grown, the plants and/or parts thereof may be removed from the site where the plants have been grown to produce the product. Typically, the plant is grown, the desired harvestable parts are removed from the plant, if feasible in repeated cycles, and the product made from the harvestable parts of the plant. The step of growing the plant may be performed only once each time the methods of the invention is performed, while allowing repeated times the steps of product production e.g. by repeated removal of harvestable parts of the plants of the invention and if necessary further processing of these parts to arrive at the product. It is also possible that the step of growing the plants of the invention is repeated and plants or harvestable parts are stored until the production of the product is then performed once for the accumulated plants or plant parts. Also, the steps of growing the plants and producing the product may be performed with an overlap in time, even simultaneously to a large extend or sequentially. Generally the plants are grown for some time before the product is produced.

In one embodiment the products produced by said methods of the invention are plant products such as, but not limited to, a foodstuff, feedstuff, a food supplement, feed supplement, fiber, cosmetic and/or pharmaceutical. Foodstuffs are regarded as compositions used for nutrition and/or for supplementing nutrition. Animal feedstuffs and animal feed supplements, in particular, are regarded as foodstuffs.

In another embodiment the inventive methods for the production are used to make agricultural products such as, but not limited to, plant extracts, proteins, amino acids, carbohydrates, fats, oils, polymers, vitamins, and the like.

It is possible that a plant product consists of one or more agricultural products to a large extent.

The transgenic plants of the invention may be crossed with similar transgenic plants or with transgenic plants lacking the nucleic acids of the invention or with non-transgenic plants, using known methods of plant breeding, to prepare seeds. Further, the transgenic plant cells or plants of the present invention may comprise, and/or be crossed to another transgenic plant that comprises one or more exogenous nucleic acids, thus creating a "stack" of transgenes in the plant and/or its progeny. The seed is then planted to obtain a crossed fertile transgenic plant comprising the CL nucleic acid. The crossed fertile transgenic plant may have the particular expression cassette inherited through a female parent or through a male parent. The second plant may be an inbred plant. The crossed fertile transgenic may be a hybrid. Also included within the present invention are seeds of any of these crossed fertile transgenic plants. The seeds of this invention can be harvested from fertile transgenic plants and be used to grow progeny generations of transformed plants of this invention including hybrid plant lines comprising the exogenous nucleic acid.

Thus, one embodiment of the present invention is a method for breeding a fungal resistant plant comprising the steps of (a) crossing a transgenic plant described herein or a plant obtainable by a method described herein with a second plant;

(b) obtaining a seed or seeds resulting from the crossing step described in (a);
(c) planting said seed or seeds and growing the seed or seeds to plants; and
(d) selecting from said plants the plants expressing a CL protein, preferably encoded by
 (i) a heterologous nucleic acid having at least 40% identity with SEQ ID NO: 3, 4, 35, 33, 7, 49, 50, 47, 53, 25, 41, 29, 23, 55, 1, 21, 31, 27, 9, 57, 17, 19, 37, 11, 12, 13, 39, 43, 45 or 59, a functional fragment thereof, an orthologue or a paralogue thereof, or a splice variant thereof;
 (ii) a heterologous nucleic acid encoding a protein having at least 40% identity with SEQ ID NO: 5, 6, 36, 34, 8, 51, 52, 48, 54, 26, 42, 30, 24, 56, 2, 22, 32, 28, 10, 58, 18, 20, 38, 14, 15, 16, 40, 44, 46 or 60, or a functional fragment thereof, an orthologue or a paralogue thereof; preferably the encoded protein confers enhanced fungal resistance relative to control plants;
 (iii) a heterologous nucleic acid capable of hybridizing under stringent conditions with a complementary sequence of any of the nucleic acids according to (i) or (ii); preferably encoding a CL protein; preferably wherein the nucleic acid molecule codes for a polypeptide which has essentially identical properties to the polypeptide described in SEQ ID NO: 5, 6, 36, 34, 8, 51, 52, 48, 54, 26, 42, 30, 24, 56, 2, 22, 32, 28, 10, 58, 18, 20, 38, 14, 15, 16, 40, 44, 46 or 60; preferably the encoded protein confers enhanced fungal resistance relative to control plants; and/or by
 (iv) a heterologous nucleic acid encoding the same CL protein as any of the nucleic acids of (i) to (iii) above, but differing from the nucleic acids of (i) to (iii) above due to the degeneracy of the genetic code.

Another preferred embodiment is a method for plant improvement comprising
(a) obtaining a transgenic plant by any of the methods of the present invention;
(b) combining within one plant cell the genetic material of at least one plant cell of the plant of (a) with the genetic material of at least one cell differing in one or more gene from the plant cells of the plants of (a) or crossing the transgenic plant of (a) with a second plant;
(c) obtaining seed from at least one plant generated from the one plant cell of (b) or the plant of the cross of step (b);
(d) planting said seeds and growing the seeds to plants; and
(e) selecting from said plants, plants expressing the nucleic acid encoding the CL protein; and optionally
(f) producing propagation material from the plants expressing the nucleic acid encoding the CL protein.

The transgenic plants may be selected by known methods as described above (e.g., by screening for the presence of one or more markers which are encoded by plant-expressible genes co-transferred with the CL gene or screening for the CL nucleic acid itself).

The invention is hereinafter further described using examples, tables and figures, particularly detailing preferred embodiments of the present invention. However, neither of these is to be construed as limiting the scope of the claims.

EXAMPLES

The following examples are not intended to limit the scope of the claims to the invention, but are rather intended to be exemplary of certain embodiments. Any variations in the exemplified methods that occur to the skilled artisan are intended to fall within the scope of the present invention.

Example 1: General Methods

The chemical synthesis of oligonucleotides can be affected, for example, in the known fashion using the phosphoamidite method (Voet, Voet, 2nd Edition, Wiley Press New York, pages 896-897). The cloning steps carried out for the purposes of the present invention such as, for example, restriction cleavages, agarose gel electrophoresis, purification of DNA fragments, transfer of nucleic acids to nitrocellulose and nylon membranes, linking DNA fragments, transformation of *E. coli* cells, bacterial cultures, phage multiplication and sequence analysis of recombinant DNA, are carried out as described by Sambrook et al. Cold Spring Harbor Laboratory Press (1989), ISBN 0-87969-309-6. The sequencing of recombinant DNA molecules is carried out with an MWG-Licor laser fluorescence DNA sequencer following the method of Sanger (Sanger et al., Proc. Natl. Acad. Sci. USA 74, 5463 (1977)).

Example 2: Performing Microarray Analysis with *Arabidopsis thaliana* Plants Inoculated with Soybean Rust For RNA extraction frozen leaf material from four plants per genotype and treatment was pooled and ground in liquid nitrogen. RNA was extracted following a modified guanidinium thiocyanate-phenol protocol (Chomczynski and Sacchi, 1987) in combination with the Rneasy® Mini Kit (Qiagen). Thereto, 1 ml of RNA extraction reagent was added to 100 mg of homogenized plant material and the mixture was vortexed thoroughly. After an incubation of 5 min at RT, 200 μl of chloroform were added and the samples mixed again for at least 15 sec. After incubation for 3 more minutes the samples were centrifuged at −4° C. and 14,°000 rpm for 15 min in a tabletop centrifuge. Subsequently, 400 μl of the upper aqueous phase was transferred into a new microcentifuge tube and RNA was precipitated adding 200 μl ethanol (96%). From here, the Rneasy® Mini Kit (Qiagen) was followed starting from step 6 (Protocol: Purification of Total RNA from Plant Cells and Tissues and Filamentous Fungi). 10 to 15 μg of RNA from two independently performed experiments was sent to the IFG in Münster for hybridization with ATH1 gene chips. Raw data from microarray experiments was obtained from the IFG in Münster as Affymetrix cel files. All array cel files were compressed to zip files and uploaded to the webbased pipeline for microarray gene expression profile analysis, GEPAS (http://www.gepas.org). Raw data was subsequently normalized using following settings in parallel:
1. rma; constant, pmonly, medianpolish (log transformation integrated)
2. rma; quantiles, pmonly, medianpolish (log transformation integrated)
3. rma; invariant set, pmonly, medianpolish (log transformation integrated)

Example 3: Bioinformatical Selection of CL Genes

Gene expression data was subsequently analyzed using the Microsoft Excel© macro FiRe (Garcion et al., 2006). Using this tool gene expression data was analyzed for genes that were induced at least 1.2 fold in *P. pachyrhizi*-treated pen2-1 mutants but not in *P. pachyrhizi*-infected Col-0 or pen2 pad4 sag101 plants and which were at the same time equally expressed among all mock-treated genotypes. This setting was applied for expression data of all biological replicates and normalization procedures. Then, consistent genes between two biological replicates of each normalization procedure where selected by merging respective gene lists. After that genes consistent among all three normalization procedures were identified, yielding a set of 25 candidate genes.

Example 4: Verification of Expression Pattern of CL-Genes

To verify the gene induction of these 25 candidate genes in *P. pachyrhizi*-infected pen2-1 mutants with an alternative method, RNA was extracted from three independent experiments from pen2-1 mutants at two days after infection with *P. pachyrhizi* or mock inoculation following a modified guanidinium thiocyanate-phenol protocol (Chomczynski and Sacchi, 1987). 1 ml of RNA extraction reagent was added to 100 mg of homogenized plant material and the mixture was vortexed thoroughly. After an incubation of 5 minutes at RT, 200 μl of chloroform were added and the samples mixed again for at least 15 sec. After incubation for 3 more minutes the samples were centrifuged at −4° C. and 14,000 rpm for 15 min in a tabletop centrifuge. Subsequently, the upper aqueous phase was transferred into a new microcentifuge tube. To precipitate the RNA 500 μl of isopropanol were added, the samples shortly mixed on a Vortex shaker, incubated at RT for 10 min, and centrifuged at −4° C. and 14,000 rpm for 10 min. The resulting pellet was washed with 70% (v/v) ethanol and centrifuged again for 5 minutes. Afterwards the supernatant was removed, the pellet dried for 10 min and then 30 μl of DEPC-treated water were added. RNA was dissolved by heating the samples for 10 min at 60° C. and pipetting up and down. RNA was stored at −20° C.

RNA samples were transcribed into cDNA. Before cDNA synthesis, a 1 μg of RNA of each sample was subjected to DNAse 1 treatment of the RNA samples was performed according to manufactures instructions (Fermentas). For synthesis of cDNA 1 μl random primer (50 μM stock solution, Invitrogen) and 1 μl DEPC-treated water were added to each sample, followed by an incubation at 70° C. for 5 min, to allow primer annealing. Afterwards, 4 μl 5×M-MuLV buffer (Fermentas), 2 μl dNTPs (10 mM stock solution), 1 μL RevertAid™ M-MuLV Reverse Transcriptase (Fermentas) and 1 μl DEPC-treated water were added to each sample. Reverse transcription of RNA was initiated by incubation of the samples at 37° C. for 60 min. With a last incubation step at 70° C. for 10 min the enzyme was inactivated. cDNA was stored at −20° C.

Differential gene expression among *P. pachyrhizi*-infected and mock treated pen2-1 mutants was subsequently analyzed by RT-qPCR using gene-specific primers for each candidate gene. To perform RT-qPCR a master mix of 5 μl Platinum® SYBR® Green qPCR Super-Mix-UDG with ROX (Invitrogen), 7 μl H20, and 0.15 μl of each primer (end concentration 150 nM) per reaction was prepared and pipetted in 96-well plates (Sarstedt). Before use cDNA was diluted 1:10. 2 μl cDNA were added to each well and for each reaction three technical replicates were done. The PCR reaction was performed in 7300 Real Time PCR Detection System (Applied Biosystems) under the following conditions: 2 min (50° C.), 10 min (95° C.), 40 cycles [15 s (95° C.), 1 min (60° C.)]. The AbiPrism 7300 SDS System software was used to analyze the data. According to the mathematic model of Livak and Schmittgen (2001) every gene specific transcript level was normalized to the respective housekeeping gene using the 2-ΔΔCt method. ACTIN2 was used as the supposedly constitutively expressed reference gene for *Arabidopsis*. Genes were defined to be silenced at a relative expression level of 50% or below in comparison to the non-transformed control.

Figure 1C:
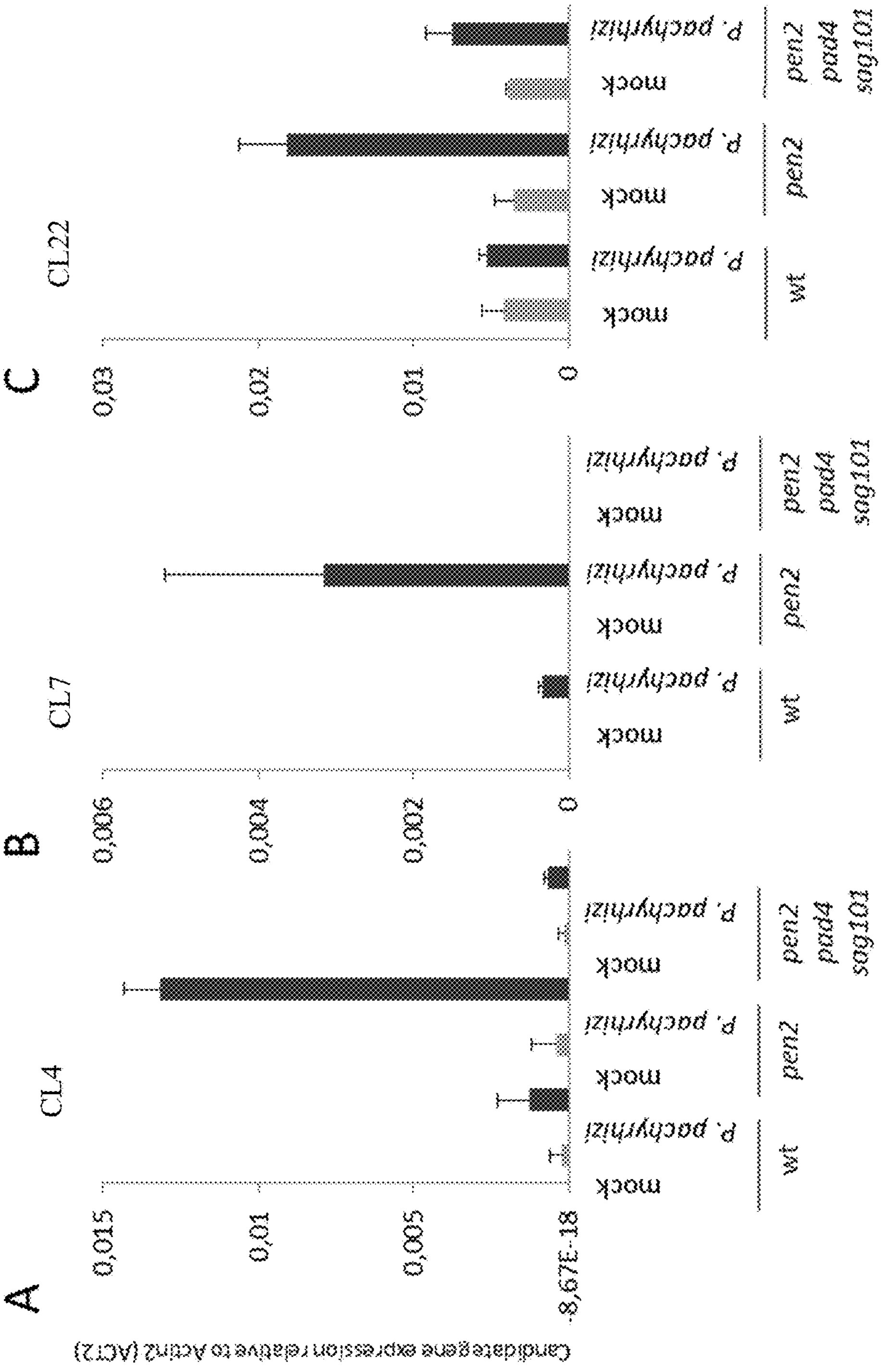

The induction of gene expression of all CL genes in *Arabidopsis* pen2 mutant after inoculation with *Phakopsora pachyrhizi* in comparison to *Arabidopsis* wild-type Col-0 could be confirmed (FIG. 1*a*). In addition exemplary results for an in depth analysis for the CL genes CL4, CL7 and CL22 are given in FIG. 1*c*, showing that the CL genes are exclusively expressed during post-invasive resistance against soybean rust in *Arabidopsis* pen2 mutant (FIG. 1*c*).

By deeper anaylzing the CL7 gene family (germin-like proteins), a homolog of CL7, called GLP9, was discovered, which showed an expression pattern nearly identical to CL7 (FIG. 1*b*) and also confers, improves or modifies resistance against infections by fungal pathogens, as described herein.

Example 5: Evaluation of CL Gene Effect in *Arabidopsis*

Example 5.1: Cloning of CL-Silencing Constructs

Candidate genes were then tested for their contribution to *Arabidopsis*' nonhost resistance in pen2-1 against *P. pachyrhizi* by double stranded RNA silencing. Thereto, either parts of the candidate gene sequence or the full coding region was used in a silencing vector to mediate post-transcriptional gene silencing. If available, clones for *Arabidopsis* candidate genes were obtained from TAIR (www. *arabidopsis*.org) as either entry clones containing full length coding region (CL6, CL9, CL10, CL13, CL16, CL24, GLP9) or parts of it or as expression vectors containing artificial microRNA sequences specifically targeting the gene of interest (CL3, CL5, CL7, CL11, CL23). Entry clones were used in the LR reaction to clone the gene-specific insert into the destination vector pJawohl8 (B. Ülker, Genbank accession number AF408413.1). The destination vectors for gene silencing include two lambda integration sites, one in a sense and one in an antisense direction, to create a double-stranded hairpin RNA which will be recognized by the post-transcriptional gene silencing machinery and, therefore, mediate specific degradation of targeted mRNA. Expression clones were used for plant transformation (see below). For candidate genes without corresponding clones at TAIR, a fragment for silencing (full length or a fragment of the coding regions' 3' ends part) was amplified by PCR using primers which were designed using the Primer 3 program. The Gateway®-specific regions attb1 and attb2 were added at the primers' 5' ends for cloning with Gateway® technology (Invitrogen). Amplification was done using proofreading Phusion® High-Fidelity DNA Polymerase (Finnzymes). (Primer sequences are listed in Table 2). PCR products were cleaned using the QIAquick® PCR Purification Kit (Qiagen). Gateway® cloning was performed according to manufacturer's instructions using Gateway® BP Clonase® II enzyme mix and Gateway® LR Clonase® II enzyme mix (both Invitrogen). As donor vector, pDONR207 (Invitrogen) was used and as destination vector, the sequences were cloned into the binary silencing vector pJawohl8.

Entry and expression vectors were amplified in *E. coli* DH5α and isolated from bacteria using the Zyppy™ Plasmid Miniprep kit (Zymo Research).

Example 5.2: *Arabidopsis* Transformation

For *Arabidopsis* transformation, the expression vectors were transformed into *Agrobacterium tumefaciens* strain GV3101 and *Arabidopsis* Col-0 and pen2-1 plants (Lipka et al., 2005) were dipped into *Agrobacterium* suspension following a modified protocol (Bechtold and Pelletier, 1998) of Clough and Bent (1998). Only those constructs obtained from TAIR harbouring artificial miRNA ((CL3, CL5, CL7, CL11, CL23; see Example 5.1)) were co-transformed with Agrobacteria containing pSoup (Hellens et al., 2000). Dipped plants were allowed to set seed. Seeds produced by dipped plants were sown on soil drenched with 1 ml/L (v/v) Basta® (Bayer CropScience) for selection of plants with transformation events. The pJawohl8-based vectors carry the coding sequence of a phosphinotricin-acetyltransferase which provides resistance against the glufosinate herbicide Basta®. Healthy-looking seedlings were transplanted into fresh soil at approximately two weeks after germination. These plants were tested for positive silencing using RT-qPCR. Thereto, five-week-old plants were inoculated with *P. pachyrhizi* together with pen2-1 control plants as described above. Leaf material was harvested for each plant after 48 hpi for RNA extraction (one leaf per plant) and microscopy (two leaves per plant). Methods for RNA extraction following a modified guanidinium thiocyanate-phenol protocol (Chomczynski and Sacchi, 1987) and microscopy are described above.

Example 6: Resistance Evaluation in CL-Gene Silenced *Arabidopsis thaliana*

Successfully silenced plants were analyzed microscopically after trypan blue staining to determine if the interaction of the plant with *P. pachyrhizi* has changed in silenced plants compared to untransformed control plants. Thereto, *Arabidopsis* leaves were incubated in trypan blue solution (10% (v/v) lactic acid, 10% (v/v) glycerol, 10% (v/v) deionized $H_2O$, 70% (v/v) Ethanol, 0.025% (w/v) trypan blue) and incubated for 1 min at 80° C. to stain fungal structures and collapsed plant cells (Keogh et al., 1980). After incubation for 10 min at RT the staining solution was replaced by chloral hydrate (2.5 g/ml (w/v)) destaining solution. Leaves were kept in destaining solution for at least two days, before they were mounted on object slides in 50% (v/v) glycerol. For microscopic analysis a Nikon Eclipse50i and a Leica DMRBE microscope were used. 100 interaction sites were examined on each leaf. Statistical evaluation of microscopic results was done with help of the software R (version 2.10.1).

Successful silencing of the resistance genes CI genes either by RNAi or by miRNA should lead to an increased susceptibility of *Arabidopsis* to soybean rust. It could be shown that the reduction of expression by RNAi (knock down) of CL4, CL7, CL15, CL16, CL22 and CL23 lead to an increased susceptibility in *Arabidopsis* pen2, indicating for an involvement of these genes in resistance against soybean rust (see FIG. 11). Additionally the inventors could show that the silencing of GLP9 leads to an increased haustoria formation in *Arabidopsis* pen2 plants from ~13% haustoria in *Arabidopsis* pen2 to ~31% in events silenced in GLP9. It is assumed that also the silencing of other CL genes will increase susceptibility in *Arabidopsis.*

Example 7: Cloning of Overexpression Vector Constructs

The cDNAs of all genes mentioned in this application were generated by DNA synthesis (Geneart, Regensburg, Germany).

The CL7, CL20, CL21 and CL24 cDNAs were synthesized in a way that a PacI restriction site is located in front of the start-ATG and a AscI restriction site downstream of the stop-codon. The synthesized cDNA were digested using the restriction enzymes PacI and AscI (NEB Biolabs) and ligated in a PacI/AscI digested Gateway pENTRY vector (Invitrogen, Life Technologies, Carlsbad, Calif., USA) in a way that the full-length fragment is located in sense direction between the parsley ubiquitine promoter (PcUbi) and a *Solanum tuberosum* CAT-pA terminator.

To obtain the binary plant transformation vector, a triple LR reaction (Gateway system, (Invitrogen, Life Technologies, Carlsbad, Calif., USA) was performed according to manufacturers' protocol by using an empty pENTRY-A vector, the above described pENTRY-B vector containing the cDNA and an empty pENTRY-C vector. As target a binary pDEST vector was used which is composed of: (1) a Spectinomycin/Streptomycin resistance cassette for bacterial selection (2) a pVS1 origin for replication in Agrobacteria (3) a pBR322 origin of replication for stable maintenance in *E. coli* and (4) between the right and left border an AHAS selection under control of a PcUbi-promoter. The recombination reaction was transformed into *E. coli* (DH5alpha), mini-prepped and screened by specific restriction digestions. A positive clone from each vector construct was sequenced and submitted soy transformation.

The other CL cDNAs (including GLP9) are synthesized in a way that a PacI restriction site is located in front of the start-ATG and a AscI restriction site downstream of the stop-codon. The synthesized cDNA are digested using the restriction enzymes PacI and AscI (NEB Biolabs) and ligated in a PacI/AscI digested Gateway pENTRY vector (Invitrogen, Life Technologies, Carlsbad, Calif., USA) in a way that the full-length fragment is located in sense direction between the parsley ubiquitine promoter (PcUbi) and a *Solanum tuberosum* CAT-pA terminator.

To obtain the binary plant transformation vector, a triple LR reaction (Gateway system, (Invitrogen, Life Technologies, Carlsbad, Calif., USA) is performed according to manufacturers' protocol by using an empty pENTRY-A vector, the above described pENTRY-B vector containing the cDNA and an empty pENTRY-C vector. As target a binary pDEST vector is used which is composed of: (1) a Spectinomycin/Streptomycin resistance cassette for bacterial selection (2) a pVS1 origin for replication in Agrobacteria (3) a pBR322 origin of replication for stable maintenance in *E. coli* and (4) between the right and left border an AHAS selection under control of a PcUbi-promoter. The recombination reaction is transformed into *E. coli* (DH5alpha), mini-prepped and screened by specific restriction digestions. A positive clone from each vector construct is sequenced and submitted soy transformation.

Example 8: Soy Transformation

The expression vector constructs (see Example 7) were transformed into soy.

8.1 Sterilization and Germination of Soy Seeds

Virtually any seed of any soy variety can be employed in the method of the invention. A variety of soycultivar (including Jack, Williams 82, and Resnik) is appropriate for soy transformation. Soy seeds were sterilized in a chamber with a chlorine gas produced by adding 3.5 ml 12N HCl drop wise into 100 ml bleach (5.25% sodium hypochlorite) in a desiccator with a tightly fitting lid. After 24 to 48 hours in the chamber, seeds were removed and approximately 18 to 20 seeds were plated on solid GM medium with or without 5 μM 6-benzyl-aminopurine (BAP) in 100 mm Petri dishes. Seedlings without BAP are more elongated and roots develop, especially secondary and lateral root formation. BAP strengthens the seedling by forming a shorter and stockier seedling.

Seven-day-old seedlings grown in the light (>100 μEinstein/$m^2$s) at 25° C. were used for explant material for the three-explant types. At this time, the seed coat was split, and the epicotyl with the unifoliate leaves have grown to, at minimum, the length of the cotyledons. The epicotyl should be at least 0.5 cm to avoid the cotyledonary-node tissue (since soy cultivars and seed lots may vary in the developmental time a description of the germination stage is more accurate than a specific germination time).

For inoculation of entire seedlings (Method A, see example 3.3. and 3.3.2) or leaf explants (Method B, see example 3.3.3), the seedlings were then ready for transformation.

For method C (see example 3.3.4), the hypocotyl and one and a half or part of both cotyledons were removed from each seedling. The seedlings were then placed on propagation media for 2 to 4 weeks. The seedlings produce several branched shoots to obtain explants from. The majority of the explants originated from the plantlet growing from the apical bud. These explants were preferably used as target tissue.

8.2—Growth and Preparation of *Agrobacterium* Culture

*Agrobacterium* cultures were prepared by streaking *Agrobacterium* (e.g., *A. tumefaciens* or *A. rhizogenes*) carrying the desired binary vector (e.g. H. Klee. R. Horsch and S. Rogers 1987 *Agrobacterium*-Mediated Plant Transformation and its further Applications to Plant Biology; Annual Review of Plant Physiology Vol. 38: 467-486) onto solid YEP growth medium YEP media: 10 g yeast extract. 10 g Bacto Peptone, 5 g NaCl, adjust pH to 7.0, and bring final volume to 1 liter with H2O, for YEP agar plates add 20 g Agar, autoclave) and incubating at 25° C. until colonies appeared (about 2 days). Depending on the selectable marker genes present on the Ti or Ri plasmid, the binary vector, and the bacterial chromosomes, different selection compounds were be used for *A. tumefaciens* and rhizogenes selection in the YEP solid and liquid media. Various *Agrobacterium* strains can be used for the transformation method.

After approximately two days, a single colony (with a sterile toothpick) was picked and 50 ml of liquid YEP was inoculated with antibiotics and shaken at 175 rpm (25° C.) until an $OD_{600}$ between 0.8-1.0 is reached (approximately 2 d). Working glycerol stocks (15%) for transformation are prepared and one-ml of *Agrobacterium* stock aliquoted into 1.5 ml Eppendorf tubes then stored at −80° C.

The day before explant inoculation, 200 ml of YEP were inoculated with 5 μl to 3 ml of working *Agrobacterium* stock in a 500 ml Erlenmeyer flask. The flask was shaked overnight at 25° C. until the $OD_{600}$ was between 0.8 and 1.0. Before preparing the soyexplants, the Agrobacteria were pelleted by centrifugation for 10 min at 5,500×g at 20° C. The pellet was resuspended in liquid CCM to the desired density ($OD_{600}$ 0.5-0.8) and placed at room temperature at least 30 min before use.

8.3—Explant Preparation and Co-Cultivation (Inoculation)

8.3.1 Method A: Explant Preparation on the Day of Transformation.

Seedlings at this time had elongated epicotyls from at least 0.5 cm but generally between 0.5 and 2 cm. Elongated epicotyls up to 4 cm in length had been successfully employed. Explants were then prepared with: i) with or without some roots, ii) with a partial, one or both cotyledons, all preformed leaves were removed including apical meristem, and the node located at the first set of leaves was injured with several cuts using a sharp scalpel.

This cutting at the node not only induced *Agrobacterium* infection but also distributed the axillary meristem cells and damaged pre-formed shoots. After wounding and preparation, the explants were set aside in a Petri dish and subsequently co-cultivated with the liquid CCM/*Agrobacterium* mixture for 30 minutes. The explants were then removed from the liquid medium and plated on top of a sterile filter paper on 15×100 mm Petri plates with solid co-cultivation medium. The wounded target tissues were placed such that they are in direct contact with the medium.

8.3.2 Modified Method A: Epicotyl Explant Preparation

Soy epicotyl segments prepared from 4 to 8 d old seedlings were used as explants for regeneration and transformation. Seeds of soyacv L00106CN, 93-41131 and Jack were germinated in 1/10 MS salts or a similar composition medium with or without cytokinins for 4 to 8 d. Epicotyl explants were prepared by removing the cotyledonary node and stem node from the stem section. The epicotyl was cut into 2 to 5 segments. Especially preferred are segments attached to the primary or higher node comprising axillary meristematic tissue.

The explants were used for *Agrobacterium* infection. *Agrobacterium* AGL1 harboring a plasmid with the GUS marker gene and the AHAS, bar or dsdA selectable marker gene was cultured in LB medium with appropriate antibiotics overnight, harvested and resuspended in a inoculation medium with acetosyringone. Freshly prepared epicotyl segments were soaked in the *Agrobacterium* suspension for 30 to 60 min and then the explants were blotted dry on sterile filter papers. The inoculated explants were then cultured on a co-culture medium with L-cysteine and TTD and other chemicals such as acetosyringone for enhancing T-DNA delivery for 2 to 4 d. The infected epicotyl explants were then placed on a shoot induction medium with selection agents such as imazapyr (for AHAS gene), glufosinate (for bar gene), or D-serine (for dsdA gene). The regenerated shoots were subcultured on elongation medium with the selective agent.

For regeneration of transgenic plants the segments were then cultured on a medium with cytokinins such as BAP, TDZ and/or Kinetin for shoot induction. After 4 to 8 weeks, the cultured tissues were transferred to a medium with lower concentration of cytokinin for shoot elongation. Elongated shoots were transferred to a medium with auxin for rooting and plant development.

Multiple shoots were regenerated.

Many stable transformed sectors showing strong expression were recovered. Soy plants were regenerated from epicotyl explants. Efficient T-DNA delivery and stable transformed sectors were demonstrated.

8.3.3 Method B: Leaf Explants

For the preparation of the leaf explant the cotyledon was removed from the hypocotyl. The cotyledons were separated from one another and the epicotyl is removed. The primary leaves, which consist of the lamina, the petiole, and the stipules, were removed from the epicotyl by carefully cutting at the base of the stipules such that the axillary meristems were included on the explant. To wound the explant as well as to stimulate de novo shoot formation, any preformed shoots were removed and the area between the stipules was cut with a sharp scalpel 3 to 5 times.

The explants are either completely immersed or the wounded petiole end dipped into the *Agrobacterium* suspension immediately after explant preparation. After inoculation, the explants are blotted onto sterile filter paper to remove excess *Agrobacterium* culture and place explants with the wounded side in contact with a round 7 cm Whatman paper overlaying the solid CCM medium (see above). This filter paper prevents *A. tumefaciens* overgrowth on the soyexplants. Wrap five plates with Parafilm™ "M" (American National Can, Chicago, Ill., USA) and incubate for three to five days in the dark or light at 25° C.

8.3.4 Method C: Propagated Axillary Meristem

For the preparation of the propagated axillary meristem explant propagated 3-4 week-old plantlets were used. Axillary meristem explants can be pre-pared from the first to the fourth node. An average of three to four explants could be obtained from each seedling. The explants were prepared from plantlets by cutting 0.5 to 1.0 cm below the axillary node on the internode and removing the petiole and leaf from the explant. The tip where the axillary meristems lie was cut with a scalpel to induce de novo shoot growth and allow access of target cells to the *Agrobacterium*. Therefore, a 0.5 cm explant included the stem and a bud.

Once cut, the explants were immediately placed in the *Agrobacterium* suspension for 20 to 30 minutes. After inoculation, the explants were blotted onto sterile filter paper to remove excess *Agrobacterium* culture then placed almost completely immersed in solid CCM or on top of a round 7 cm filter paper overlaying the solid CCM, depending on the *Agrobacterium* strain. This filter paper prevents *Agrobacterium* overgrowth on the soyexplants. Plates were wrapped with Parafilm™ "M" (American National Can, Chicago, Ill., USA) and incubated for two to three days in the dark at 25° C.

8.4—Shoot Induction

After 3 to 5 days co-cultivation in the dark at 25° C., the explants were rinsed in liquid SIM medium (to remove excess *Agrobacterium*) (SIM, see Olhoft et al 2007 A novel *Agrobacterium* rhizogenes-mediated transformation method of soyusing primary-node explants from seedlings In Vitro Cell. Dev. Biol.-Plant (2007) 43:536-549; to remove excess *Agrobacterium*) or Modwash medium (1×B5 major salts, 1×B5 minor salts, 1×MSIII iron, 3% Sucrose, 1×B5 vitamins, 30 mM MES, 350 mg/L Timentin™ pH 5.6, WO 2005/121345) and blotted dry on sterile filter paper (to prevent damage especially on the lamina) before placing on the solid SIM medium. The approximately 5 explants (Method A) or 10 to 20 (Methods B and C) explants were placed such that the target tissue was in direct contact with the medium. During the first 2 weeks, the explants could be cultured with or without selective medium. Preferably, explants were transferred onto SIM without selection for one week.

For leaf explants (Method B), the explant should be placed into the medium such that it is perpendicular to the surface of the medium with the petiole imbedded into the medium and the lamina out of the medium.

For propagated axillary meristem (Method C), the explant was placed into the medium such that it was parallel to the surface of the medium (basipetal) with the explant partially embedded into the medium.

Wrap plates with Scotch 394 venting tape (3M, St. Paul, Minn., USA) were placed in a growth chamber for two weeks with a temperature averaging 25° C. under 18 h light/6 h dark cycle at 70-100 $\mu E/m^2 s$. The explants remained on the SIM medium with or without selection until de novo shoot growth occured at the target area (e.g., axillary meristems at the first node above the epicotyl). Transfers to fresh medium can occur during this time. Explants were transferred from the SIM with or without selection to SIM with selection after about one week. At this time, there was considerable de novo shoot development at the base of the petiole of the leaf explants in a variety of SIM (Method B), at the primary node for seedling explants (Method A), and at the axillary nodes of propagated explants (Method C).

Preferably, all shoots formed before transformation were removed up to 2 weeks after co-cultivation to stimulate new growth from the meristems. This helped to reduce chimerism in the primary transformant and increase amplification of transgenic meristematic cells. During this time the explant may or may not be cut into smaller pieces (i.e. detaching the node from the explant by cutting the epicotyl).

8.5—Shoot Elongation

After 2 to 4 weeks (or until a mass of shoots was formed) on SIM medium (preferably with selection), the explants were transferred to SEM medium medium (shoot elongation medium, see Olhoft et al 2007 A novel *Agrobacterium rhizogenes*-mediated transformation method of soy using primary-node explants from seedlings. In Vitro Cell. Dev. Biol.-Plant (2007) 43:536-549) that stimulates shoot elongation of the shoot primordia. This medium may or may not contain a selection compound.

After every 2 to 3 weeks, the explants were transfer to fresh SEM medium (preferably containing selection) after carefully removing dead tissue. The explants should hold together and not fragment into pieces and retain somewhat healthy. The explants were continued to be transferred until the explant dies or shoots elongate. Elongated shoots >3 cm were removed and placed into RM medium for about 1 week (Method A and B), or about 2 to 4 weeks depending on the cultivar (Method C) at which time roots began to form. In the case of explants with roots, they were transferred directly into soil. Rooted shoots were transferred to soil and hardened in a growth chamber for 2 to 3 weeks before transferring to the greenhouse. Regenerated plants obtained using this method were fertile and produced on average 500 seeds per plant.

Transient GUS expression after 5 days of co-cultivation with *Agrobacterium tumefaciens* was widespread on the seedling axillary meristem explants especially in the regions wounding during explant preparation (Method A). Explants were placed into shoot induction medium without selection to see how the primary-node responds to shoot induction and regeneration. Thus far, greater than 70% of the explants were formed new shoots at this region. Expression of the gene was stable after 14 days on SIM, implying integration of the T-DNA into the soy genome. In addition, preliminary experiments resulted in the formation of positive shoots forming after 3 weeks on SIM.

For Method C, the average regeneration time of a soy plantlet using the propagated axillary meristem protocol was 14 weeks from explant inoculation. Therefore, this method has a quick regeneration time that leads to fertile, healthy soy plants.

Example 9: Pathogen Assay 9.1. Recovery of Clones 2-3 clones per T0 event were potted into small 6 cm pots. For recovery the clones were kept for 12-18 days in the Phytochamber (16 h-day-und 8 h-night-Rhythm at a temperature of 16° to 22° C. und a humidity of 75% were grown).

9.2 Inoculation

The rust fungus is a wild isolate from Brazil. The plants were inoculated with *P. pachyrhizi*.

In order to obtain appropriate spore material for the inoculation, soy leaves which had been infected with rust 15-20 days ago, were taken 2-3 days before the inoculation and transferred to agar plates (1% agar in H2O). The leaves were placed with their upper side onto the agar, which allowed the fungus to grow through the tissue and to produce very young spores. For the inoculation solution, the spores were knocked off the leaves and were added to a Tween-H2O solution. The counting of spores was performed under a light microscope by means of a Thoma counting chamber. For the inoculation of the plants, the spore suspension was added into a compressed-air operated spray flask and applied uniformly onto the plants or the leaves until the leaf surface is well moisturized. For macroscopic assays the inventors used a spore density of 1-5×105 spores/ml. For the microscopy, a density of >5×105 spores/ml is used. The inoculated plants were placed for 24 hours in a greenhouse chamber with an average of 22° C. and >90% of air humidity. The following cultivation was performed in a chamber with an average of 25° C. and 70% of air humidity.

Example 10: Microscopical Screening

For the evaluation of the pathogen development, the inoculated leaves of plants were stained with aniline blue 48 hours after infection.

The aniline blue staining serves for the detection of fluorescent substances. During the defense reactions in host interactions and non-host interactions, substances such as phenols, callose or lignin accumulated or were produced and were incorporated at the cell wall either locally in papillae or in the whole cell (hypersensitive reaction, HR). Complexes were formed in association with aniline blue, which lead e.g. in the case of callose to yellow fluorescence. The leaf material was transferred to falcon tubes or dishes containing destaining solution II (ethanol/acetic acid 6/1) and was incubated in a water bath at 90° C. for 10-15 minutes. The destaining solution II was removed immediately thereafter, and the leaves were washed 2× with water. For the staining, the leaves were incubated for 1.5-2 hours in staining solution II (0.05% aniline blue=methyl blue, 0.067 M di-potassium hydrogen phosphate) and analyzed by microscopy immediately thereafter.

The different interaction types were evaluated (counted) by microscopy. An Olympus UV microscope BX61 (incident light) and a UV Longpath filter (excitation: 375/15, Beam splitter: 405 LP) are used. After aniline blue staining, the spores appeared blue under UV light. The papillae coul be recognized beneath the fungal appressorium by a green/yellow staining. The hypersensitive reaction (HR) was characterized by a whole cell fluorescence.

Example 11: Evaluating the Susceptibility to Soybean Rust

The progression of the soybean rust disease was scored by the estimation of the diseased area (area which was covered by sporulating uredinia) on the backside (abaxial side) of the leaf. Additionally the yellowing of the leaf was taken into account (for scheme see FIG. 2).

11.1 Overexpression of CL7

T0 soybean plants expressing CL7 protein were inoculated with spores of *Phakopsora* pachyrhizi. The macroscopic disease symptoms of 23 T0 soybean plants were scored 14 days after inoculation. The average of the percentage of the leaf area showing fungal colonies or strong yellowing/browning on all leaves was considered as diseased leaf area. At all 23 soybean T0 plants expressing CL7 (expression checked by RT-PCR) were evaluated in parallel to non-transgenic control plants. Clones from non-transgenic soy plants were used as control. The average of the diseased leaf area is shown in FIG. 3 for plants expressing recombinant CL7 compared with wildtype plants. Overexpression of CL7 reduces the diseased leaf area in comparison to non-transgenic control plants by 28% ($p<0.01$). This data clearly indicate that the in planta expression of the CL7 expression vector construct lead to a lower disease scoring of transgenic plants compared to non-transgenic controls. So, the expression of CL7 in soy enhances the resistance of soy against soybean rust.

11.2 Overexpression of CL20

T0 soybean plants expressing CL20 protein were inoculated with spores of *Phakopsora pachyrhizi*. The macroscopic disease symptoms of 25 T0 soybean plants were scored 14 days after inoculation. The average of the percentage of the leaf area showing fungal colonies or strong yellowing/browning on all leaves was considered as diseased leaf area. At all 25 soybean T0 plants expressing CL20 (expression checked by RT-PCR) were evaluated in parallel to non-transgenic control plants. Clones from non-transgenic soy plants were used as control. The average of the diseased leaf area is shown in FIG. 4 for plants expressing recombinant CL20 compared with wildtype plants. Overexpression of CL20 reduces the diseased leaf area in comparison to non-transgenic control plants by 38% ($p<0.01$). This data clearly indicate that the in planta expression of the CL20 expression vector construct lead to a lower disease scoring of transgenic plants compared to non-transgenic controls. So, the expression of CL20 in soy enhances the resistance of soy against soybean rust.

11.3 Overexpression of CL21

T0 soybean plants expressing CL21 protein were inoculated with spores of *Phakopsora* pachyrhizi. The macroscopic disease symptoms of 29 T0 soybean plants were scored 14 days after inoculation. The average of the percentage of the leaf area showing fungal colonies or strong yellowing/browning on all leaves was considered as diseased leaf area. At all 29 soybean T0 plants expressing CL21 (expression checked by RT-PCR) were evaluated in parallel to non-transgenic control plants. Clones from non-transgenic soy plants were used as control. The average of the diseased leaf area is shown in FIG. 5 for plants expressing recombinant CL21 compared with wildtype plants. Overexpression of CL21 reduces the diseased leaf area in comparison to non-transgenic control plants by 45% ($p<0.05$). This data clearly indicate that the in planta expression of the CL21 expression vector construct lead to a lower disease scoring of transgenic plants compared to non-transgenic controls. So, the expression of CL21 in soy enhances the resistance of soy against soybean rust.

11.4 Overexpression of CL24

T0 soybean plants expressing CL24 protein were inoculated with spores of *Phakopsora* pachyrhizi. The macroscopic disease symptoms of 17 T0 soybean plants were scored 14 days after inoculation. The average of the percentage of the leaf area showing fungal colonies or strong yellowing/browning on all leaves was considered as diseased leaf area. At all 17 soybean T0 plants expressing CL24 (expression checked by RT-PCR) were evaluated in parallel to non-transgenic control plants. Clones from non-transgenic soy plants were used as control. The average of the diseased leaf area is shown in FIG. 6 for plants expressing recombinant CL24 compared with wildtype plants. Overexpression of CL24 reduces the diseased leaf area in comparison to non-transgenic control plants by 35% (p<0.05). This data clearly indicate that the in planto expression of the CL24 expression vector construct lead to a lower disease scoring of transgenic plants compared to non-transgenic controls. So, the expression of CL24 in soy enhances the resistance of soy against soybean rust.

11.5 Overexpression of CL4

At all 44 T1 soybean plants (5 independent events, 8-10 transgenic plants each) expressing the CL4 protein were inoculated with spores of *Phakopsora pachyrhizi*. The macroscopic disease symptoms caused by *P. pachyrhizi* on the inoculated soybean plants were scored 14 days after inoculation. The average of the percentage of the leaf area showing fungal colonies or strong yellowing/browning on all leaves was considered as diseased leaf area. At all 44 soybean T1 plants expressing CL4 (expression checked by RT-PCR) were evaluated in parallel to non-transgenic control plants of the same variety. Non-transgenic soy plants grown in parallel to the transgenic plants were used as control. The average of the diseased leaf area is shown in FIG. 7 for plants expressing recombinant CL4 compared with wildtype plants. Overexpression of CL4 reduces the diseased leaf area in comparison to non-transgenic control plants by 28.5% in average (median) over all events generated. This data clearly indicates that the in-planta expression of the CL4 expression vector construct lead to a lower disease scoring of transgenic plants compared to non-transgenic controls. So, the expression of CL4 in soybean significantly ($p<0.01$) increased the resistance of soybean against soybean rust.

11.6 Overexpression of CL13

T0 soybean plants expressing CL13 protein were inoculated with spores of *Phakopsora* pachyrhizi. The macroscopic disease symptoms of 24 T0 soybean plants were scored 14 days after inoculation. The average of the percentage of the leaf area showing fungal colonies or strong yellowing/browning on all leaves was considered as diseased leaf area. At all 24 soybean T0 plants expressing CL13 (expression checked by RT-PCR) were evaluated in parallel to non-transgenic control plants. Clones from non-transgenic soy plants were used as control. The average of the diseased leaf area is shown in FIG. 8 for plants expressing recombinant CL13 compared with wildtype plants. Overexpression of CL13 reduces the diseased leaf area in comparison to non-transgenic control plants by 40% ($p<0.01$). This data clearly indicates that the in-planta expression of the CL13 expression vector construct lead to a lower disease scoring of transgenic plants compared to non-transgenic controls. So, the expression of CL13 in soybean enhances the resistance of soy against soybean rust.

11.7 Overexpression of GLP9

At all 28 T0 soybean plants from 11 independent events expressing GLP9 protein were inoculated with spores of *Phakopsora pachyrhizi*. The macroscopic disease symptoms were scored 14 days after inoculation. The average of the percentage of the leaf area showing fungal colonies or strong yellowing/browning on all leaves was considered as diseased leaf area. At all 28 soybean T0 plants expressing GLP9 (expression checked by RT-PCR) were evaluated in parallel to non-transgenic control plants. Clones from non-transgenic soy plants were used as control. The median of the diseased leaf area of wild type plants and transgenic events is shown in FIG. 9. Overexpression of GLP9 reduces the diseased leaf area in comparison to non-transgenic control plants by 20%. This data clearly shows that the in planta expression of the GLP9 expression vector construct lead to a lower disease scoring of transgenic plants compared to non-transgenic controls. So, the expression of GLP9 in soybean enhances the resistance of soybean against soybean rust.

11.8 Overexpression of CL22

At all 26 T0 soybean plants from 10 independent events expressing the CL22 protein were inoculated with spores of *Phakopsora pachyrhizi*. The macroscopic disease symptoms of the inoculated soybean plants were scored 14 days after inoculation. The average of the percentage of the leaf area showing fungal colonies or strong yellowing/browning on all leaves was considered as diseased leaf area. At all 26 soybean T0 plants expressing CL22 (expression checked by RT-PCR) were evaluated in parallel to non-transgenic control plants. Clones from non-transgenic soy plants were used as control. The average of the diseased leaf area is shown in FIG. 10 for plants expressing recombinant CL22 compared with wildtype plants. Overexpression of CL22 reduces the diseased leaf area in comparison to non-transgenic control plants by 40% ($p<0.01$). This data clearly indicates that the in-planta expression of the CL22 expression vector construct lead to a lower disease scoring of transgenic plants compared to non-transgenic controls. So, the expression of CL22 in soybean enhances the resistance of soybean against soybean rust.

TABLE 1

List of the candidate genes selected by the method described in Example 3

| CL-gene | Description | locus |
|---|---|---|
| CL1 | avirulence-responsive family protein/avirulence induced gene (AIG1) family protein | At1g33950 |
| CL2 | protein kinase family protein | At4g04510 |
| CL3 | expressed protein | At3g57950 |
| CL4 | leucine-rich repeat protein kinase, putative | At1g51860 |
| CL5 | AAA-type ATPase family protein | At5g17760 |
| CL6 | glutamate receptor family protein (GLR2.5) | At5g11210 |
| CL7 | germin-like protein, putative | At5g38910 |
| CL8 | ABC transporter, putative | At3g13090 |
| CL9 | heat shock cognate 70 kDa protein 2 (HSC70-2) (HSP70-2) | At5g02490 |
| CL10 | ACA13: calcium-transporting ATPase, plasma membrane-type, putative/Ca(2+)-ATPase, putative (ACA13) | At3g22910 |
| CL11 | calcineurin-like phosphoesterase family protein | At3g09960 |
| CL12 | invertase/pectin methylesterase inhibitor family protein | At5g46960 |
| CL13 | expressed protein | At1g24575 |
| CL14 | cytochrome P450, putative | At3g03470 |
| CL15 | lectin protein kinase family protein | At3g45410 |
| CL16 | UDP-glucosyltransferase, putative | At3g21560 |

TABLE 1-continued

List of the candidate genes selected by the method described in Example 3

| CL-gene | Description | locus |
|---|---|---|
| CL17 | long-chain-fatty-acid-CoA ligase, putative/long-chain acyl-CoA synthetase, putative | At1g64400 |
| CL18 | DFL-1: auxin-responsive GH3 protein, putative (DFL-1) | At5g54510 |
| CL19 | carbonic anhydrase family protein | At2g28210 |
| CL20 | CA4H: trans-cinnamate 4-monooxygenase/cinnamic acid 4-hydroxylase (C4H) (CA4H)/cytochrome P450 | At2g30490 |
| CL21 | disease resistance family protein/LRR family protein | At4g13820 |
| CL22 | expressed protein | At2g16900 |
| CL23 | ankyrin repeat family protein | At4g14390 |
| CL24 | GDSL-motif lipase/hydrolase family protein | At5g03610 |
| CL25 | peroxidase, putative | At5g06730 |

TABLE 2

Primer sequences for cloning of *Arabidopsis* CL silencing constructs

| Clone type | Sequence name | Name | Primers for Gateway ®-based cloning 5'-3' sequence | SEQ ID NO |
|---|---|---|---|---|
| ds clones | CL1 ds | At1g33950ds_F | GGGGACAAGTTTGTACAAAAAAGCAGGCTTAAGCAGAGCAAGTCCATAAGC | 61 |
| | | At1g33950ds_R | GGGGACCACTTTGTACAAGAAAGCTGGGTATGGAGTAATTGGCGGCAAC | 62 |
| | CL2 ds | At4g04510ds_F | GGGGACAAGTTTGTACAAAAAAGCAGGCTTAAAACCCTCCACGGAGTTAAAGC | 63 |
| | | At4g04510ds_R | GGGGACCACTTTGTACAAGAAAGCTGGGTAGCGAATGTGTCGATAGCAACAG | 64 |
| | CL4 ds | At1g51860ds_F | GGGGACAAGTTTGTACAAAAAAGCAGGCTTATGTGGGTTGGTGCCTAAG | 65 |
| | | At1g51860ds_R | GGGGACCACTTTGTACAAGAAAGCTGGGTAGCCGTGAGGTTGACATTG | 66 |
| | CL8 ds | At3g13090ds_F | GGGGACAAGTTTGTACAAAAAAGCAGGCTTATTCTCCTCCAGCCCATCTACC | 67 |
| | | At3g13090ds_R | GGGGACCACTTTGTACAAGAAAGCTGGGTAGAAACAAGCCAGCGCAGAC | 68 |
| | CL11 ds | At3g09960ds_F | GGGGACAAGTTTGTACAAAAAAGCAGGCTTAAGCTCAGCTCTCGTCATC | 69 |
| | | At3g09960ds_R | GGGGACCACTTTGTACAAGAAAGCTGGGTAATCTTTCCCGCCCATCTC | 70 |
| | CL12 ds | At5g46960ds_F | GGGGACAAGTTTGTACAAAAAAGCAGGCTTACGTGCGTATATGGAAAGC | 71 |
| | | At5g46960ds_R | GGGGACCACTTTGTACAAGAAAGCTGGGTAACAATTGCGGGTCTTTCG | 72 |
| | CL14 ds | At3g03470ds_F | GGGGACAAGTTTGTACAAAAAAGCAGGCTTAGTTGGCTCTGATGTGTTTCG | 73 |
| | | At3g03470ds_R | GGGGACCACTTTGTACAAGAAAGCTGGGTACCTCTTCTTCCCTCCTTCTTTC | 74 |
| | CL15 ds | At3g45410ds_F | GGGGACAAGTTTGTACAAAAAAGCAGGCTTAGCCTGTCAAGTCAACAAG | 75 |
| | | At3g45410ds_R | GGGGACCACTTTGTACAAGAAAGCTGGGTAGTTGCGTATGCATGAGAG | 76 |
| | CL17 ds | At1g64400ds_F | GGGGACAAGTTTGTACAAAAAAGCAGGCTTATGGGTTATGACGCTCTTG | 77 |
| | | At1g64400ds_R | GGGGACCACTTTGTACAAGAAAGCTGGGTAAGTGTGAAGCCATCCATC | 78 |
| | CL18 ds | At5g54510ds_F | GGGGACAAGTTTGTACAAAAAAGCAGGCTTACAAAGATCGCAGCTTTGGAG | 79 |
| | | At5g54510ds_R | GGGGACCACTTTGTACAAGAAAGCTGGGTACACCATTGGCGATTCTGTTG | 80 |
| | CL19 ds | At2g28210ds_F | GGGGACAAGTTTGTACAAAAAAGCAGGCTTAAAGCTAAGACCGGAATGG | 81 |
| | | At2g28210ds_R | GGGGACCACTTTGTACAAGAAAGCTGGGTATGAGAGTGGCGTTACAAG | 82 |
| | CL21 ds | At4g13820ds_F | GGGGACAAGTTTGTACAAAAAAGCAGGCTTAGAGAGGCATGGTCGATTTC | 83 |
| | | At4g13820ds_R | GGGGACCACTTTGTACAAGAAAGCTGGGTAAACTCCGGTAGACTCCACAAC | 84 |
| | CL25ds | At5g06730ds_F | GGGGACAAGTTTGTACAAAAAAGCAGGCTTACGATCTGAGCACACCTGATG | 85 |
| | | At5g06730ds_R | GGGGACCACTTTGTACAAGAAAGCTGGGTACTGCTTCAGTGGCTGATGAC | 86 |
| full length clones | CL5 | At5g17760oe_F | GGGGACAAGTTTGTACAAAAAAGCAGGCTTAATGTTTTTCTCTAAGGATCTTCC | 87 |
| | | At5g17760oe_R | GGGGACCACTTTGTACAAGAAAGCTGGGTATTATGTCCAAAACAATACAAGC | 88 |
| | CL7 | At5g38910oe_F | GGGGACAAGTTTGTACAAAAAAGCAGGCTTAATGAAAAGTTTCTCATTTCTTGCAG | 89 |
| | | At5g38910oe_R | GGGGACCACTTTGTACAAGAAAGCTGGGTATTATGGTTTTATGAACTTGGTCTGT | 90 |
| | CL11 | At3g09960oe_F | GGGGACAAGTTTGTACAAAAAAGCAGGCTTAATGATGACCCAAAAACCA | 91 |
| | | At3g09960oe_R | GGGGACCACTTTGTACAAGAAAGCTGGGTATTAATTGGAAAAATTATCGGTGT | 92 |
| | CL14 | At3g03470oe_F | GGGGACAAGTTTGTACAAAAAAGCAGGCTTAATGGAGATCACCACTATCATATTCC | 93 |
| | | At3g03470oe_R | GGGGACCACTTTGTACAAGAAAGCTGGGTATCACTTTCTCCTTGGATAAATATTTGC | 94 |
| | CL20 | At2g30490oe_F | GGGGACAAGTTTGTACAAAAAAGCAGGCTTAATGGACCTCCTCTTGCTGGA | 95 |
| | | At2g30490oe_R | GGGGACCACTTTGTACAAGAAAGCTGGGTATTAACAGTTCCTTGGTTTCATAACG | 96 |

ds: for double stranded RNA silencing

TABLE 3

Compilation of genes and sequence identifiers

| gene CL | Nucleic acid SEQ ID NO: | gene CL | protein SEQ ID NO: |
|---|---|---|---|
| CL1 | 3 | CL1 | 5 |
| CL1 | 4 | CL1 | 6 |
| CL2 | 35 | CL2 | 36 |
| CL3 | 33 | CL3 | 34 |

TABLE 3-continued

Compilation of genes and sequence identifiers

| gene CL | Nucleic acid SEQ ID NO: | gene CL | protein SEQ ID NO: |
|---|---|---|---|
| CL4 | 7 | CL4 | 8 |
| CL5 | 49 | CL5 | 51 |
| CL5 | 50 | CL5 | 52 |
| CL6 | 47 | CL6 | 48 |

TABLE 3-continued

| Compilation of genes and sequence identifiers | | | |
|---|---|---|---|
| gene CL | Nucleic acid SEQ ID NO: | gene CL | protein SEQ ID NO: |
| CL7 | 53 | CL7 | 54 |
| CL8 | 25 | CL8 | 26 |
| CL9 | 41 | CL9 | 42 |
| CL10 | 29 | CL10 | 30 |
| CL11 | 23 | CL11 | 24 |
| CL12 | 55 | CL12 | 56 |
| CL13 | 1 | CL13 | 2 |
| CL14 | 21 | CL14 | 22 |
| CL15 | 31 | CL15 | 32 |
| CL16 | 27 | CL16 | 28 |
| CL17 | 9 | CL17 | 10 |
| CL18 | 57 | CL18 | 58 |
| CL19 | 17 | CL19 | 18 |
| CL20 | 19 | CL20 | 20 |
| CL21 | 37 | CL21 | 38 |
| CL22 | 11 | CL22 | 14 |
| CL22 | 12 | CL22 | 15 |
| CL22 | 13 | CL22 | 16 |
| CL23 | 39 | CL23 | 40 |
| CL24 | 43 | CL24 | 44 |
| CL25 | 45 | CL25 | 46 |
| GLP9 | 59 | GLP9 | 60 |

The invention claimed is:

1. A method for preventing or reducing *Phakopsora* infection in a transgenic soybean plant, a transgenic soybean plant part, or a transgenic soybean plant cell, said method comprising:

providing a transgenic soybean plant, transgenic soybean plant part, or transgenic soybean plant cell with a heterologous nucleic acid encoding a protein having an amino acid sequence with at least 95% identity with SEQ ID NO:8, wherein the protein confers increased resistance against *Phakopsora* thereto as compared to a wild type soybean plant, a wild type soybean plant part or a wild type soybean plant cell, wherein all of the amino acid residues in the protein not identical to the amino acid sequence of SEQ ID NO:8 are conservative amino acid substitutions; and growing the transgenic soybean plant, transgenic soybean plant part, or transgenic soybean plant cell in the presence of a fungal pathogen of the genus *Phakopsora*, wherein *Phakopsora* infection is prevented or reduced in the transgenic soybean plant, transgenic soybean plant part, or transgenic soybean plant cell as compared to a wild type soybean plant, wild type soybean plant part, or wild type soybean plant cell.

2. The method of claim 1, said method comprising:

(a) stably transforming a soybean plant cell with an expression cassette comprising a heterologous nucleic acid encoding a protein having at least 95% identity with SEQ ID NO: 8 in functional linkage with a promoter, wherein all of the amino acid residues in the protein not identical to the amino acid sequence of SEQ ID NO:8 are conservative amino acid substitutions; and (b) regenerating the soybean plant from the plant cell.

3. The method of claim 1, wherein the heterologous nucleic acid encodes a protein having an amino acid sequence with at least 97% identity to SEQ ID NO: 8.

4. The method of claim 1, wherein the heterologous nucleic acid encodes a protein having an amino acid sequence with at least 98% identity to SEQ ID NO: 8.

5. The method of claim 1, wherein the heterologous nucleic acid encodes a protein having an amino acid sequence with at least 99% identity to SEQ ID NO: 8.

6. The method of claim 1, wherein the heterologous nucleic acid encodes a protein having an amino acid sequence with 100% identity to SEQ ID NO: 8.

* * * * *